United States Patent
Bebernitz et al.

(10) Patent No.: US 8,722,633 B2
(45) Date of Patent: May 13, 2014

(54) GLYCOSIDE DERIVATIVES AND USES THEREOF

(75) Inventors: Gregory Raymond Bebernitz, Cambridge, MA (US); Mark Gary Bock, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/634,597

(22) PCT Filed: Apr. 12, 2012

(86) PCT No.: PCT/IB2012/051798
§ 371 (c)(1),
(2), (4) Date: Sep. 13, 2012

(87) PCT Pub. No.: WO2012/140596
PCT Pub. Date: Oct. 18, 2012

(65) Prior Publication Data
US 2013/0203975 A1    Aug. 8, 2013

Related U.S. Application Data

(60) Provisional application No. 61/475,493, filed on Apr. 14, 2011.

(51) Int. Cl.
*C07H 15/26*    (2006.01)

(52) U.S. Cl.
USPC ............... 514/23; 536/18.7; 536/54; 536/122

(58) Field of Classification Search
CPC ....................................................... C07H 15/26
USPC ............................... 514/23; 536/18.7, 54, 122
See application file for complete search history.

(56) References Cited

U.S. PATENT DOCUMENTS

2006/0035841 A1    2/2006    Eckhardt et al.

FOREIGN PATENT DOCUMENTS

| EP | 1609785 | * 12/2005 |
| WO | 2010/147430 A2 | 12/2010 |
| WO | 2011/048112 A1 | 4/2011 |

OTHER PUBLICATIONS

Adachi et al., Metabolism, vol. 49, No. 8, 2000, 990-995.*

* cited by examiner

*Primary Examiner* — Traviss C McIntosh, III
(74) *Attorney, Agent, or Firm* — Joshua Roth

(57) ABSTRACT

The present invention provides a compound of formula I;

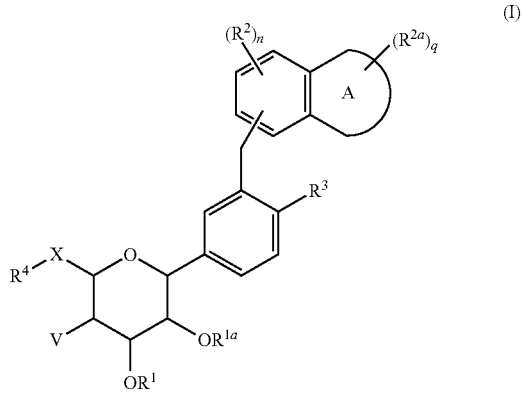

a method for manufacturing the compounds of the invention, and its therapeutic uses. The present invention further provides a combination of pharmacologically active agents and a pharmaceutical composition.

18 Claims, No Drawings

GLYCOSIDE DERIVATIVES AND USES THEREOF

BACKGROUND OF THE INVENTION

Diabetes mellitus is a metabolic disorder characterized by recurrent or persistent hyperglycemia (high blood glucose) and other signs, as distinct from a single disease or condition. Glucose level abnormalities can result in serious long-term complications, which include cardiovascular disease, chronic renal failure, retinal damage, nerve damage (of several kinds), microvascular damage and obesity.

Type 1 diabetes, also known as Insulin Dependent Diabetes Mellitus (IDDM), is characterized by loss of the insulin-producing β-cells of the islets of Langerhans of the pancreas leading to a deficiency of insulin. Type-2 diabetes previously known as adult-onset diabetes, maturity-onset diabetes, or Non-Insulin Dependent Diabetes Mellitus (NIDDM)—is due to a combination of increased hepatic glucose output, defective insulin secretion, and insulin resistance or reduced insulin sensitivity (defective responsiveness of tissues to insulin).

Chronic hyperglycemia can also lead to onset or progression of glucose toxicity characterized by decrease in insulin secretion from β-cell, insulin sensitivity; as a result diabetes mellitus is self-exacerbated [*Diabetes Care*, 1990, 13, 610].

Chronic elevation of blood glucose level also leads to damage of blood vessels. In diabetes, the resultant problems are grouped under "microvascular disease" (due to damage of small blood vessels) and "macrovascular disease" (due to damage of the arteries). Examples of microvascular disease include diabetic retinopathy, neuropathy and nephropathy, while examples of macrovascular disease include coronary artery disease, stroke, peripheral vascular disease, and diabetic myonecrosis.

Diabetic retinopathy, characterized by the growth of weakened blood vessels in the retina as well as macular edema (swelling of the macula), can lead to severe vision loss or blindness. Retinal damage (from microangiopathy) makes it the most common cause of blindness among non-elderly adults in the US. Diabetic neuropathy is characterized by compromised nerve function in the lower extremities. When combined with damaged blood vessels, diabetic neuropathy can lead to diabetic foot. Other forms of diabetic neuropathy may present as mononeuritis or autonomic neuropathy. Diabetic nephropathy is characterized by damage to the kidney, which can lead to chronic renal failure, eventually requiring dialysis. Diabetes mellitus is the most common cause of adult kidney failure worldwide. A high glycemic diet (i.e., a diet that consists of meals that give high postprandial blood sugar) is known to be one of the causative factors contributing to the development of obesity.

Type 2 diabetes is characterized by insulin resistance and/or inadequate insulin secretion in response to elevated glucose level. Therapies for type 2 diabetes are targeted towards increasing insulin sensitivity (such as TZDs), hepatic glucose utilization (such as biguanides), directly modifying insulin levels (such as insulin, insulin analogs, and insulin secretagogues), increasing incretin hormone action (such as exenatide and sitagliptin), or inhibiting glucose absorption from the diet (such as alpha glucosidase inhibitors) [*Nature* 2001, 414, 821-827].

Glucose is unable to diffuse across the cell membrane and requires transport proteins. The transport of glucose into epithelial cells is mediated by a secondary active cotransport system, the sodium-D-glucose co-transporter (SGLT), driven by a sodium-gradient generated by the Na+/K+-ATPase. Glucose accumulated in the epithelial cell is further transported into the blood across the membrane by facilitated diffusion through GLUT transporters [*Kidney International* 2007, 72, S27-S35].

SGLT belongs to the sodium/glucose co-transporter family SLCA5. Two different SGLT isoforms, SGLT1 and SGLT2, have been identified to mediate renal tubular glucose reabsorption in humans [*Curr. Opinon in Investigational Drugs* (2007): 8(4), 285-292 and references cited herein]. Both of them are characterized by their different substrate affinity. Although both of them show 59% homology in their amino acid sequence, they are functionally different. SGLT1 transports glucose as well as galactose, and is expressed both in the kidney and in the intestine, while SGLT2 is found exclusively in the S1 and S2 segments of the renal proximal tubule. As a consequence, glucose filtered in the glomerulus is reabsorbed into the renal proximal tubular epithelial cells by SGLT2, a low-affinity/high-capacity system, residing on the surface of epithelial cell lining in S1 and S2 tubular segments. Much smaller amounts of glucose are recovered by SGLT1, as a high-affinity/low-capacity system, on the more distal segment of the proximal tubule. In healthy human, more than 99% of plasma glucose that is filtered in the kidney glomerulus is reabsorbed, resulting in less than 1% of the total filtered glucose being excreted in urine. It is estimated that 90% of total renal glucose absorption is facilitated by SGLT2; remaining 10% is likely mediated by SGLT1 [*J. Parenter. Enteral Nutr.* 2004, 28, 364-371].

SGLT2 was cloned as a candidate sodium glucose co-transporter, and its tissue distribution, substrate specificity, and affinities are reportedly very similar to those of the low-affinity sodium glucose co-transporter in the renal proximal tubule. A drug with a mode of action of SGLT2 inhibition will be a novel and complementary approach to existing classes of medication for diabetes and its associated diseases to meet the patient's needs for both blood glucose control, while preserving insulin secretion. In addition, SGLT2 inhibitors which lead to loss of excess glucose (and thereby excess calories) may have additional potential for the treatment of obesity.

Indeed small molecule SGLT2 inhibitors have been discovered and the anti-diabetic therapeutic potential of such molecules has been reported in literature [T-1095 (Diabetes, 1999, 48, 1794-1800, Dapagliflozin (Diabetes, 2008, 57, 1723-1729)].

Various O-aryl and O-heteroaryl glycosides have been reported as SGLT-2 inhibitors in patent publications such as: WO 01/74834, WO 03/020737, U.S. Ser. No. 04/0018998, WO 01/68660, WO 01/16147, WO 04/099230, WO 05/011592, U.S. Ser. No. 06/0293252 and WO 05/021566.

Various glucopyranosyl-substituted aromatic and heteroaromatic compounds have also been reported as SGLT-2 inhibitors in patent publications such as: WO 01/27128, WO 04/080990, U.S. Ser. No. 06/0025349, WO 05/085265, WO 05/085237, WO 06/054629 and WO 06/011502.

SGLT1 is predominantly found in the intestine and plays a major role in the absorption of D-glucose and D-galactose. Therefore, SGLT1 inhibitors have the potential to act both in the kidney as well as the intestine to reduce calorie intake and hyperglycemia.

WO2004/018491 discloses pyrazole derivatives which are SGLT1 inhibitors. Glucopyranosyl-substituted aromatic or heteroaromatic compounds where, in general, the sugar moiety has been modified at C4, C5, or C6 positions of pyranose have been published (U.S. Ser. No. 06/0009400, U.S. Ser. No. 06/0019948, U.S. Ser. No. 06/0035841, U.S. Ser. No. 06/0074031, U.S. Ser. No. 08/002,7014 and WO 08/016,132).

Prodrug strategies or methodologies can be used to markedly enhance properties of a drug or to overcome an inherent deficiency in the pharmaceutical or pharmacokinetic properties of a drug. Prodrugs are new chemical entities which, upon administration to the patient, regenerates the parent molecule within the body. Prodrugs can provide choices in modulating the conditions for regeneration of a parent drug and for modulating the physical, pharmaceutic, or pharmacokinetic properties of the parent drug. However, the identification of prodrugs with desired properties is often difficult.

SUMMARY OF THE INVENTION

The invention therefore provides a compound of formula (I):

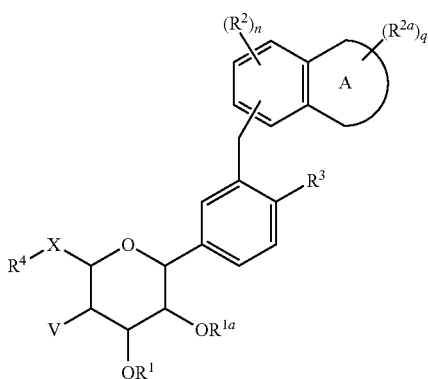

or a pharmaceutically acceptable salt thereof, wherein:
ring A is a 5-, 6- or 7-membered heterocyclyl;
X is O, $NR^5$, S, S(O) or $S(O)_2$;
V is hydrogen, halo or —$OR^{1b}$;
$R^1$, $R^{1a}$ and $R^{1b}$ are independently selected from the group consisting of hydrogen, $C_{1-6}$ alkyl, $C_{6-10}$aryl-$C_{1-4}$alkyl, —$C(O)C_{6-10}$aryl and —$C(O)C_{1-6}$alkyl;
$R^2$ and $R^{2a}$, for each occurrence, are independently selected from the group consisting of halo, hydroxy, cyano, carboxy, $C_{1-6}$alkyl, $C_{1-6}$alkoxy and $C_{3-10}$cycloalkyl;
$R^3$ is halo, hydroxy, $C_{1-6}$alkyl, halo$C_{1-6}$alkyl, $C_{3-10}$cycloalkyl, $C_{1-6}$alkoxy, halo$C_{1-3}$alkoxy or a 3- to 7-membered heterocyclyl;
$R^4$ is a $C_{1-6}$alkyl, halo$C_{1-6}$alkyl, $C_{3-10}$cycloalkyl, $C_{6-10}$aryl, or a 5- to 10-membered heteroaryl;
$R^5$ is hydrogen, $C_{1-6}$alkyl, $C_{3-10}$cycloalkyl, or $C_{1-6}$alkanoyl; or
$R^4$ and $R^5$ together with the nitrogen to which they are attached form a 3- to 7-membered heterocyclyl;
n is 0, 1, 2, or 3; and
q is 0, 1, or 2.

Compounds of the invention are useful for treating diseases and conditions mediated by the sodium D-glucose co-transporter (SGLT), e.g. hyperglycemia, diabetes, and the like. The invention also provides methods of treating such diseases and conditions, and compounds and compositions etc. for their treatment.

The compounds of the invention possess sodium-D-glucose co-transporter (SGLT) inhibition effects, which are beneficial for the prophylaxis, management, treatment, control of progression, or adjunct treatment of diseases and/or medical conditions where the inhibition of SGLT would be beneficial, such as diabetes (including Type-I and Type-II), hyperglycemia, obesity, dyslipidemia, insulin resistance, and other metabolic syndrome, and/or diabetes-related complications including retinopathy, nephropathy, neuropathy, ischemic heart disease, arteriosclerosis, β-cell dysfunction, and as therapeutic and/or prophylactic agents for obesity.

DETAILED DESCRIPTION OF THE INVENTION

Definitions

Unless specified otherwise, the term "compounds of the present invention" refers to compounds of Formula (I) (including the examples), and salts (preferably pharmaceutically acceptable salts) thereof, as well as all stereoisomers (including diastereoisomers and enantiomers), tautomers and isotopically labeled compounds of formula (I) (e.g., deuterium substitutions), as well as inherently formed moieties (e.g., polymorphs, solvates and/or hydrates).

The requisite number of carbon atoms for groups such as alkyl, alkoxy, aryl, etc., is represented as $C_{1-6}$, $C_{1-4}$, etc. in the definitions below. For example, a $C_{1-6}$alkoxy has from one to six carbon atoms and a $C_{1-10}$heteroaryl has from one to 10 carbon atoms.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

As used herein, the term "haloalkyl" refers to an alkyl as defined herein that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

"Alkylene" refers to a straight or branched divalent hydrocarbon chain, having from one to twelve carbon atoms, preferably one to 6 carbon atoms, and linking the rest of the molecule to a radical group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the chain.

"Halogen" or "halo" may be fluoro, chloro, bromo or iodo.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6, more preferably about 1-4 carbons.

As used herein, the term "haloalkoxy" refers to an alkoxy as defined herein that is substituted by one or more halo groups as defined herein. The haloalkoxy can be monohaloalkoxy, dihaloalkoxy or polyhaloalkoxy including perhaloalkoxy. A monohaloalkoxy can have one iodo, bromo, chloro or fluoro within the alkoxy group. Dihaloalkoxy and polyhaloalkoxy groups can have two or more of the same halo atoms or a combination of different halo groups within the alkoxy. Typically the polyhaloalkoxy contains up to 12, or 10, or 8, or 6, or 4, or 3, or 2 halo groups. Non-limiting examples of haloalkyl include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, difluoroethoxy, difluoropropoxy, dichloroethoxy and dichloropropoxy. A perhaloalkoxy refers to an alkoxy having all hydrogen atoms replaced with halo atoms.

As used herein, the term "alkanoyl" refers to alkyl-C(O)—, wherein alkyl is defined herein above. Representative examples of alkanoyl groups include, but are not limited to, acetyl, propionyl, butyryl, 3-isobutyryl, pentanoyl and the like. Preferably, alkanoyl groups have about 1-6, more preferably about 1-4 carbons.

The term "aryl" refers to monocyclic or bicyclic aromatic hydrocarbon groups having 6-10 carbon atoms in the ring portion. Examples include phenyl and naphthyl.

The term "aryl" also refers to a group in which a aryl ring is fused to one or more non-aromatic carbocyclyl provided that at least one ring in the ring system is aromatic. Nonlimiting examples include 2,3-dihydro-1H-inden-5-yl and 1,2,3,4-tetrahydronaphth-2-yl.

The term "arylalkyl" refers to an aryl group which is linked to another moiety via an alkylene group which may be branched or unbranched. Examples of arylalkyl groups include benzyl, 2-phenyl-ethyl, 2-(naphth-2-yl)-butan-1-yl, and the like.

As used herein, the term "heterocyclyl" refers to an optionally substituted, saturated or unsaturated non-aromatic ring or ring system, e.g., which is a 3,4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include dihydrofuranyl, [1,3]dioxolanyl, 1,4-dioxanyl, 1,4-dithianyl, piperazinyl, 1,3-dioxolanyl, imidazolidinyl, imidazolinyl, pyrrolidinyl, dihydropyranyl, oxathiolanyl, dithiolanyl, 1,3-dioxanyl, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, azepinyl, oxapinyl, oxazepinyl and diazepinyl.

As used herein, the term "carbocyclyl" refers to saturated or partially unsaturated (but not aromatic) monocyclic, bicyclic or tricyclic hydrocarbon groups of 3-12 carbon atoms, preferably 3-9, or 3-7 carbon atoms, Exemplary monocyclic hydrocarbon groups include, but are not limited to, cyclopropyl, cyclobutyl, cyclopentyl, cyclopentenyl, cyclohexyl or cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, or bicyclo[2.2.2]octyl. Exemplary tricyclic hydrocarbon groups include adamantyl. A "cycloalkyl" is a carbocyclyl that is completely saturated.

As used herein, the term "heteroaryl" refers to a 5-14 membered monocyclic- or bicyclic- or polycyclic-aromatic ring system having 1 to 8 heteroatoms selected from N, O or S and at least one carbon atom, preferably from 1-10, more preferably from 1-6 carbon atoms, in the ring system. Preferably, the heteroaryl is a 5-10 or 5-7 membered ring system. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. Examples of bicyclic heteroaryl groups include indolyl, benzofuranyl, isoquinolinyl indazolyl, indolinyl, isoindolyl, indolizinyl, benzamidazolyl, and quinolinyl.

The term "heteroaryl" also refers to a group in which an aromatic ring is fused to one or more non-aromatic carbocyclyl or heterocyclyl provided that at least one ring in the ring system is aromatic and at least one ring contains a heteroatom, for example, 3,4-dihydro-2H-benzo[b][1,4]oxazin-7-yl and 1,2,3,4-tetrahydroquinolin-7-yl.

A heteroaryl group may be mono-, bi-, tri-, or polycyclic, preferably mono-, bi-, or tricyclic, more preferably mono- or bicyclic.

The term "heteroarylalkyl" refers to an heteroaryl group which is linked to another moiety via an alkylene group which may be branched or unbranched. Examples of heteroarylalkyl groups include 2-(pyridin-3-yl)-ethyl, 3-(quinolin-7-yl)-butan-1-yl, and the like.

"Heteroaryl" and "heterocyclyl" is also intended to include oxidized S or N, such as sulfinyl, sulfonyl and N-oxide of tertiary ring nitrogen.

Unless indicated explicitly otherwise, where combinations of groups are referred to herein as one moiety, e.g. arylalkyl, the last mentioned group contains the atom by which the moiety is attached to the rest of the molecule.

A "stereoisomer" refers to a compound made up of the same atoms bonded by the same bonds but having different three-dimensional structures, which are not interchangeable.

The present invention contemplates various stereoisomers and mixtures thereof and includes "enantiomers", which refers to two stereoisomers whose molecules are non-superimposeable mirror images of one another.

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. All such isomeric forms are included within the invention. The isomeric forms may be in isomerically pure or enriched form, as well as in mixtures of isomers (e.g. racemic or diastereomeric mixtures).

Accordingly, the invention provides:
stereoisomeric mixtures of compounds of Formula (I);
a diastereomerically enriched or diastereomerically pure isomer of a compound of Formula (I); or
an enantiomerically enriched or enantiomerically pure isomer of a compound of Formula (I).

Where appropriate isomers can be separated from their mixtures by the application or adaptation of known methods (e.g. chromatographic techniques and recrystallisation techniques). Where appropriate isomers can be prepared by the application or adaptation of known methods (e.g. asymmetric synthesis).

Unless otherwise indicated, the present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, can also be obtained in the form of their hydrates or solvates, which include solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

By way of clarity, compounds of the invention included all isotopes of the atoms present in formula (I) and any of the examples or embodiments disclosed herein. For example, H (or hydrogen) represents any isotopic form of hydrogen including $^1H$, $^2H(D)$, and $^3H(T)$; C represents any isotopic form of carbon including $^{12}C$, $^{13}C$, and $^{14}C$; O represents any isotopic form of oxygen including $^{16}O$, $^{17}O$ and $^{18}O$; N represents any isotopic form of nitrogen including $^{13}N$, $^{14}N$ and $^{15}N$; P represents any isotopic form of phosphorous including $^{31}P$ and $^{32}P$; S represents any isotopic form of sulfur including $^{32}S$ and $^{35}S$; F represents any isotopic form of fluorine including $^{19}F$ and $^{18}F$; Cl represents any isotopic form of chlorine including $^{35}Cl$, $^{37}Cl$ and $^{36}Cl$; and the like. In a preferred embodiment, compounds represented by formula (I) comprises isomers of the atoms therein in their naturally occurring abundance. However, in certain instances, it is desirable to enrich one or more atom in a particular isotope which would normally be present in less abundance. For example, $^1H$ would normally be present in greater than 99.98% abundance; however, a compound of the invention can be enriched in $^2H$ or $^3H$ at one or more positions where H is present. In particular embodiments of the compounds of formula (I), when, for example, hydrogen is enriched in the deuterium isotope, the symbol "D" may be used to represent the enrichment in deuterium. In one embodiment, when a compound of the invention is enriched in a radioactive isotope, for example $^3H$ and $^{14}C$, the compound may be useful in drug and/or substrate tissue distribution assays. Likewise, enrichment with positron emitting isotopes, such as $^{11}C$, $^{18}F$, $^{15}O$ and $^{13}N$, can be useful in Positron Emission Topography (PET) studies for examining substrate receptor occupancy. It is to be understood that the invention encompasses all such isotopic forms which inhibit SGLT.

Isotopically-enriched compounds of Formula (I) can generally be prepared by conventional techniques known to those skilled in the art or by processes analogous to those described herein using an appropriate isotopically-enriched reagent in place of the non-enriched reagent previously employed.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal forms include those described in WO 2004/078163. Hence the invention further provides co-crystals comprising a compound of formula (I).

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter, for example blood sugar), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

The amount of the compound of the invention administered should be a therapeutically effective amount where the compound or derivative is used for the treatment of a disease or condition or symptom thereof, and a prophylactically effective amount where the compound or derivative is used for the prevention of a disease or condition or a symptom thereof.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition or a disease, or a symptom thereof, wherein the condition or disease, or symptom thereof, is (i) mediated by SGLT1 and/or SGLT2, (ii) associated with SGLT1 and/or SGLT2 activity, (iii) characterized by activity (normal or abnormal) of SGLT1 and/or SGLT2; or (2) alleviated by reducing or inhibiting the activity of SGLT1 and/or SGLT2. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of SGLT1 and/or SGLT2; or at least partially reducing or inhibiting the expression of SGLT1 and/or SGLT2. The exact dosage will generally be dependent on the patient's status at the time of administration. Factors that may be taken into consideration when determining dosage include the severity of the disease state in the patient, the general health of the patient, the age, weight, gender, diet, time, frequency and route of administration, drug combinations, reaction sensitivities and the patient's tolerance or response to therapy. The precise amount can be determined by routine experimentation, but may ultimately lie with the judgement of the clinician. Generally, an effective dose will be from 0.01 mg/kg/day (mass of drug compared to mass of patient) to 1000 mg/kg/day, e.g. 1 mg/kg/day to 100 mg/kg/day or 1 mg/kg/day to 10 mg/kg/day. Compositions may be administered individually to a patient or may be administered in combination with other agents, drugs or hormones.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. As used herein, the term "disorder" is synonymous with "condition".

The term "comprising" encompasses "including" as well as "consisting", e.g. a composition "comprising" X may consist exclusively of X or may include something additional, e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x+10')/0.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

As used herein, the term "a," "an," "the" and similar terms used in the context of the present invention (especially in the context of the claims) are to be construed to cover both the singular and plural unless otherwise indicated herein or clearly contradicted by the context.

Unless it is explicitly stated that a group is substituted or may optionally be substituted, it is to be understood that the group is unsubstituted.

Compounds of the Invention

Various embodiments of the invention are described herein. It will be recognized that features specified in each embodiment may be combined with other specified features to provide further embodiments.

In one embodiment, the invention provides compounds of formula (I):

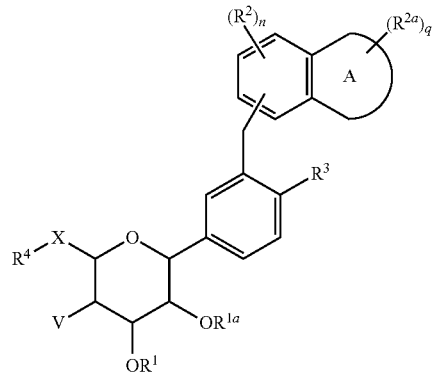

or a pharmaceutically acceptable salt thereof, wherein:
ring A is a 5-, 6- or 7-membered heterocyclyl;
X is O, $NR^S$, S, S(O) or $S(O)_2$;
V is hydrogen, halo or $-OR^{1b}$;
$R^1$, $R^{1a}$ and $R^{1b}$ are independently selected from the group consisting of hydrogen, $C_{1-6}$ alkyl, $C_{6-10}$aryl-$C_{1-4}$alkyl, $-C(O)C_{6-10}$aryl and $-C(O)C_{1-6}$alkyl;
$R^2$ and $R^{2a}$, for each occurrence, are independently selected from the group consisting of halo, hydroxy, cyano, carboxy, $C_{1-6}$alkyl, $C_{1-6}$alkoxy and $C_{3-10}$cycloalkyl;
$R^3$ is halo, hydroxy, $C_{1-6}$alkyl, halo$C_{1-6}$alkyl, $C_{3-10}$cycloalkyl, $C_{1-6}$alkoxy, halo$C_{1-3}$alkoxy or a 3- to 7-membered heterocyclyl;
$R^4$ is a $C_{1-6}$alkyl, halo$C_{1-6}$alkyl, $C_{3-10}$cycloalkyl, $C_{6-10}$aryl, or a 5- to 10-membered heteroaryl;
$R^5$ is hydrogen, $C_{1-6}$alkyl, $C_{3-10}$cycloalkyl, or $C_{1-6}$alkanoyl; or
$R^4$ and $R^5$ together with the nitrogen to which they are attached form a 3- to 7-membered heterocyclyl;
n is 0, 1, 2, or 3; and
q is 0, 1, or 2.

In one embodiment the invention provides compounds of formula (I), or a pharmaceutically acceptable salt thereof, wherein the group represented by the following formula:

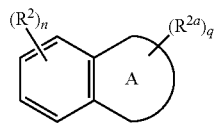

is selected from the group consisting of:

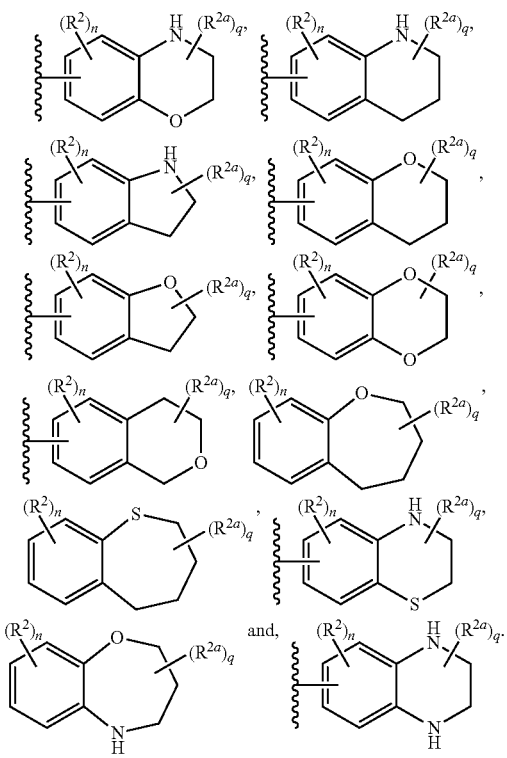

In another embodiment the invention provides compounds of formula (I), or a pharmaceutically acceptable salt thereof, wherein the group represented by the following formula:

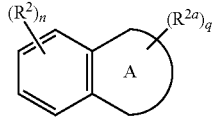

is selected from the group consisting of:

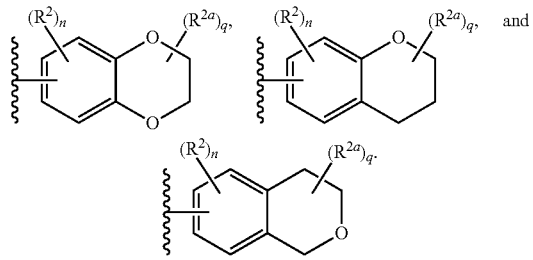

In another embodiment the invention provides compounds of formula (I), or a pharmaceutically acceptable salt thereof, wherein the group represented by the following formula:

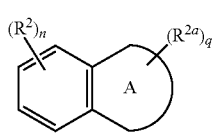

is selected from the group consisting of:

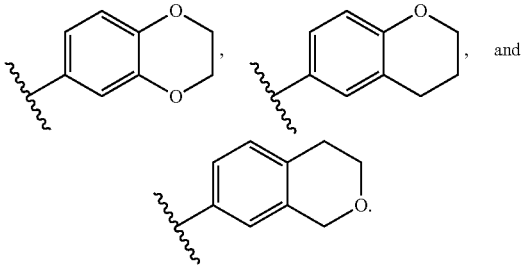

In another embodiment the invention provides compounds of formula (I), or a pharmaceutically acceptable salt thereof, wherein the group represented by the following formula:

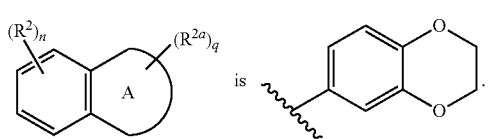

In another embodiment the invention provides compounds of formula (I), or a pharmaceutically acceptable salt thereof, wherein n is 0.
In another embodiment the invention provides compounds of formula (I), or a pharmaceutically acceptable salt thereof, wherein q is 0.

In another embodiment the invention provides compounds of formula (I), or a pharmaceutically acceptable salt thereof, wherein V is —$OR^{1b}$.

In another embodiment the invention provides compounds of formula (I), or a pharmaceutically acceptable salt thereof, wherein $R^1$, $R^{1a}$, and $R^{1b}$ are hydrogen.

In another embodiment the invention provides compounds of formula (I), or a pharmaceutically acceptable salt thereof, wherein $R^3$ is halo, $C_{1-6}$alkyl, or $C_{3-10}$cycloalkyl.

In another embodiment the invention provides compounds of formula (I), or a pharmaceutically acceptable salt thereof, wherein $R^3$ is bromo, ethyl or cyclopropyl.

In another embodiment the invention provides compounds of formula (I), or a pharmaceutically acceptable salt thereof, wherein $R^3$ is ethyl.

In another embodiment the invention provides compounds of formula (I), or a pharmaceutically acceptable salt thereof, wherein X is O.

In another embodiment the invention provides compounds of formula (I), or a pharmaceutically acceptable salt thereof, wherein X is S.

In another embodiment the invention provides compounds of formula (I), or a pharmaceutically acceptable salt thereof, wherein X is $S(O)_2$.

In another embodiment the invention provides compounds of formula (I), or a pharmaceutically acceptable salt thereof, wherein $R^4$ is $C_{1-4}$alkyl, halo$C_{1-4}$alkyl, $C_{3-6}$cycloalkyl, phenyl, or a 5- to 6-membered heteroaryl.

In another embodiment the invention provides compounds of formula (I), or a pharmaceutically acceptable salt thereof, wherein $R^4$ is methyl.

In another embodiment the invention provides compounds of formula (I), or a pharmaceutically acceptable salt thereof, wherein X is $NR^5$.

In another embodiment the invention provides compounds of formula (I), or a pharmaceutically acceptable salt thereof, wherein $R^4$ is a $C_{1-6}$alkyl and $R^5$ is a $C_{1-6}$alkanoyl.

In another embodiment the invention provides compounds of formula (I), or a pharmaceutically acceptable salt thereof, wherein $R^4$ is n-propyl and $R^5$ is acetyl.

In another embodiment the invention provides compounds of formula (I), or a pharmaceutically acceptable salt thereof, wherein $R^4$ and $R^5$ together with the nitrogen to which they are attached form a 5- to 6-membered heterocyclyl.

In another embodiment the invention provides compounds of formula (I), or a pharmaceutically acceptable salt thereof, wherein $R^4$ and $R^5$ together with the nitrogen to which they are attached form a pyrrolidino or a morpholino.

In another embodiment the invention provides compounds of formula (I), or a pharmaceutically acceptable salt thereof, wherein:

the group represented by the following formula:

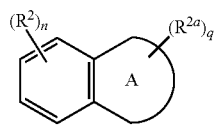

is selected from the group consisting of:

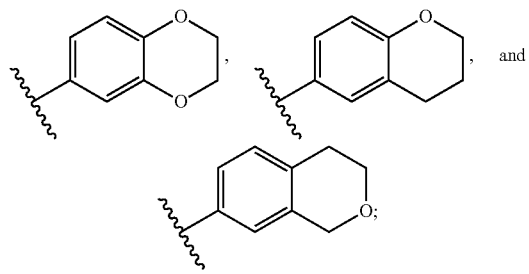

X is O, S, or $S(O)_2$;
V is —$OR^{1b}$;
$R^1$, $R^{1a}$, and $R^{1b}$ are hydrogen;
$R^3$ is halo, $C_{1-6}$alkyl, or $C_{3-10}$cycloalkyl; and
$R^4$ is a $C_{1-4}$alkyl.

In another embodiment the invention provides compounds of formula (I), or a pharmaceutically acceptable salt thereof, wherein:

the group represented by the following formula:

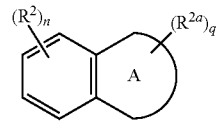

is selected from the group consisting of:

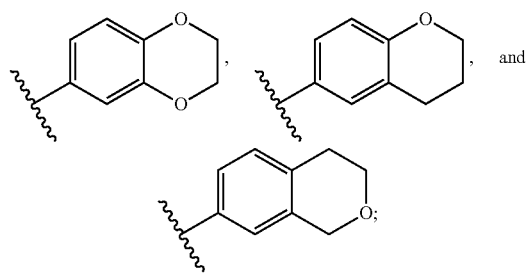

X is O;
V is —$OR^{1b}$;
$R^1$, $R^{1a}$, and $R^{1b}$ are hydrogen;
$R^3$ is halo, $C_{1-6}$alkyl, or $C_{3-10}$cycloalkyl; and
$R^4$ is a $C_{1-4}$alkyl.

In another embodiment the invention provides compounds of formula (I), or a pharmaceutically acceptable salt thereof, wherein:

the group represented by the following formula:

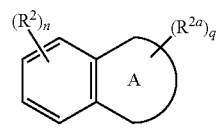

is selected from the group consisting of:

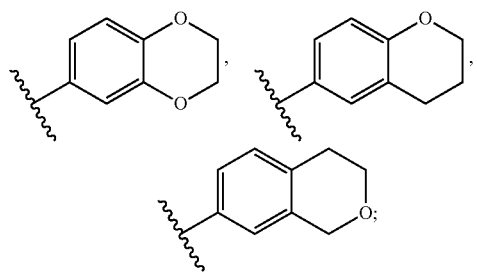

X is S;
V is —OR$^{1b}$;
R$^1$, R$^{1a}$, and R$^{1b}$ are hydrogen;
R$^3$ is halo, C$_{1-6}$alkyl, or C$_{3-10}$cycloalkyl; and
R$^4$ is a C$_{1-4}$alkyl.

In another embodiment the invention provides compounds of formula (I), or a pharmaceutically acceptable salt thereof, wherein:
the group represented by the following formula:

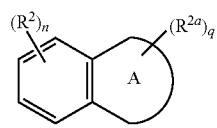

is selected from the group consisting of:

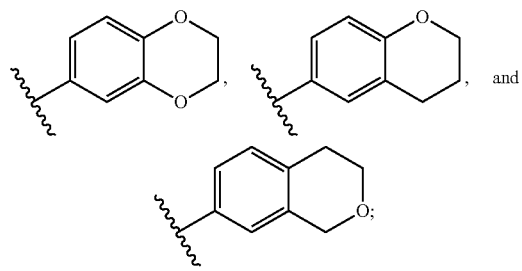

X is S(O)$_2$;
V is —OR$^{1b}$;
R$^1$, R$^{1a}$, and R$^{1b}$ are hydrogen;
R$^3$ is halo, C$_{1-6}$alkyl, or C$_{3-10}$cycloalkyl; and
R$^4$ is a C$_{1-4}$alkyl.

In another embodiment the invention provides compounds of formula (I), or a pharmaceutically acceptable salt thereof, wherein:
the group represented by the following formula:

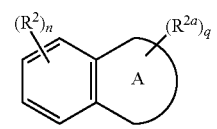

is selected from the group consisting of:

X is O, S, or S(O)$_2$;
V is —OR$^{1b}$;
R$^1$, R$^{1a}$, and R$^{1b}$ are hydrogen;
R$^3$ is bromo, ethyl or cyclopropyl; and
R$^4$ is methyl.

In another embodiment the invention provides compounds of formula (I), or a pharmaceutically acceptable salt thereof, wherein:
the group represented by the following formula:

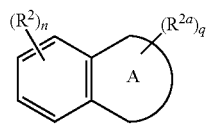

is selected from the group consisting of:

X is NR$^5$;
V is —OR$^{1b}$;
R$^1$, R$^{1a}$, and R$^{1b}$ are hydrogen;
R$^3$ is halo, C$_{1-6}$alkyl, or C$_{3-10}$cycloalkyl;
R$^4$ is a C$_{1-4}$alkyl; and
R$^5$ is a C$_{1-4}$alkanoyl.

In another embodiment the invention provides compounds of formula (I), or a pharmaceutically acceptable salt thereof, wherein:
the group represented by the following formula:

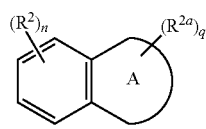

is selected from the group consisting of:

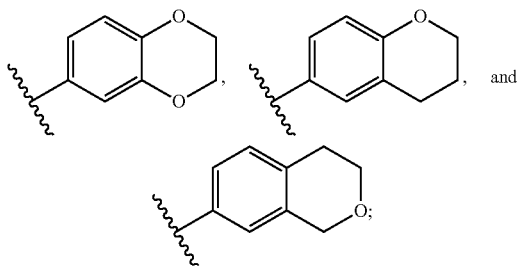

X is $NR^5$;
V is $-OR^{1b}$;
$R^1$, $R^{1a}$, and $R^{1b}$ are hydrogen;
$R^3$ is halo, $C_{1-6}$alkyl, or $C_{3-10}$cycloalkyl; and
$R^4$ and $R^5$, together with the nitrogen atom to which they are attached, form a 3- to 7-membered heterocyclyl.

In another embodiment the invention provides compounds of formula (I), or a pharmaceutically acceptable salt thereof, wherein the compound is selected from the group consisting of:

(2S,3R,4R,5S)-2-[4-cyclopropyl-3-(2,3-dihydro-benzo[1,4]dioxin-6-ylmethyl)-phenyl]-6-methylsulfanyl-tetrahydro-pyran-3,4,5-triol;

(2S,3R,4R,5S,6R)-2-[3-(2,3-Dihydro-benzo[1,4]dioxin-6-ylmethyl)-4-ethyl-phenyl]-6-methylsulfanyl-tetrahydro-pyran-3,4,5-triol;

(2S,3R,4R,5S,6R)-2-(3-Chroman-6-ylmethyl-4-ethyl-phenyl)-6-methylsulfanyl-tetrahydropyran-3,4,5-triol;

(2S,3R,4R,5S,6R)-2-[4-Bromo-3-(2,3-dihydro-benzo[1,4]dioxin-6-ylmethyl)-phenyl]-6-methylsulfanyl-tetrahydro-pyran-3,4,5-triol;

(2S,3R,4R,5S,6R)-2-(3-Chroman-6-ylmethyl-4-cyclopropyl-phenyl)-6-methylsulfanyl-tetrahydropyran-3,4,5-triol;

(2S,3R,4R,5S,6R)-2-(4-Bromo-3-chroman-6-ylmethyl-phenyl)-6-methylsulfanyl-tetrahydropyran-3,4,5-triol;

(2S,3R,4R,5S,6R)-2-(4-Bromo-3-isochroman-7-ylmethyl-phenyl)-6-methylsulfanyl-tetrahydropyran-3,4,5-triol;

(2S,3R,4R,5S,6R)-2-(4-Ethyl-3-isochroman-7-ylmethyl-phenyl)-6-methylsulfanyl-tetrahydropyran-3,4,5-triol;

(2S,3R,4R,5S)-2-[4-Cyclopropyl-3-(2,3-dihydro-benzo[1,4]dioxin-6-ylmethyl)-phenyl]-6-methanesulfonyl-tetrahydro-pyran-3,4,5-triol;

(2S,3R,4R,5S,6R)-2-[3-(2,3-Dihydro-benzo[1,4]dioxin-6-ylmethyl)-4-ethyl-phenyl]-6-methanesulfonyl-tetrahydro-pyran-3,4,5-triol;

(2S,3R,4R,5S,6R)-2-(3-Chroman-6-ylmethyl-4-ethyl-phenyl)-6-methanesulfonyl-tetrahydropyran-3,4,5-triol;

(2S,3R,4R,5S,6R)-2-[4-Bromo-3-(2,3-dihydro-benzo[1,4]dioxin-6-ylmethyl)-phenyl]-6-methanesulfonyl-tetrahydro-pyran-3,4,5-triol;

(2S,3R,4R,5S,6R)-2-(3-Chroman-6-ylmethyl-4-cyclopropyl-phenyl)-6-methanesulfonyl-tetrahydro-pyran-3,4,5-triol;

(2S,3R,4R,5S,6R)-2-(4-Bromo-3-chroman-6-ylmethyl-phenyl)-6-methanesulfonyl-tetrahydropyran-3,4,5-triol;

(2S,3R,4R,5S,6S)-2-[4-Cyclopropyl-3-(2,3-dihydro-benzo[1,4]dioxin-6-ylmethyl)-phenyl]-6-methoxy-tetrahydro-pyran-3,4,5-triol;

(2S,3R,4R,5S,6S)-2-(4-Bromo-3-chroman-6-ylmethyl-phenyl)-6-methoxy-tetrahydro-pyran-3,4,5-triol;

(2S,3R,4R,5S,6S)-2-(3-Chroman-6-ylmethyl-4-ethyl-phenyl)-6-methoxy-tetrahydro-pyran-3,4,5-triol;

(2S,3R,4R,5S,6S)-2-(3-Chroman-6-ylmethyl-4-cyclopropyl-phenyl)-6-methoxy-tetrahydro-pyran-3,4,5-triol;

(2S,3R,4R,5S,6S)-2-[3-(2,3-Dihydro-benzo[1,4]dioxin-6-ylmethyl)-4-ethyl-phenyl]-6-methoxy-tetrahydro-pyran-3,4,5-triol;

N-[(3S,4R,5R,6S)-6-(3-chroman-6-ylmethyl-4-ethyl-phenyl)-3,4,5-trihydroxy-tetrahydro-pyran-2-yl]-N-propyl-acetamide;

2S,3R,4R,5S,6R)-2-[4-Cyclopropyl-3-(2,3,4,5-tetrahydro-benzo[b]oxepin-7-ylmethyl)-phenyl]-6-methylsulfanyl-tetrahydro-pyran-3,4,5-triol;

(2S,3R,4R,5S,6R)-2-[4-Cyclopropyl-3-(2,3,4,5-tetrahydro-benzo[b]thiepin-7-ylmethyl)-phenyl]-6-methylsulfanyl-tetrahydro-pyran-3,4,5-triol (2S,3R,4R,5S,6R)-2-[4-Ethyl-3-(2,3,4,5-tetrahydro-benzo[b]oxepin-7-ylmethyl)-phenyl]-6-methylsulfanyl-tetrahydro-pyran-3,4,5-triol;

(2S,3R,4R,5S,6R)-2-[4-Cyclopropyl-3-(2,3,4,5-tetrahydro-benzo[b]oxepin-7-ylmethyl)-phenyl]-6-Zethylsulfanyl-tetrahydro-pyran-3,4,5-triol;

(2S,3R,4R,5S,6R)-2-[4-Chloro-3-(2,3,4,5-tetrahydro-benzo[b]oxepin-7-ylmethyl)-phenyl]-6-methylsulfanyl-tetrahydro-pyran-3,4,5-triol;

(2S,3R,4R,5S,6R)-2-[4-Methoxy-3-(2,3,4,5-tetrahydro-benzo[b]oxepin-7-ylmethyl)-phenyl]-6-methylsulfanyl-tetrahydro-pyran-3,4,5-triol;

(2S,3R,4R,5S,6R)-2-[4-Cyclopentyl-3-(2,3,4,5-tetrahydro-benzo[b]oxepin-7-ylmethyl)-phenyl]-6-methylsulfanyl-tetrahydro-pyran-3,4,5-triol;

(2S,3R,4R,5S,6R)-2-[4-Cyclobutyl-3-(2,3,4,5-tetrahydro-benzo[b]thiepin-7-ylmethyl)-phenyl]-6-methylsulfanyl-tetrahydro-pyran-3,4,5-triol;

(2R,3S,4R,5R,6S)-2-Methylsulfanyl-6-[4-oxetan-3-yl-3-(2,3,4,5-tetrahydro-benzo[b]oxepin-7-ylmethyl)-phenyl]-tetrahydro-pyran-3,4,5-triol;

(2S,3R,4R,5S,6R)-2-[4-Cyclopropyl-3-(1,2,3,4-tetrahydro-quinolin-7-ylmethyl)-phenyl]-6-methanesulfonyl-tetrahydro-pyran-3,4,5-triol;

(2S,3R,4R,5S,6R)-2-[4-Cyclopropyl-3-(3,4-dihydro-2H-benzo[1,4]oxazin-6-ylmethyl)-phenyl]-6-methanesulfonyl-tetrahydro-pyran-3,4,5-triol;

(2S,3R,4R,5S,6R)-2-(4-cyclopropyl-3-((3,4-dihydro-spiro[benzo[b][1,4]oxazine-2,1'-cyclopropane]-6-yl)methyl)phenyl)-6-(methylsulfonyl)tetrahydro-2H-pyran-3,4,5-triol;

(2S,3R,4R,5S,6R)-2-[4-Cyclopropyl-3-(2-methyl-3,4-dihydro-2H-benzo[1,4]oxazin-6-ylmethyl)-phenyl]-6-methanesulfonyl-tetrahydro-pyran-3,4,5-triol;

(2S,3R,4R,5S,6R)-2-[4-Cyclopropyl-3-(1,1-dioxo-1,2,3,4-tetrahydro-1lambda*6*-benzo[1,4]thiazin-6-ylmethyl)-phenyl]-6-methanesulfonyl-tetrahydro-pyran-3,4,5-triol;

(2S,3R,4R,5S,6R)-2-[4-Cyclopentyl-3-(2,3,4,5-tetrahydro-benzo[b]oxepin-7-ylmethyl)-phenyl]-6-methanesulfonyl-tetrahydro-pyran-3,4,5-triol;

(2R,3S,4R,5R,6S)-2-Methanesulfonyl-6-[4-oxetan-3-yl-3-(2,3,4,5-tetrahydro-benzo[b]oxepin-7-ylmethyl)-phenyl]-tetrahydro-pyran-3,4,5-triol;

(2S,3R,4R,5S,6S)-2-[3-(2,2-Dimethyl-3,4-dihydro-2H-benzo[1,4]oxazin-6-ylmethyl)-4-ethyl-phenyl]-6-methoxy-tetrahydro-pyran-3,4,5-triol;

(2S,3R,4R,5S,6S)-2-[4-Ethyl-3-(1,2,3,4-tetrahydro-quinolin-6-ylmethyl)-phenyl]-6-methoxy-tetrahydro-pyran-3,4,5-triol;

(2S,3R,4R,5S,6S)-2-[4-Cyclopropyl-3-(3,4-dihydro-2H-benzo[1,4]thiazin-6-ylmethyl)-phenyl]-6-methoxy-tetrahydro-pyran-3,4,5-triol;

(2S,3R,4R,5S,6S)-2-[4-Cyclopropyl-3-(3,4-dihydro-2H-1,4-ethano-quinolin-7-ylmethyl)-phenyl]-6-methoxy-tetrahydro-pyran-3,4,5-triol;

(2S,3R,4R,5S,6S)-2-[4-Ethyl-3-(1,2,3,4-tetrahydro-quinoxalin-6-ylmethyl)-phenyl]-6-methoxy-tetrahydro-pyran-3,4,5-triol;

6-[2-Cyclopropyl-5-((2S,3R,4R,5S,6S)-3,4,5-tri hydroxy-6-methoxy-tetrahydro-pyran-2-yl)-benzyl]-3,4-dihydro-2H-benzo[1,4]oxazine-2-carboxylic acid;

6-[2-Cyclopropyl-5-((2S,3R,4R,5S,6S)-3,4,5-tri hydroxy-6-methoxy-tetrahydro-pyran-2-yl)-benzyl]-3,4-dihydro-2H-benzo[1,4]oxazine-2-carbonitrile;

(2S,3R,4R,5S,6S)-2-[4-Cyclopropyl-3-(5-methylamino-5,6,7,8-tetrahydro-naphthalen-2-ylmethyl)-phenyl]-6-methoxy-tetrahydro-pyran-3,4,5-triol;

(2S,3S,4R,5R,6S)-2-Meth oxy-6-[4-oxetan-3-yl-3-(2,3,4,5-tetrahydro-benzo[b]oxepin-7-ylmethyl)-phenyl]-tetrahydro-pyran-3,4,5-triol;

(2S,3R,4R,5S,6S)-2-[4-Cyclopropyl-3-(2,3,4,5-tetra hydro-benzo[b]oxepin-7-ylmethyl)-phenyl]-6-methoxy-tetrahydro-pyran-3,4,5-triol;

(2S,3R,4R,5S,6S)-2-[4-Cyclopropyl-3-(2,3,4,5-tetra hydro-benzo[b]thiepin-7-ylmethyl)-phenyl]-6-methoxy-tetrahydro-pyran-3,4,5-triol;

(2S,3R,4R,5S,6S)-2-[4-Ethyl-3-(2,3,4,5-tetrahydro-benzo[b]oxepin-7-ylmethyl)-phenyl]-6-methoxy-tetra hydro-pyran-3,4,5-triol;

(2S,3R,4R,5S,6S)-2-[4-Chloro-3-(2,3,4,5-tetrahydro-benzo[b]oxepin-7-ylmethyl)-phenyl]-6-methoxy-tetra hydro-pyran-3,4,5-triol;

(2S,3R,4R,5S,6S)-2-[4-Cyclopropyl-3-(6,7,8,9-tetrahydro-5-oxa-9-aza-benzocyclohepten-3-ylmethyl)-phenyl]-6-methoxy-tetra hydro-pyran-3,4,5-triol;

(2S,3R,4R,5S)-2-[3-(2,3-Dihydro-benzo[1,4]dioxin-6-ylmethyl)-4-ethyl-phenyl]-6-phenylsulfanyl-tetrahydro-pyran-3,4,5-triol;

(2S,3R,4R,5S)-2-[3-(2,3-Dihydro-benzo[1,4]dioxin-6-ylmethyl)-4-ethyl-phenyl]-6-(thiophene-2-sulfonyl)-tetra hydro-pyran-3,4,5-triol;

(3S,4R,5R,6S)-2-Cyclopropanesulfonyl-6-[3-(2,3-dihydro-benzo[1,4]dioxin-6-ylmethyl)-4-ethyl-phenyl]-tetrahydro-pyran-3,4,5-triol; and (2S,3R,4R,5S)-2-[3-(2,3-Dihydro-benzo[1,4]dioxin-6-ylmethyl)-4-ethyl-phenyl]-6-(2,2,2-trifluoro-ethanesulfonyl)tetrahydro-pyran-3,4,5-triol.

In another embodiment the invention provides compounds of formula (I), or a pharmaceutically acceptable salt thereof, wherein the compound is selected from the group consisting of:

(2S,3R,4R,5S)-2-[4-cyclopropyl-3-(2,3-dihydro-benzo[1,4]dioxin-6-ylmethyl)-phenyl]-6-methylsulfanyl-tetrahydro-pyran-3,4,5-triol;

(2S,3R,4R,5S,6R)-2-[3-(2,3-Dihydro-benzo[1,4]dioxin-6-ylmethyl)-4-ethyl-phenyl]-6-methylsulfanyl-tetrahydro-pyran-3,4,5-triol;

(2S,3R,4R,5S,6R)-2-(3-Chroman-6-ylmethyl-4-ethyl-phenyl)-6-methylsulfanyl-tetrahydropyran-3,4,5-triol;

(2S,3R,4R,5S,6R)-2-[4-Bromo-3-(2,3-dihydro-benzo[1,4]dioxin-6-ylmethyl)-phenyl]-6-methylsulfanyl-tetrahydro-pyran-3,4,5-triol;

(2S,3R,4R,5S,6R)-2-(3-Chroman-6-ylmethyl-4-cyclopropyl-phenyl)-6-methylsulfanyl-tetrahydropyran-3,4,5-triol;

(2S,3R,4R,5S,6R)-2-(4-Bromo-3-chroman-6-ylmethyl-phenyl)-6-methylsulfanyl-tetrahydropyran-3,4,5-triol;

(2S,3R,4R,5S,6R)-2-(4-Bromo-3-isochroman-7-ylmethyl-phenyl)-6-methylsulfanyl-tetrahydropyran-3,4,5-triol;

(2S,3R,4R,5S,6R)-2-(4-Ethyl-3-isochroman-7-ylmethyl-phenyl)-6-methylsulfanyl-tetrahydropyran-3,4,5-triol;

(2S,3R,4R,5S)-2-[4-Cyclopropyl-3-(2,3-dihydro-benzo[1,4]dioxin-6-ylmethyl)-phenyl]-6-methanesulfonyl-tetrahydro-pyran-3,4,5-triol;

(2S,3R,4R,5S,6R)-2-[3-(2,3-Dihydro-benzo[1,4]dioxin-6-ylmethyl)-4-ethyl-phenyl]-6-methanesulfonyl-tetrahydro-pyran-3,4,5-triol;

(2S,3R,4R,5S,6R)-2-(3-Chroman-6-ylmethyl-4-ethyl-phenyl)-6-methanesulfonyl-tetrahydropyran-3,4,5-triol;

(2S,3R,4R,5S,6R)-2-[4-Bromo-3-(2,3-dihydro-benzo[1,4]dioxin-6-ylmethyl)-phenyl]-6-methanesulfonyl-tetrahydro-pyran-3,4,5-triol;

(2S,3R,4R,5S,6R)-2-(3-Chroman-6-ylmethyl-4-cyclopropyl-phenyl)-6-methanesulfonyl-tetrahydro-pyran-3,4,5-triol;

(2S,3R,4R,5S,6R)-2-(4-Bromo-3-chroman-6-ylmethyl-phenyl)-6-methanesulfonyl-tetrahydro-pyran-3,4,5-triol;

(2S,3R,4R,5S,6S)-2-[4-Cyclopropyl-3-(2,3-dihydro-benzo[1,4]dioxin-6-ylmethyl)-phenyl]-6-methoxy-tetrahydro-pyran-3,4,5-triol;

(2S,3R,4R,5S,6S)-2-(4-Bromo-3-chroman-6-ylmethyl-phenyl)-6-methoxy-tetrahydro-pyran-3,4,5-triol;

(2S,3R,4R,5S,6S)-2-(3-Chroman-6-ylmethyl-4-ethyl-phenyl)-6-methoxy-tetrahydro-pyran-3,4,5-triol;

(2S,3R,4R,5S,6S)-2-(3-Chroman-6-ylmethyl-4-cyclopropyl-phenyl)-6-methoxy-tetrahydro-pyran-3,4,5-triol; and (2S,3R,4R,5S,6S)-2-[3-(2,3-Dihydro-benzo[1,4]dioxin-6-ylmethyl)-4-ethyl-phenyl]-6-methoxy-tetrahydro-pyran-3,4,5-triol.

In another embodiment, the variables in formula (I) are those defined by the groups in the Examples section below.

In another embodiment individual compounds according to the invention are those listed in the Examples section below.

Treatment of Diseases and Conditions

Compounds of Formula (I) have been found to be inhibitors of SGLT. As used herein, inhibition of SGLT means inhibition exclusively of SGLT2, inhibition exclusively of SGLT1 or inhibition of both SGLT1 and SGLT2.

The invention provides a compound of Formula (I), or a pharmaceutically acceptable salt thereof, for use in therapy. The invention further provides a pharmaceutical composition comprising a compound of Formula (I), or a pharmaceutically acceptable salt thereof, in combination with a pharmaceutically acceptable excipient.

The invention further provides a method for the treatment of a disease or condition mediated by the sodium D-glucose co-transporter, comprising the step of administering a therapeutically effective amount of a compound of Formula (I), or a pharmaceutically acceptable salt thereof, to a subject. The invention also provides the use of a compound of Formula (I), or a pharmaceutically acceptable salt thereof, in the manufacture of a medicament for the treatment of a disease or condition mediated by the sodium D-glucose co-transporter. The invention also provides a compound of Formula (I), or a pharmaceutically acceptable salt thereof, for use in treating a disease or condition mediated by the sodium D-glucose co-transporter.

The SGLT inhibitory activity of the compounds of the invention may be demonstrated by the SGLT2 and SGLT1 assays disclosed hereinbelow. Preferred compounds of the invention have an $IC_{50}$ in the SGLT2 assay of <100 nM, in one embodiment <30 nM, in one embodiment <20 nM, in one embodiment <10 nM, in another embodiment <5 nM, and in another embodiment <1 nM, and in another embodiment <0.5 nM. In another embodiment, preferred compounds of the invention have an $IC_{50}$ in the SGLT1 assay of <10,000 nM, in one embodiment <1500 nM, in one embodiment <1000 nM, in one embodiment <700 nM, in another embodiment <500 nM and in another embodiment <200 nM.

The present invention also provides a method of treating diabetes comprising administering a compound of Formula (I), or a pharmaceutically acceptable salt thereof, to a subject in need thereof.

In another embodiment, the invention provides a method of treating a disease or condition mediated by the sodium D-glucose co-transporter in a mammal, comprising administering to the mammal in need thereof a therapeutically effective amount of a compound according to formula (I), or a pharmaceutically acceptable salt thereof.

The compounds of the present invention are useful as both prophylactic and therapeutic treatments for diseases or conditions related to the inhibition of SGLT-2 and/or SGLT-1.

1. Diseases and Conditions Mediated by the Sodium D-Glucose Co-Transporter

The invention is useful for the treatment of a disease or disorder mediated by the sodium D-glucose co-transporter. Diseases and conditions mediated by the sodium D-glucose co-transporter include: metabolic disorders, retinopathy, nephropathy, diabetic foot, ulcers, macroangiopathies, metabolic acidosis or ketosis, reactive hypoglycaemia, hyperinsulinaemia, glucose metabolic disorder, insulin resistance, metabolic syndrome (such as dyslipidemia, obesity, insulin resistance, hypertension, microalbuminemia, hyperuricaemia, and hypercoagulability), dyslipidaemias of different origins, atherosclerosis and related diseases, high blood pressure, chronic heart failure, edema, hyperuricaemia, Syndrome X, diabetes, insulin resistance, decreased glucose tolerance (also known as impaired glucose tolerance, IGT), non-insulin-dependent diabetes mellitus, Type II diabetes, Type I diabetes, diabetic complications, body weight disorders, weight loss, body mass index and leptin related diseases. In one embodiment, the diseases and conditions include metabolic syndrome (such as dyslipidemia, obesity, insulin resistance, hypertension, microalbuminemia, hyperuricaemia, and hypercoagulability), Syndrome X, diabetes, insulin resistance, decreased glucose tolerance (also known as impaired glucose tolerance, IGT), non-insulin-dependent diabetes mellitus, Type II diabetes, Type I diabetes, diabetic complications, body weight disorders, weight loss, body mass index and leptin related diseases. In one embodiment, the disease or disorder is decreased glucose tolerance, Type II diabetes or obesity.

Compounds of formula (I), or a pharmaceutically acceptable salt thereof, may be also suitable for preventing beta-cell degeneration such as apoptosis or necrosis of pancreatic beta cells, for improving or restoring the functionality of pancreatic cells, increasing the number and size of pancreatic beta cells, for use as diuretics or antihypertensives and for the prevention and treatment of acute renal failure.

As a further aspect, the invention relates to a method for treating a disorder selected from type I and type II diabetes mellitus, complications of diabetes, comprising administration of an effective amount of a compound of formula (I) or a pharmaceutically acceptable salt thereof.

As used herein a patient is suffering from "obesity" if the patient exhibits at least one of:
 a body mass index (BMI), i.e. the patient's mass (in kg) divided by the square of the patient's height (in m), of 30 or more;
 an absolute waist circumference of >102 cm in men or >88 cm in women;
 a waist-to-hip ratio >0.9 in men or >0.85 in women; or
 a percent body fat >25% in men or >30% in women.

As used herein a patient is suffering from "Type II diabetes" if they meet the World Health Organisation criteria for Diabetes diagnosis (Definition and diagnosis of diabetes mellitus and intermediate hyperglycaemia, WHO, 2006), i.e. the patient exhibits at least one of:
 a fasting plasma glucose ≥7.0 mmol/l (126 mg/dl); or
 a venous plasma glucose ≥11.1 mmol/l (200 mg/dl) 2 hours after ingestion of 75 g oral glucose load.

As used herein a patient is suffering from "IGT" if they meet the World Health Organisation criteria for IGT diagnosis (Definition and diagnosis of diabetes mellitus and intermediate hyperglycaemia, WHO, 2006), i.e. the patient exhibits both of:
 a fasting plasma glucose ≥7.0 mmol/l (126 mg/dl); and
 a venous plasma glucose ≥7.8 and <11.1 mmol/l (200 mg/dl) 2 hours after ingestion of 75 g oral glucose load.

Administration & Formulation

1. General

For pharmaceutical use, the compounds of the invention may be administered as a medicament by enteral or parenteral routes, including intravenous, intramuscular, subcutaneous, transdermal, airway (aerosol), oral, intranasal, rectal, vaginal and topical (including buccal and sublingual) administration. The compounds of Formula (I) should be assessed for their biopharmaceutical properties, such as solubility and solution stability (across pH), permeability, etc., in order to select the most appropriate dosage form and route of administration for treatment of the proposed indication. In one embodiment the compounds are administered orally.

The compounds of the invention may be administered as crystalline or amorphous products. The compounds of the invention may be administered alone or in combination with one or more other compounds of the invention or in combination with one or more other drugs (or as any combination thereof). Generally, they will be administered as a formulation in association with one or more pharmaceutically acceptable excipients. The term "excipient" includes any ingredient other than the compound(s) of the invention which may impart either a functional (e.g drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

The present invention provides a pharmaceutical composition comprising a compound according to Formula (I), or a pharmaceutically acceptable salt thereof, and a pharmaceutically acceptable excipient.

Typical pharmaceutically acceptable excipients or carriers include:
 diluents, e.g. lactose, dextrose, sucrose, mannitol, sorbitol, cellulose and/or glycine;
 lubricants, e.g. silica, talcum, stearic acid, its magnesium or calcium salt and/or polyethyleneglycol;
 binders, e.g. magnesium aluminum silicate, starch paste, gelatin, tragacanth, methylcellulose, sodium carboxymethylcellulose and/or polyvinylpyrrolidone;
 disintegrants, e.g. starches, agar, alginic acid or its sodium salt, or effervescent mixtures; and/or
 absorbants, colorants, flavors and/or sweeteners.

A thorough discussion of pharmaceutically acceptable excipients is available in Gennaro, *Remington: The Science and Practice of Pharmacy* 2000, 20th edition (ISBN: 0683306472).

Accordingly, in one embodiment, the present invention provides a pharmaceutical composition comprising a compound of Formula (I), or a pharmaceutically acceptable salt thereof, and one or more pharmaceutically acceptable carrier.

2. Oral Administration

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of Formula (I) in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, *Expert Opinion in Therapeutic Patents* 2001, 11(6): 981-986.

The formulation of tablets is discussed in H. Lieberman and L. Lachman, *Pharmaceutical Dosage Forms Tablets* 1980, vol. 1 (Marcel Dekker, New York).

3. Parenteral Administration

The compounds of the invention can be administered parenterally.

The compounds of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of Formula (I) used in the preparation of parenteral solutions may be increased by the use of appropriate formulation techniques, such as the incorporation of co-solvents and/or solubility-enhancing agents such as surfactants, micelle structures and cyclodextrins.

4. Inhalation & Intranasal Administration

The compounds of the invention can be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, for example, PGLA. Modified release formulations include delayed-, sustained-, pulsed-, controlled-, targeted and programmed release.

5. Transdermal Administration

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Combination Therapy

A compound of formula (I), or a pharmaceutically acceptable salt thereof, may be usefully combined with another pharmacologically active compound, or with two or more other pharmacologically active compounds, for use in therapy. For example, a compound of the formula (I), or a pharmaceutically acceptable salt thereof, as defined above, may be administered simultaneously, sequentially or separately in combination with one or more agents for the treatment of disorders previously listed.

Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, orfructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoidi receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-01 13, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes. Such combinations may offer significant advantages, including synergistic activity, in therapy.

The present invention thus provides:
The use of an agent selected from the group consisting of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid, and aspirin in the manufacture of a medicament for the treatment of a disease or condition in a subject mediated by the sodium D-glucose co-transporter, wherein the agent is administered in combination with a compound according to Formula (I), or a pharmaceutically acceptable salt thereof.

The use of a compound according to Formula (I), or a pharmaceutically acceptable salt thereof, in the manufacture of a medicament for the treatment of a disease or condition in a subject mediated by the sodium D-glucose co-transporter, wherein the compound is administered in combination with an agent selected from the group consisting of insulin, insulin derivative, insulin mimetic; insulin secretagogue; insulinotropic sulfonylurea receptor ligand; PPAR ligand; insulin sensitizer; biguanide; alpha-glucosidase inhibitors; GLP-1, GLP-1 analog, GLP-1 mimetic; DPPIV inhibitor; HMG-CoA reductase inhibitor; squalene synthase inhibitor; FXR ligand, LXR ligand; cholestyramine; fibrates; nicotinic acid, and aspirin.

The use of a compound according to formula (I), or a pharmaceutically acceptable salt thereof, in combination with an agent selected from the group consisting of insulin, insulin derivative, insulin mimetic; insulin secretagogue; insulinotropic sulfonylurea receptor ligand; PPAR ligand; insulin sensitizer; biguanide; alpha-glucosidase inhibitors; GLP-1, GLP-1 analog, GLP-1 mimetic; DPPIV inhibitor; HMG-CoA reductase inhibitor; squalene synthase inhibitor; FXR ligand, LXR ligand; cholestyramine; fibrates; nicotinic acid, and aspirin.

The present invention also provides a pharmaceutical composition comprising a therapeutically effective amount of a compound of Formula (I) in combination with a therapeutically effective amount of insulin, insulin derivative, insulin mimetic; insulin secretagogue; insulinotropic sulfonylurea receptor ligand; PPAR ligand; insulin sensitizer; biguanide; alpha-glucosidase inhibitors; GLP-1, GLP-1 analog, GLP-1 mimetic; DPPIV inhibitor; HMG-CoA reductase inhibitor; squalene synthase inhibitor; FXR ligand, LXR ligand; cholestyramine; fibrates; nicotinic acid, and aspirin for simultaneous, separate or sequential use in therapy.

Pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid bile acid binding resins such as cholestyramine; fibrates; nicotinic acid and other GPR109 agonists; cholesterol absorption inhibitors such as ezetimibe; CETP inhibitors (cholesterol-ester-transfer-protein inhibitors), and aspirin;

c) anti-obesity agents such as orlistat, sibutramine and Cannabinoid Receptor 1 (CB1) antagonists e.g. rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

Thus, the present invention provides a pharmaceutical combination comprising:
 i) a compound according of Formula (I), or a pharmaceutically acceptable salt thereof,
 ii) at least one compound selected from
  a) antidiabetic agents,
  b) hypolipidemic agents,
  c) anti-obesity agents,
  d) anti-hypertensive agents,
  e) agonists of peroxisome proliferator-activator receptors.

Biological Assays

The inhibitory effect on the sodium-dependent glucose co-transporter SGLT (SGLT1 and SGLT2), of compounds of formula I may be demonstrated using the following test procedures.

The ability of the substances to inhibit the SGLT-2 activity may be demonstrated in a test set-up in which a CHO-K1 cell line (ATCC No. CCL 6 1) or alternatively an HEK293 cell line (ATCC No. CRL-1573) is stably transfected with an expression vector pZeoSV (Invitrogen, EMBL accession number L36849) which contains the cDNA for the coding sequence of the human sodium glucose co-transporter 2 (Genbank Acc. No. NM_003041) (CHO-hSGLT2 or HEK-hSGLT2). These cell lines transport $^{14}$C-labelled alpha-methyl-glucopyranoside ($^{14}$C-AMG, Amersham) into the interior of the cell in sodium-dependent manner.

The SGLT-2 assay is carried out as follows: CHO-hSGLT2 cells are cultivated in Ham's F12 Medium (BioWhittaker) with 10% foetal calf serum and 250 μg/mL zeocin (Invitrogen), and HEK293-hSGLT2 cells are cultivated in DMEM medium with 10% foetal calf serum and 250 μg/mL zeocin (Invitrogen). The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% $CO_2$. The cells are washed twice with 250 μl of assay buffer (Hanks Balanced Salt Solution, 137 mM NaCl, 5.4 mM KCl, 2.8 mM CaCl2, 1.2 mM MgSO4 and 10 mM HEPES (pH 7.4), 50 μg/mL of gentamycin). 250 μl of assay buffer and 5 μl of test compound are then added to each well and the plate is incubated for a further 15 minutes in the incubator. 5 μl of 10% DMSO are used as the negative control. The reaction is started by adding 5 μl of 14 C— AMG (0.05 μCi) to each well. After 2 hours' incubation at 37° C., 5% $CO_2$, the cells are washed again with 250 μl of PBS (200 C) and then lysed by the addition of 25 μl of 0.1 N NaOH (5 min. at 37° C.). 200 μl of MicroScint20 (Packard) are added to each well and incubation is continued for a further 20 min at 37° C. After this incubation the radioactivity of the $^{14}$C-AMG absorbed is measured in a Topcount (Packard) using a $^{14}$C scintillation program.

To determine the selectivity with respect to human SGLT1 an analogous test is set up in which the cDNA for hSGLTI (Genbank Acc. No. NM000343) instead of hSGLT2 cDNA is expressed in CHO-K1 or HEK293 cells.

The compounds according to the invention may for example have $EC_{50}$ values below 1000 nM, particularly below 100 nM, most preferably below 10 nM for SGLT2. The following compounds of the Examples were evaluated in the above described assays and the results of which are collated in Table 1.

TABLE 1

| Example Number | SGLT2 $IC_{50}$ nM (n = 1-4) | SGLT1 $IC_{50}$ nM (n = 1-4) |
| --- | --- | --- |
| 1 | 0.29 | 0.55 |
| 1-1 | 0.36 | No data |
| 2 | 9.2 | 97 |
| 2-1 | 1.45 | 195 |

It can be seen that the compounds of the invention are useful as inhibitors of SGLT and therefore useful in the treatment of diseases and conditions mediated by SGLT such as the metabolic disorders disclosed herein.

Method of Preparation

The invention provides, in another aspect, a process for preparing a compound of Formula (I). The schemes, outlined below, show general routes for synthesizing compounds of Formula (I). In the reactions described in the schemes herein below, any reactive group present, such as hydroxyl, amino, carbonyl or imino groups may be protected during the reaction by conventional protecting groups such as trimethylsilyl, tert-butyldimethylsilyl, benzyl, acetal, ketal etc., which are cleaved again after the reaction. Unless otherwise stated in the reaction schemes below, the variables have the meaning as defined hereinabove.

Scheme 1:

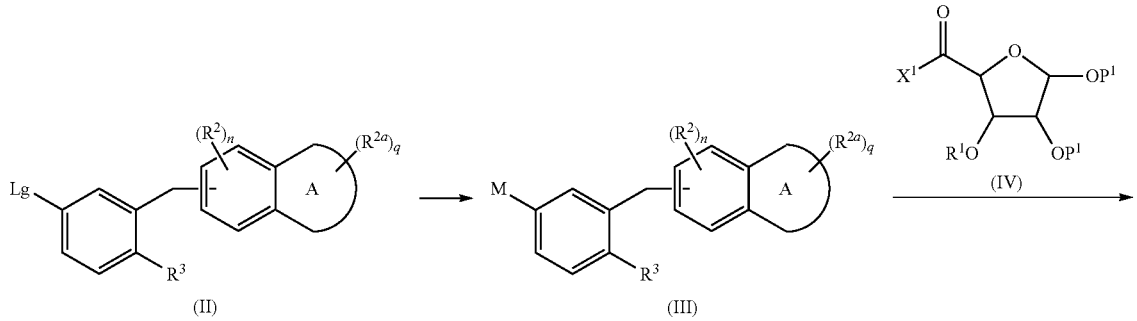

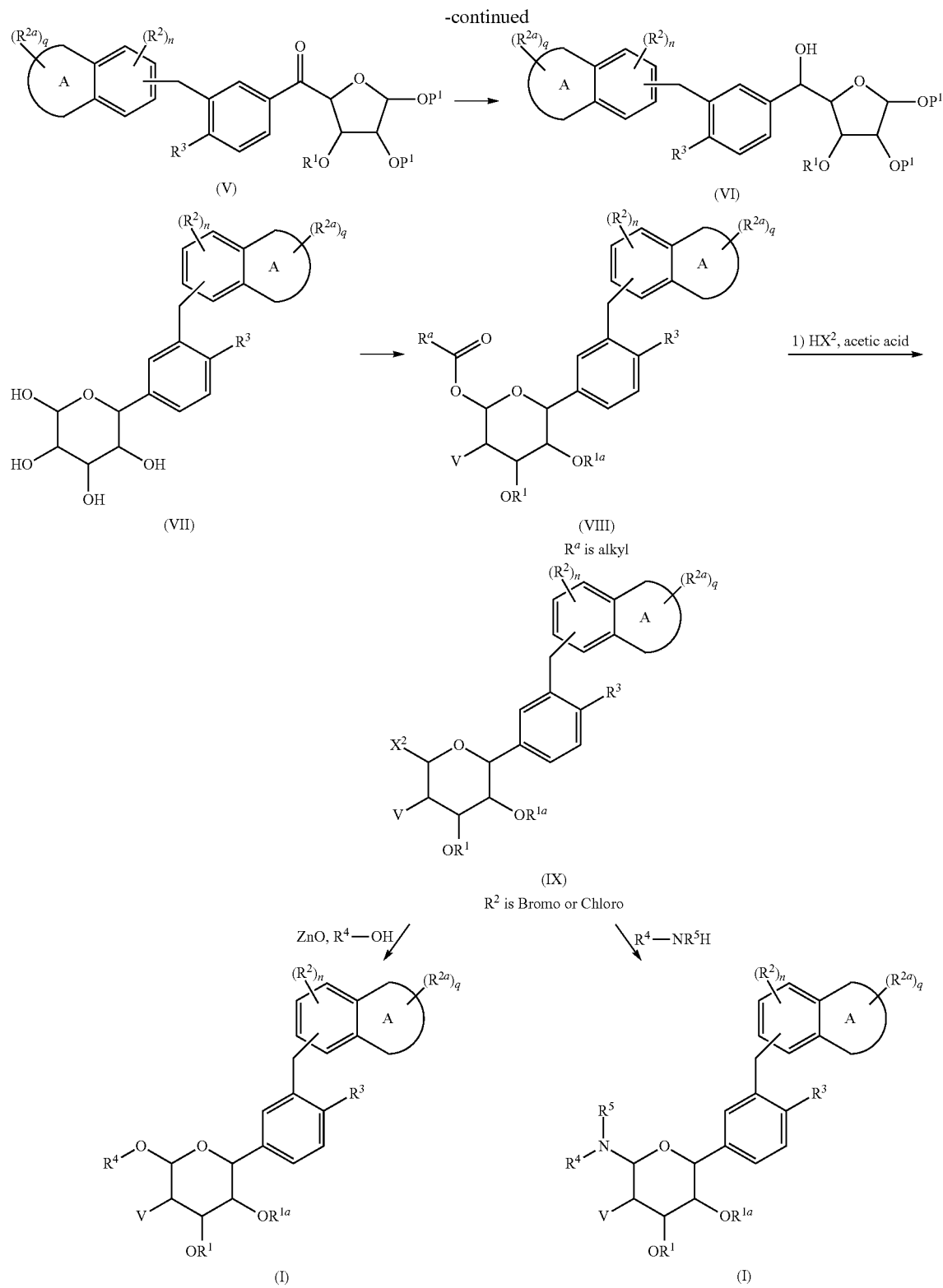

Compounds of formula (II), wherein Lg is a leaving group such as halogen may be reacted with alkyl lithium or Mg to provide compounds of formula (III) wherein M is selected from Li or Mg-Halogen. Compounds of formula (III) may be reacted with compounds of formula (IV) wherein $P^1$ is a protecting group such as acetonide and $X^1$ is halogen or carbonate, to provide compound of formula (V) which may be reduced to provide compounds of formula (VI). The compounds of formula (VI) may be rearranged to obtain compounds of formula (VII). The anomeric alcohol group of formula (VII) may be converted to an ester then substituted with a halogen by treating it with a hydrohalic acid such as HBr or HCl in acetic acid to form a compound represented by Formula (IX). The halogen of Formula (IX) may be displaced with an alcohol to form a compound of Formula (I) wherein X is —O— or an amine to form a compound of Formula (I) wherein X is NR$^5$ (see Scheme 1).

Scheme 2:

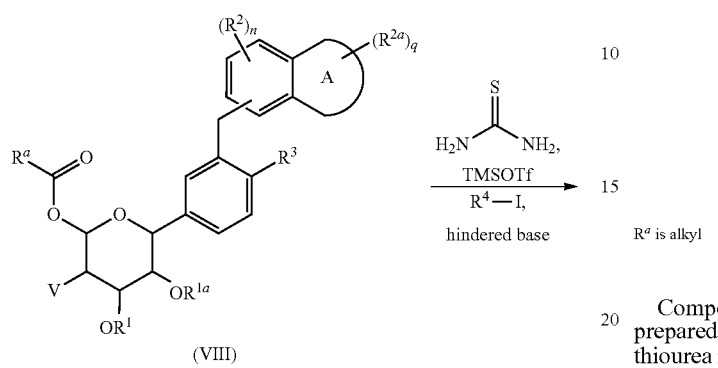

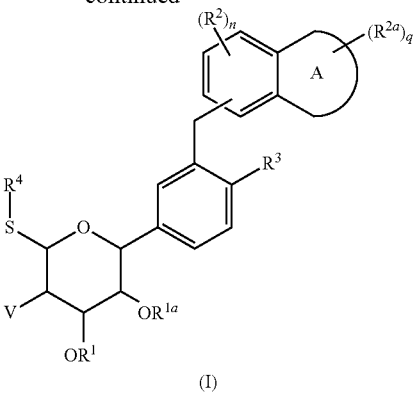

Compounds of the invention in which X is —S— can be prepared by reacting a compound of Formula (VIII) with thiourea in the presence of trimethyl silyl triflate followed by treatment with an alkyl iodide compound in the presence of a hindered base (see Scheme 2).

Scheme 3:

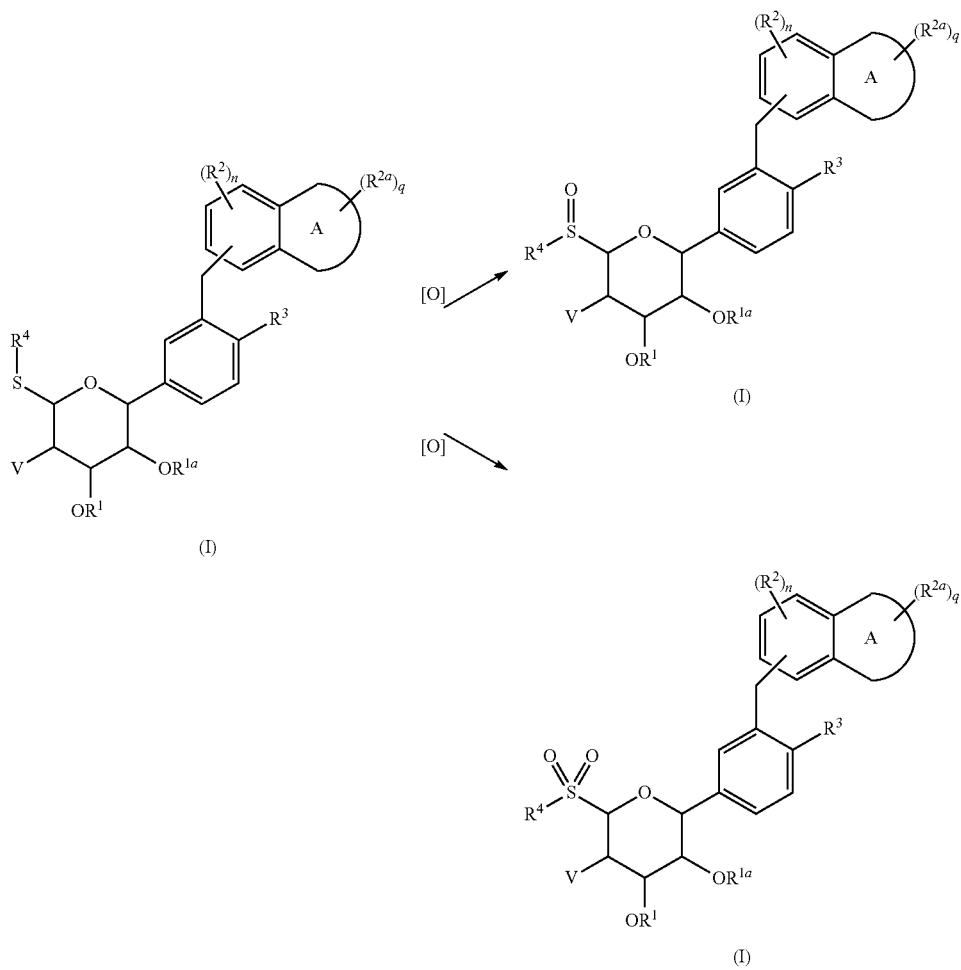

Compounds of Formula (I) wherein X is —S(O)— or —S(O)$_2$— can be prepared from a compound of formula (I) wherein in X is —S— by treating it with an oxidizing agent such as urea hydrogen peroxide (see Scheme 3).

Scheme 4:

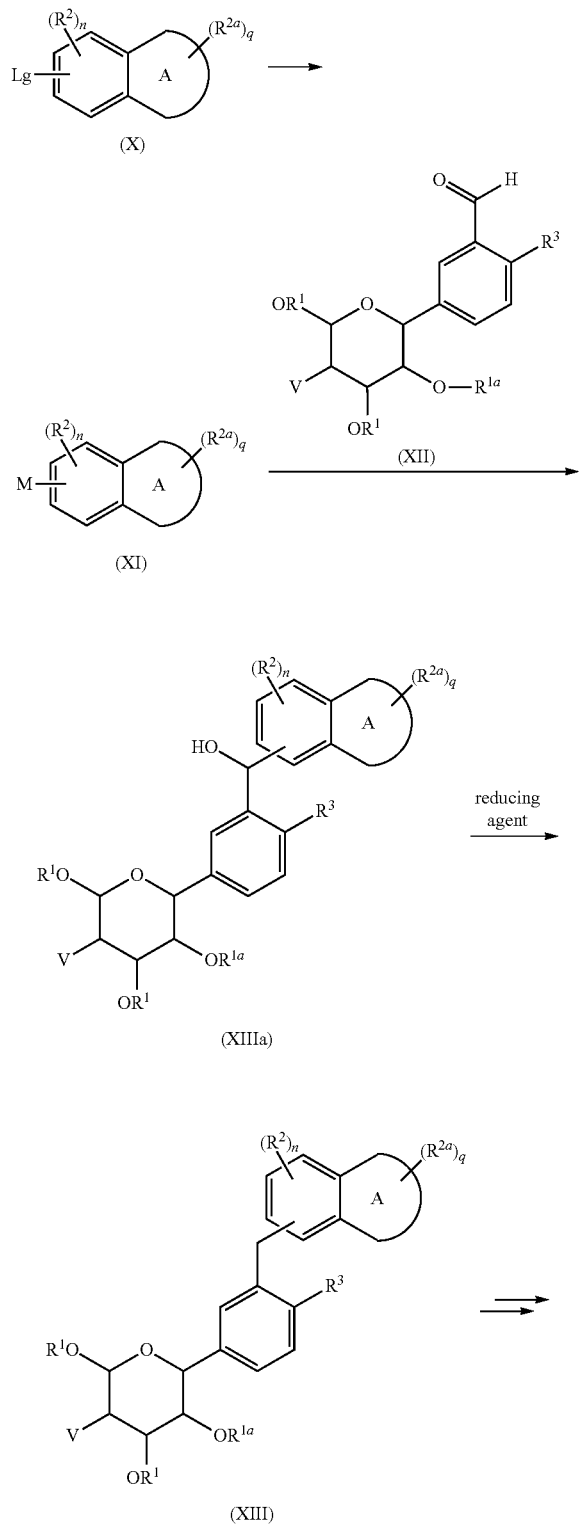

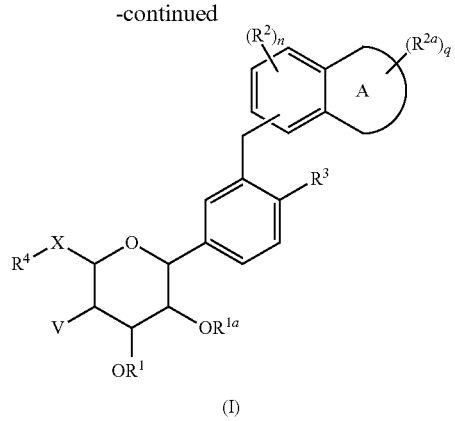

A compound of formula (X), wherein Lg is a leaving group such as halogen, may be reacted with alkyl lithium or Mg to provide compounds of formula (XI) wherein M is selected from Li or Mg-Halide. A compound of formula (XI) may be reacted with aldehyde of formula (XII) to provide an alcohol of Formula (XIIIa) which can be reduced with a reducing agent. In one embodiment, compounds represented by Formula (IIIa) can be reduced by treatment with a trialkylsilane in the presense of BF$_3$ and an ether. A compound of Formula (XIII) may further be converted to a compound of formula (I) by the reactions described in Schemes 1-3 (see Scheme 4).

Scheme 5:

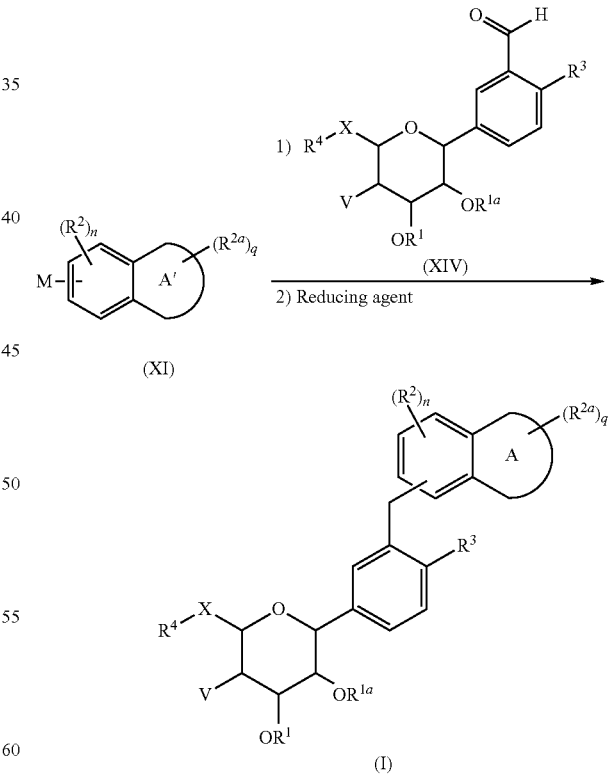

Alternatively, a compound of formula (XI) wherein M is selected from Li or Mg-Halide may be reacted with an aldehyde of formula (XIV) followed by reduction with a reducing agent such as a trialkylsilane in the presense of BF$_3$ and an ether to provide compounds of formula (I) (see Scheme 5).

Scheme 6:

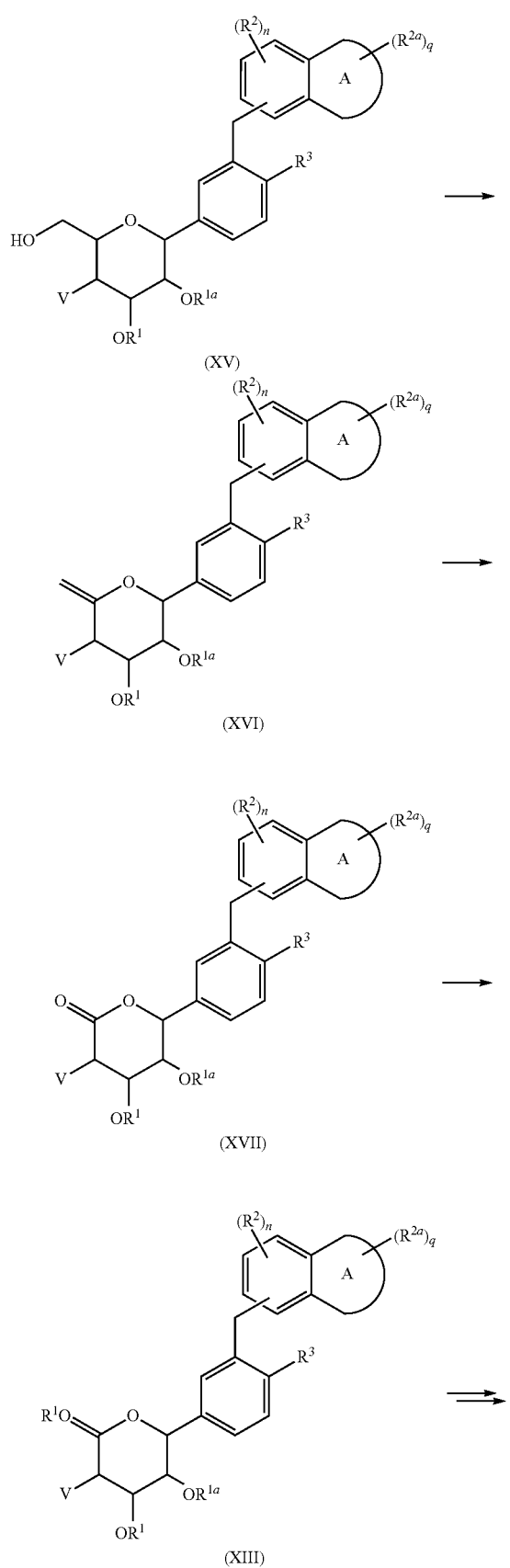

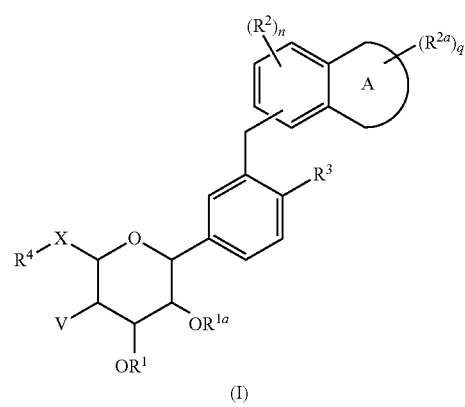

A compound of formula (XV) may be converted to olefin of Formula (XVI) which may be converted to lactone of Formula (XVII) using ozonlysis or dihydroxylation followed by periodate cleavage. A compound of formula (XVII) may be converted to a compound of formula (XIII) which is further converted to a compound of Formula (I) as described in Schemes 1-3 (see Scheme 6).

Intermediates

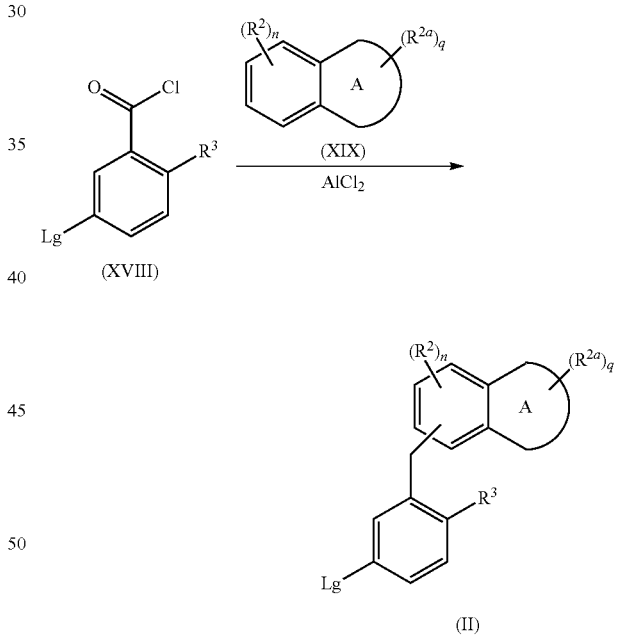

Intermediate (II) can be prepared by reacting an acid chloride (XVIII) with an aromatic compound represented by Formula (XIX) in the presence of $AlCl_3$ as shown in Scheme 7.

Scheme 8: Preparation of Intermediate (IV)

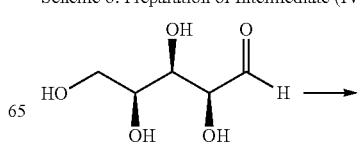

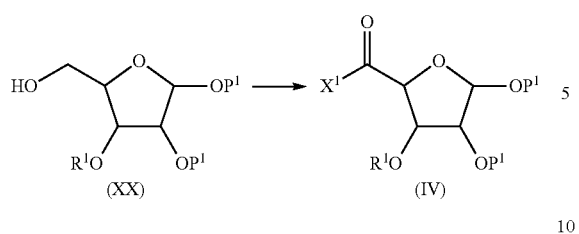

3,4,5-Trihydroxy-2-(R)-hydroxy-pentanal may be cyclised to obtain furanyl alcohol of formula (XX) which may be converted to intermediate (IV) using functional group transformations known in the literature.

Scheme 9: Preparation of Intermediates (XII) and (XIV)

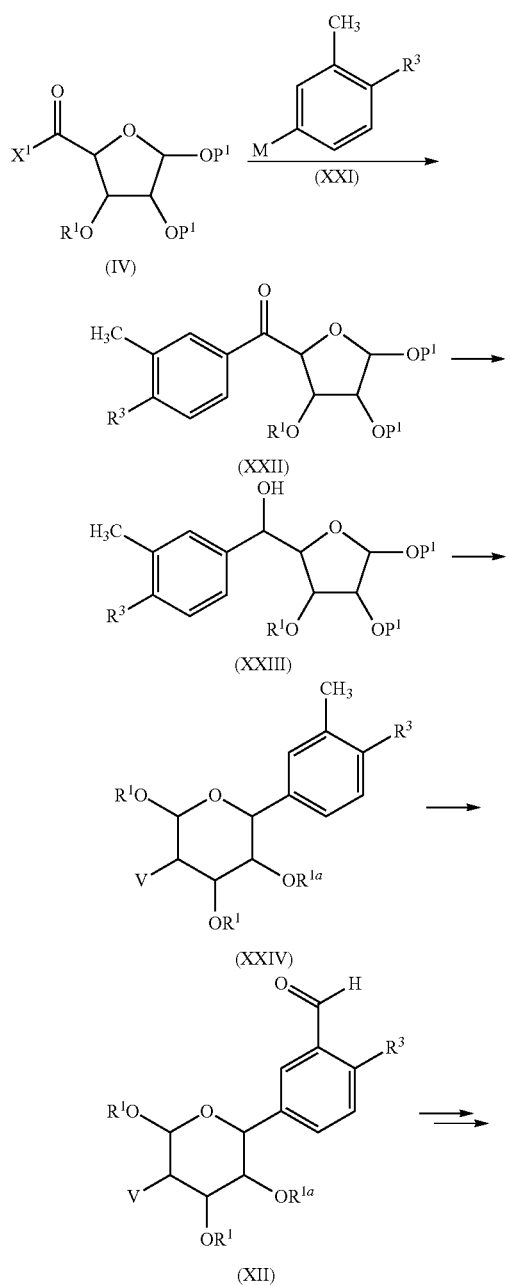

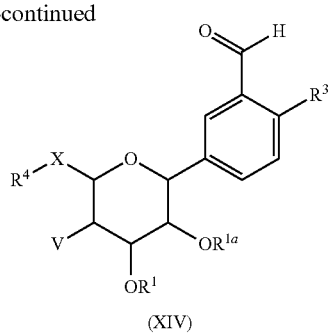

Compounds of formula (IV) may be reacted with organometalic intermediate of formula (XXI) to provide compounds of formula (XXII) which may further be reduced to obtain compounds of formula (XXIII). Compounds of formula (XXIII) on rearrangement and appropriate protection may provide compounds of formula (XXIV). Compounds of formula (XXIV) may be oxidized to provide aldehyde of formula (XII) which may further be converted to a compound of formula (XIV) by the reactions described in Schemes 1-3 (see Scheme 9).

It will be understood that the processes detailed above and elsewhere herein are solely for the purpose of illustrating the invention and should not be construed as limiting. A process utilizing similar or analogous reagents and/or conditions known to one skilled in the art may also be used to obtain a compound of the invention.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

The following Examples are intended to illustrate the invention and are not to be construed as being limitations thereon. If not mentioned otherwise, all evaporations are performed under reduced pressure. The structure of final products, intermediates and starting materials have been confirmed by standard analytical methods, e.g., microanalysis, melting point (m.p.) and spectroscopic characteristics, e.g. MS and NMR. Abbreviations used are those conventional in the art.

Intermediates

Synthesis of 6-(2-bromo-5-iodo-benzyl)-2,3-dihydro-benzo[1,4]dioxine

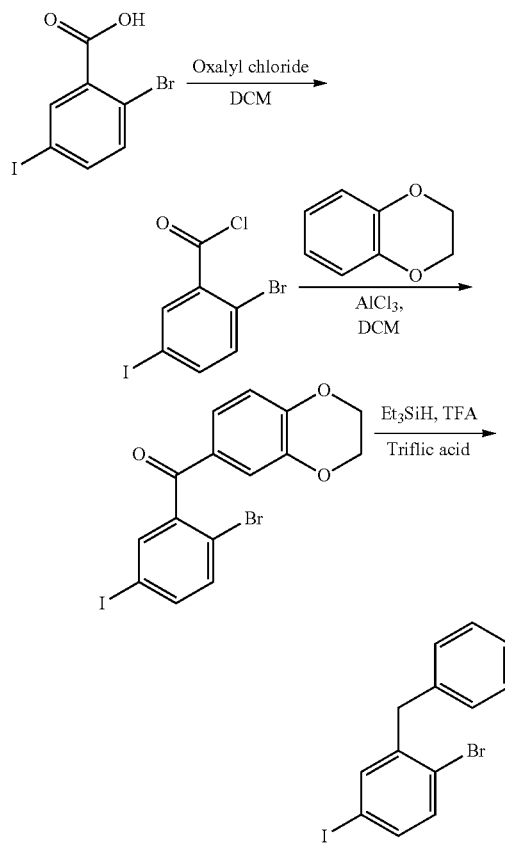

Step I: To a stirred solution of 2-bromo-5-iodobenzoic acid (150 g, 458 mmol) in dichloromethane (1500 ml) was added DMF (2.0 ml) followed by oxalylchloride (58.2 ml, 688 mmol) at 0° C. in drop wise fashion over the period of 30 min. After complete addition, the reaction mixture was stirred at room temperature for 3 h. Volatiles were evaporated under reduced pressure to give 2-bromo-5-iodo-benzoyl chloride (~158 g). The crude product was used for the next step immediately. (Note: The product should not be exposed to air).

Step II: To a stirred solution of 2-bromo-5-iodo-benzoyl chloride (~158 g, 457 mmol) in DCM (1500 ml) was added benzo(1,4)-dioxane (65.8 ml, 549 mmol) at 0° C. To this reaction mixture, aluminum chloride (195.4 g, 1465 mmol) was added in portions. After stirring for overnight at room temperature, reaction mixture was poured into crushed ice. This was extracted with dichloromethane (1000 ml×2). Dichloromethane layer was washed with water (1000 ml), saturated aqueous sodium bicarbonate solution (1000 ml×2), brine (1000 ml), dried over sodium sulfate, and concentrated. The solid product was triturated with hexanes. The product was dried under vacuum to give 180 g of (2-bromo-5-iodophenyl)-(2,3-dihydro-benzo[1,4]dioxin-6-yl)-methanone.

$^1$H NMR (400 MHz, DMSO-D$_6$): δ 4.29-4.37 (m, 4H), 7.02 (d, J=8.4 Hz, 1H), 7.16 (d, J=2.4 Hz, 1H), 7.18-7.19 (m, 1H), 7.53 (d, J=8.4 Hz, 1H), 7.77-7.81 (m, 1H), 7.82 (d, J=2.0 Hz, 1H).

Step III: (Note: This reaction was done in 5 lit. R. B. flask). To a stirred solution of (2-bromo-5-iodo-phenyl)-(2,3-dihydro-benzo[1,4]dioxin-6-yl)-methanone (180 g, 404.49 mmol) in trifluoroacetic acid (600 ml) was added triethylsilane (386.5 ml, 2426.9 mmol) followed by triflic acid (2.3 ml) at room temperature (note: after addition of 1 drop of triflic acid exotherm was observed so addition was done very slowly in such a way that reaction mixture refluxed gently). After stirring for 25 min at room temperature, volatiles were evaporated under reduced pressure. The resulting residue was taken in ethyl acetate (1500 ml) and washed with saturated aqueous sodium bicarbonate solution (1000 ml×2), water (1000 ml), brine (1000 ml), dried over sodium sulfate, and concentrated. The resulting residue was triturated with hexane. The residue was recrystallized from ethanol to give 147 g of 6-(2-bromo-5-iodo-benzyl)-2,3-dihydro-benzo[1,4]dioxine.

$^1$H NMR (400 MHz, DMSO-D$_6$): δ 3.90 (s, 4H), 4.2 (s, 2H), 6.65 (dd, J=8.4 Hz, J=2.0 Hz, 1H), 6.68 (d, J=2.0 Hz, 1H), 6.77 (d, J=8.4 Hz, 1H), 7.39 (d, J=8.4 Hz, 1H), 7.50 (dd, J=8.4 Hz, J=2.4 Hz, 1H), 7.67 (d, J=2.8 Hz, 1H).

EXAMPLES

Example 1

Synthesis of (2S,3R,4R,5S)-2-[4-cyclopropyl-3-(2,3-dihydro-benzo[1,4]dioxin-6-ylmethyl)-phenyl]-6-methylsulfanyl-tetrahydro-pyran-3,4,5-triol

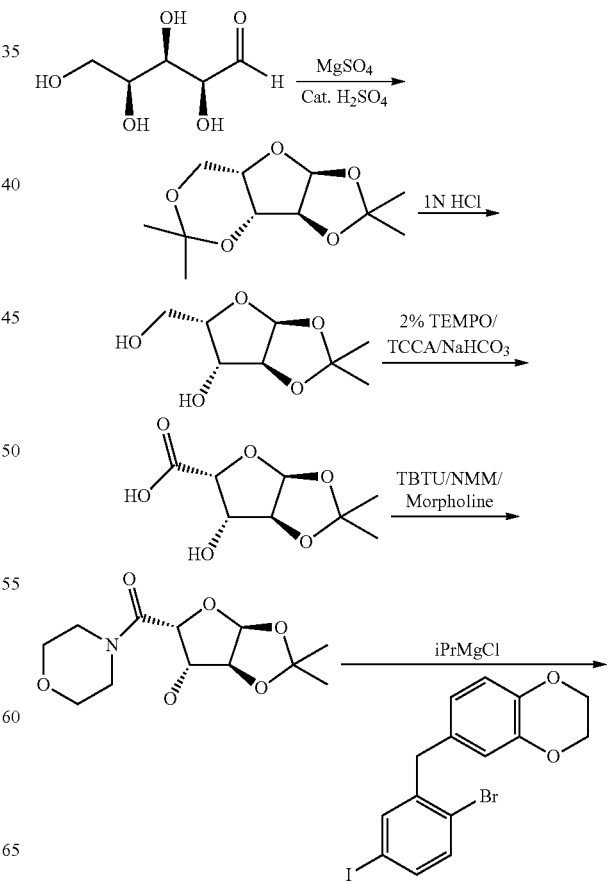

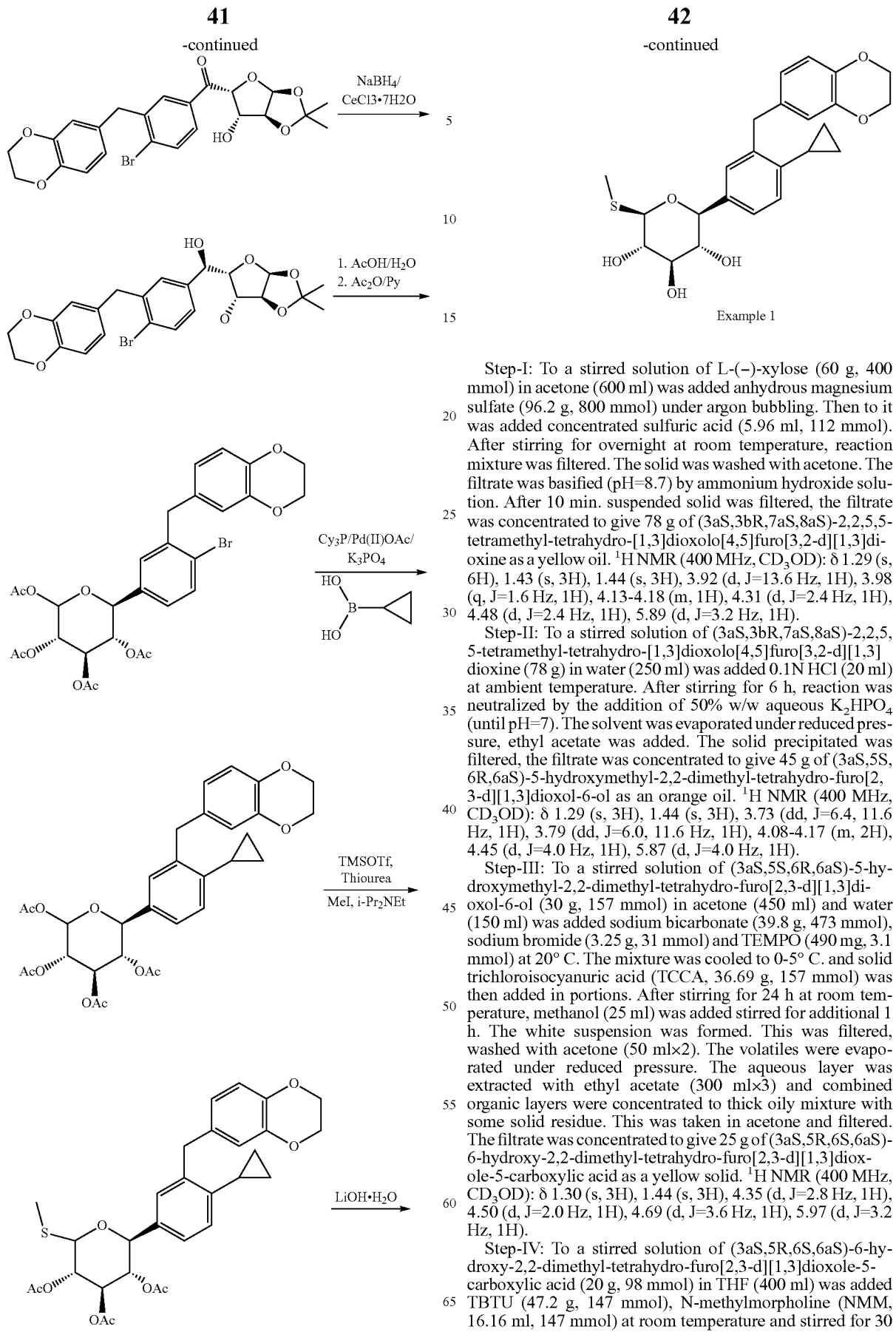

Step-I: To a stirred solution of L-(−)-xylose (60 g, 400 mmol) in acetone (600 ml) was added anhydrous magnesium sulfate (96.2 g, 800 mmol) under argon bubbling. Then to it was added concentrated sulfuric acid (5.96 ml, 112 mmol). After stirring for overnight at room temperature, reaction mixture was filtered. The solid was washed with acetone. The filtrate was basified (pH=8.7) by ammonium hydroxide solution. After 10 min. suspended solid was filtered, the filtrate was concentrated to give 78 g of (3aS,3bR,7aS,8aS)-2,2,5,5-tetramethyl-tetrahydro-[1,3]dioxolo[4,5]furo[3,2-d][1,3]dioxine as a yellow oil. $^1$H NMR (400 MHz, CD$_3$OD): δ 1.29 (s, 6H), 1.43 (s, 3H), 1.44 (s, 3H), 3.92 (d, J=13.6 Hz, 1H), 3.98 (q, J=1.6 Hz, 1H), 4.13-4.18 (m, 1H), 4.31 (d, J=2.4 Hz, 1H), 4.48 (d, J=2.4 Hz, 1H), 5.89 (d, J=3.2 Hz, 1H).

Step-II: To a stirred solution of (3aS,3bR,7aS,8aS)-2,2,5,5-tetramethyl-tetrahydro-[1,3]dioxolo[4,5]furo[3,2-d][1,3]dioxine (78 g) in water (250 ml) was added 0.1N HCl (20 ml) at ambient temperature. After stirring for 6 h, reaction was neutralized by the addition of 50% w/w aqueous K$_2$HPO$_4$ (until pH=7). The solvent was evaporated under reduced pressure. The solid precipitated was filtered, the filtrate was concentrated to give 45 g of (3aS,5S,6R,6aS)-5-hydroxymethyl-2,2-dimethyl-tetrahydro-furo[2,3-d][1,3]dioxol-6-ol as an orange oil. $^1$H NMR (400 MHz, CD$_3$OD): δ 1.29 (s, 3H), 1.44 (s, 3H), 3.73 (dd, J=6.4, 11.6 Hz, 1H), 3.79 (dd, J=6.0, 11.6 Hz, 1H), 4.08-4.17 (m, 2H), 4.45 (d, J=4.0 Hz, 1H), 5.87 (d, J=4.0 Hz, 1H).

Step-III: To a stirred solution of (3aS,5S,6R,6aS)-5-hydroxymethyl-2,2-dimethyl-tetrahydro-furo[2,3-d][1,3]dioxol-6-ol (30 g, 157 mmol) in acetone (450 ml) and water (150 ml) was added sodium bicarbonate (39.8 g, 473 mmol), sodium bromide (3.25 g, 31 mmol) and TEMPO (490 mg, 3.1 mmol) at 20° C. The mixture was cooled to 0-5° C. and solid trichloroisocyanuric acid (TCCA, 36.69 g, 157 mmol) was then added in portions. After stirring for 24 h at room temperature, methanol (25 ml) was added stirred for additional 1 h. The white suspension was formed. This was filtered, washed with acetone (50 ml×2). The volatiles were evaporated under reduced pressure. The aqueous layer was extracted with ethyl acetate (300 ml×3) and combined organic layers were concentrated to thick oily mixture with some solid residue. This was taken in acetone and filtered. The filtrate was concentrated to give 25 g of (3aS,5R,6S,6aS)-6-hydroxy-2,2-dimethyl-tetrahydro-furo[2,3-d][1,3]dioxole-5-carboxylic acid as a yellow solid. $^1$H NMR (400 MHz, CD$_3$OD): δ 1.30 (s, 3H), 1.44 (s, 3H), 4.35 (d, J=2.8 Hz, 1H), 4.50 (d, J=2.0 Hz, 1H), 4.69 (d, J=3.6 Hz, 1H), 5.97 (d, J=3.2 Hz, 1H).

Step-IV: To a stirred solution of (3aS,5R,6S,6aS)-6-hydroxy-2,2-dimethyl-tetrahydro-furo[2,3-d][1,3]dioxole-5-carboxylic acid (20 g, 98 mmol) in THF (400 ml) was added TBTU (47.2 g, 147 mmol), N-methylmorpholine (NMM, 16.16 ml, 147 mmol) at room temperature and stirred for 30 min. To it was added morpholine (12.99 ml, 147 mmol) and stirred for 6 h. The solid was filtered off by filtration and it was washed with THF. The filtrate was concentrated and resulting residue was purified by silica gel column chromatography to give 17.8 g of ((3aS,5R,6S,6aS)-6-hydroxy-2,2-dimethyl-tetrahydro-furo[2,3-d][1,3]dioxol-5-yl)-morpholin-4-yl-methanone as a white solid. $^1$H NMR (400 MHz, CD$_3$OD): δ 1.33 (s, 3H), 1.49 (s, 3H), 3.42-3.53 (m, 2H), 3.62-3.83 (m, 6H), 4.47 (d, J=2.0 Hz, 1H), 4.57 (d, J=3.6 Hz, 1H), 4.59 (d, J=2.0 Hz, 1H), 6.00 (d, J=3.2 Hz, 1H).

Step-V: To a cooled solution of ((3aS,5R,6S,6aS)-6-Hydroxy-2,2-dimethyl-tetrahydro-furo[2,3-d][1,3]dioxol-5-yl)-morpholin-4-yl-methanone (11.05 g, 256 mmol) in THF (200 ml) was added 2.0 M solution of isopropylmagnesium chloride (12.78 ml, 256 mmol) under stirring at 0° C. and stirred for additional 1.5 h. To this was added a solution of 6-(2-bromo-5-iodo-benzyl)-2,3-dihydro-benzo[1,4]dioxine (4.0 g, 146 mmol) in THF (50 ml) at 0° C. and then stirred at room temperature for 2 h. The reaction mixture was quenched by the addition of aqueous saturated ammonium chloride solution and extracted with ethyl acetate (200 ml×3). Combined organic layers were washed with brine (500 ml), dried over sodium sulfate, concentrated and purified by silica gel column chromatography to give 4.7 g of [4-bromo-3-(2,3-dihydro-benzo[1,4]dioxin-6-ylmethyl)-phenyl]-((3aS,5R,6S,6aS)-6-hydroxy-2,2-dimethyl-tetrahydro-furo[2,3-d][1,3]dioxol-5-yl)-methanone. $^1$H NMR (400 MHz, CDCl$_3$): δ 1.35 (s, 3H), 1.53 (s, 3H), 2.92 (d, J=4.0 Hz, 1H), 4.04 (d, J=3.6 Hz, 2H), 4.23 (s, 4H), 4.54 (br s, 1H), 4.56 (d, J=3.6 Hz, 1H), 5.21 (d, J=2.8 Hz, 1H), 6.05 (d, J=3.2 Hz, 1H), 6.67 (s, 2H), 6.79 (d, J=9.2 Hz, 1H), 7.68 (d, J=9.2 Hz, 1H), 7.75-7.77 (m, 2H). MS (ES) m/z 490.7 (M+1).

Step-VI: To a stirred solution of [4-bromo-3-(2,3-dihydro-benzo[1,4]dioxin-6-ylmethyl)-phenyl]-((3aS,5R,6S,6aS)-6-hydroxy-2,2-dimethyl-tetrahydro-furo[2,3-d][1,3]dioxol-5-yl)-methanone (4.7 g, 9.6 mmol) in methanol (80 ml) was added CeCl$_3$.7H$_2$O (4.27 g, 11.5 mmol) at room temperature and stirred till the solid got dissolved. Then the reaction mixture was cooled to −78° C. and sodium borohydride (434 mg, 11.5 mmol) was added in portions. After stirring for 1 h at same temperature reaction mixture was warmed up to 0° C. and quenched by the addition of saturated ammonium chloride solution. Volatiles were evaporated under reduced pressure. The aqueous layer was extracted with ethyl acetate and combined organic layers were concentrated under reduced pressure to give 5.0 g of (3aS,5S,6R,6aS)-5-{(R)-[4-bromo-3-(2,3-dihydro-benzo[1,4]dioxin-6-ylmethyl)-phenyl]-hydroxy-methyl}-2,2-dimethyl-tetrahydro-furo[2,3-d][1,3]dioxol-6-ol. The crude product was taken for the next step. MS (ES) m/z 511.8 (M+18).

A solution of (3aS,5S,6R,6aS)-5-{(R)-[4-bromo-3-(2,3-dihydro-benzo[1,4]dioxin-6-ylmethyl)-phenyl]-hydroxymethyl}-2,2-dimethyl-tetrahydro-furo[2,3-d][1,3]dioxol-6-ol (5.0 g, 10.1 mmol) in acetic acid (30 ml) and water (22 ml) was heated to 100° C. for 15 h. Reaction mixture was concentrated under reduced pressure to give 4.7 g of crude product (3S,4R,5R,6S)-6-[4-bromo-3-(2,3-dihydro-benzo[1,4]dioxin-6-ylmethyl)-phenyl]-tetrahydro-pyran-2,3,4,5-tetraol. This was used as such for next step. MS (ES) m/z 470.0 (M+18).

To a cooled solution of (3S,4R,5R,6S)-6-[4-bromo-3-(2,3-dihydro-benzo[1,4]dioxin-6-ylmethyl)-phenyl]-tetrahydro-pyran-2,3,4,5-tetraol (4.7 g, 9.9 mmol) in pyridine (20 ml) was added acetic anhydride (8.1 g, 79.5 mmol) at 0° C. After complete addition reaction mixture was stirred at room temperature for 2 h. Pyridine was evaporated under reduced pressure. The resulting residue was taken in ethyl acetate and washed with aqueous 1 N sodium bisulfate solution followed by brine, dried over sodium sulfate, concentrated to give 3.5 g of acetic acid (3S,4R,5S,6S)-3,4,5-triacetoxy-6-[4-bromo-3-(2,3-dihydro-benzo[1,4]dioxin-6-ylmethyl)-phenyl]-tetrahydro-pyran-2-yl ester.

Step-IX: To a stirred solution of acetic acid (3S,4R,5S,6S)-3,4,5-triacetoxy-6-[4-bromo-3-(2,3-dihydro-benzo[1,4]dioxin-6-ylmethyl)-phenyl]-tetrahydro-pyran-2-yl ester (2.75 g, 4.4 mmol) in toluene (25 ml) was added tricyclohexylphosphine (495 mg, 1.8 mmol), a solution of potassium phosphate tribasic (3.75 g, 1.8 mmol) in water (5 ml), cyclopropylboronic acid (1.14 g, 13.2 mmol). The reaction mixture was degassed for 45 min then added palladium (II) acetate (148 mg, 0.7 mmol). Reaction mixture was stirred at 90° C. for overnight. Reaction mixture was cooled to room temperature and was filtered through celite bed, washed with ethyl acetate (25 ml). Organic layer was washed with water (25 ml) followed by brine (25 ml), dried over sodium sulfate, concentrated and purified by column chromatography to give 1.9 g of acetic acid (3S,4R,5S,6S)-3,4,5-triacetoxy-6-[4-cyclopropyl-3-(2,3-dihydro-benzo[1,4]dioxin-6-ylmethyl)-phenyl]-tetrahydro-pyran-2-yl ester. MS (ES) m/z 600.3 (M+18).

Step-X: To a stirred solution of acetic acid (3S,4R,5S,6S)-3,4,5-triacetoxy-6-[4-cyclopropyl-3-(2,3-dihydro-benzo[1,4]dioxin-6-ylmethyl)-phenyl]-tetrahydro-pyran-2-yl ester (1.9 g, 3.3 mmol) in dioxane (8 ml) was added thiourea followed by trimethylsilyl trifluoromethane sulfonate (0.88 ml, 4.8 mmol). The reaction mixture was heated to 80° C. for 3 h. Reaction mixture was cooled to room temperature and added methyl iodide (0.52 ml, 8.1 mmol) followed by diisopropylethyl amine (2.79 ml, 16.2 mmol) and stirred for additional 3 h. Reaction mixture was diluted with ethyl acetate (40 ml) and washed with water (40 ml). The organic layer was concentrated. The resulting residue was taken in methanol (10 ml) and heated to 60° C. for 2 h, then cooled to 0° C. and stirred for additional 1 h. The resulting solid was filtered and washed with methanol to give 750 mg of acetic acid (3S,4R,5S,6S)-4,5-diacetoxy-6-[4-cyclopropyl-3-(2,3-dihydro-benzo[1,4]dioxin-6-ylmethyl)-phenyl]-2-methylsulfanyl-tetrahydro-pyran-3-yl ester. $^1$H NMR (400 MHz, DMSO-d$_6$): δ 0.55-0.59 (m, 2H), 0.85 (d, J=8.8 Hz, 2H), 1.70 (s, 3H), 1.82-1.89 (m, 1H), 1.93 (s, 3H), 2.03 (s, 3H), 2.08 (s, 3H), 3.95 (d, J=15.2 Hz, 1H), 4.02 (d, J=16.8 Hz, 1H), 4.00 (s, 4H), 4.65 (d, J=10.0 Hz, 1H), 4.87 (d, J=10.0 Hz, 1H), 5.03-5.12 (m, 2H), 5.34 (t, J=10.0 Hz, 1H), 6.58-6.60 (m, 2H), 6.73 (d, J=7.6 Hz, 1H), 6.91 (d, J=8.0 Hz, 1H), 7.04 (d, J=8.0 Hz, 1H), 7.15 (d, J=8.0 Hz, 1H). MS (ES) m/z 588.3 (M+18).

Step-XI: To a stirred solution of acetic acid (3S,4R,5S,6S)-4,5-diacetoxy-6-[4-cyclopropyl-3-(2,3-dihydro-benzo[1,4]dioxin-6-ylmethyl)-phenyl]-2-methylsulfanyl-tetrahydro-pyran-3-yl ester (80 mg, 0.14 mmol) in methanol:THF:water (3:2:1 mixture, 6 ml) was added lithium hydroxide (9 mg, 0.4 mmol). After stirring for 2 h at room temperature, volatiles were evaporated under reduced pressure. The resulting residue was taken in ethyl acetate (10 ml) and washed with brine (5 ml), brine containing 1 ml of 5% aqueous KHSO$_4$ (5 ml), brine (5 ml), dried over sodium sulfate, concentrated and purified by preparative HPLC to furnish 55 mg of (2S,3R,4R,5S)-2-[4-cyclopropyl-3-(2,3-dihydro-benzo[1,4]dioxin-6-ylmethyl)-phenyl]-6-methylsulfanyl-tetrahydro-pyran-3,4,5-triol. $^1$H NMR (400 MHz, CD$_3$OD): δ 0.52-0.60 (m, 2H), 0.80-0.90 (m, 2H), 1.78-1.88 (m, 1H), 2.15 (s, 3H), 3.32-3.35 (m, 3H), 4.05 (q, J=15.2 Hz, 2H), 4.11 (d, J=8.8 Hz, 1H), 4.17 (s, 4H), 4.38 (d, J=10 Hz, 1H), 6.61 (d, J=8.0 Hz, 2H), 6.69 (d, J=8.4 Hz, 1H), 6.98 (d, J=8.0 Hz, 1H), 7.15 (d, J=7.6 Hz, 1H), 7.17 (d, J=8.0 Hz, 1H). MS (ES) m/z 462.3 (M+18).

Following examples were prepared by using the procedures described for Example 1 and the appropriate starting materials.

| Ex. No. | Structure/IUPAC name | Spectral data |
|---|---|---|
| 1-1 | 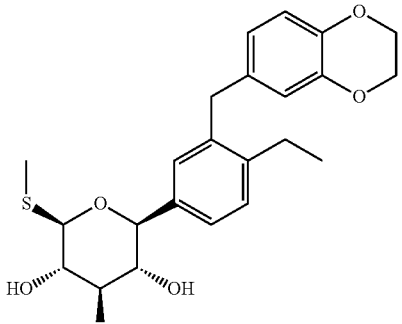<br>(2S,3R,4R,5S,6R)-2-[3-(2,3-Dihydro-benzo[1,4]dioxin-6-ylmethyl)-4-ethyl-phenyl]-6-methylsulfanyl-tetrahydro-pyran-3,4,5-triol | $^1$H NMR (400 MHz, CD$_3$OD): δ 1.08 (t, J = 7.6 Hz, 3H), 2.13 (s, 3H), 2.59 (q, J = 7.6 Hz, 2H), 3.32-3.50 (m, 3H), 3.89 (s, 2H), 4.12 (d, J = 9.2 Hz, 1H), 4.17 (s, 4H), 4.38 (d, J = 9.6 Hz, 1H), 6.57 (d, J = 9.6 Hz, 2H), 6.68 (d, J = 8.0 Hz, 1H), 7.12-7.22 (m, 3H). MS (ES) m/z 450.2 (M + 18). |
| 1-2 | 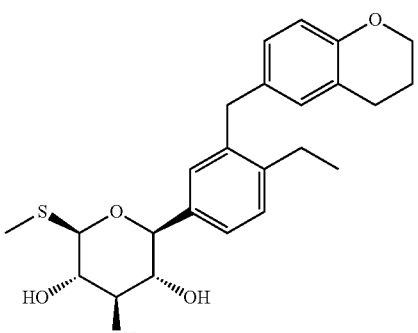<br>(2S,3R,4R,5S,6R)-2-(3-Chroman-6-ylmethyl-4ethyl-phenyl)-6-methylsulfanyl-tetrahydro-pyran-3,4,5-triol | $^1$H NMR (400 MHz, CD$_3$OD): δ 1.08 (t, J = 7.8 Hz, 3H), 1.92-1.96 (m, J = 5.6 Hz, 2H), 2.13 (s, 3H), 2.6 (q, J = 7.8 Hz, 2H), 2.70 (t, J = 6.4 Hz, 2H), 3.34-3.47 (m, 3H), 3.90 (s, 2H), 4.08-4.13 (m, 3H), 4.38 (d, J = 9.6 Hz, 1H), 6.59 (d, J = 8.4 Hz, 1H), 6.78-6.81 (m, 2H), 7.13-7.21 (m, 3H). MS (ES) m/z 448.3 (M + 18). |
| 1-3 | 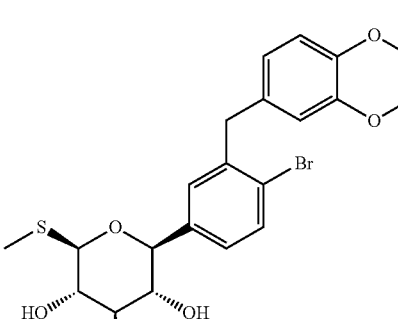<br>(2S,3R,4R,5S,6R)-2-[4-Bromo-3-(2,3-dihydro-benzo[1,4]dioxin-6-ylmethyl)-phenyl]-6-methylsulfanyl-tetrahydro-pyran-3,4,5-triol | $^1$H NMR (400 MHz, CD$_3$OD): δ 2.12 (s, 3H), 3.30-3.44 (m, 3H), 3.96-4.02 (m, 2H), 4.12 (d, J = 9.8 Hz, 1H), 4.18 (s, 4H), 4.38 (d, J = 9.3 Hz, 1H), 6.68 (s, 2H), 6.71 (d, J = 8.4 Hz, 1H), 7.16 (d, J = 8.4 Hz, 1H), 7.24 (s, 1H), 7.54 (d, J = 7.8 Hz, 1H). MS (ES) m/z 501 (M + 18). |

| Ex. No. | Structure/IUPAC name | Spectral data |
|---|---|---|
| 1-4 | 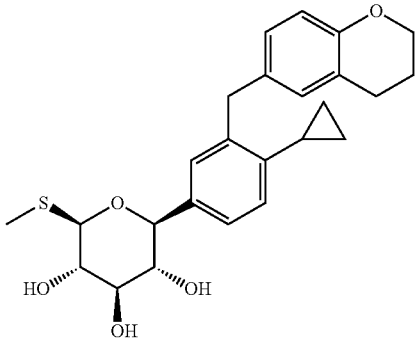<br>(2S,3R,4R,5S,6R)-2-(3-Chroman-6-ylmethyl-4-cyclopropyl-phenyl)-6-methylsulfanyl-tetrahydro-pyran-3,4,5-triol | $^1$H NMR (400 MHz, CDCl$_3$): δ 0.52-0.68 (m, 2H), 0.80-0.95 (m, 2H), 1.78-1.90 (m, 1H), 1.92-2.12 (m, 3H), 2.18 (s, 3H), 2.71 (t, J = 5.6 Hz, 2H), 3.56 (t, J = 8.8 Hz, 2H), 3.70 (t, J = 8.8 Hz, 1H), 4.07 (q, J = 15.6 Hz, 2H), 4.12-4.22 (m, 2H), 4.38 (d, J = 9.2 Hz, 1H), 6.69 (d, J = 7.4 Hz, 1H), 6.80 (s, 1H), 6.85 (d, J = 8.0 Hz, 1H), 7.01 (d, J = 7.6 Hz, 1H), 7.10 (s, 1H), 7.18 (d, J = 7.6 Hz, 1H). MS (ES) m/z 460.2 (M +18). |
| 1-5 | 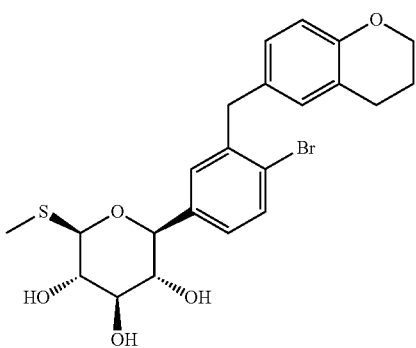<br>(2S,3R,4R,5S,6R)-2-(4-Bromo-3-chroman-6-ylmethyl-phenyl)-6-methylsulfanyl-tetrahydro-pyran-3,4,5-triol | $^1$H NMR (400 MHz, CDCl$_3$): δ 1.95-2.02 (m, 2H), 2.17 (s, 3H), 2.73 (t, J = 6.4 Hz, 2H), 3.46-3.60 (m, 2H), 3.67 (t, J = 8.8 Hz, 1H), 3.99 (q, J = 16 Hz, 2H), 4.10-4.22 (m, 3H), 4.37 (d, J = 9.6 Hz, 1H), 6.70 (d, J = 8.4 Hz, 1H), 6.85 (s, 1H), 6.89 (d, J = 8.0 Hz, 1H), 7.10-7.20 (m, 2H), 7.56 (d, J = 8.0 Hz, 1H). MS (ES) m/z 499 (M + 18). |
| 1-6 | 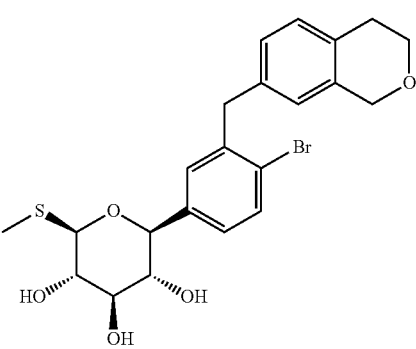<br>(2S,3R,4R,5S,6R)-2-(4-Bromo-3-isochroman-7-ylmethyl-phenyl)-6-methylsulfanyl-tetrahydro-pyran-3,4,5-triol | $^1$H NMR (400 MHz, CD3OD): δ 2.12 (s, 3H), 2.75-2.85 (m, 2H), 3.20-3.55 (m, 3H), 3.93 (t, J = 5.2 Hz, 2H), 4.05 (s, 2H), 4.12 (d, J = 9.2 Hz, 1H), 4.38 (d, J = 9.2 Hz, 1H), 4.68 (s, 2H), 6.38 (s, 1H), 6.95-7.08 (m, 2H), 7.17 (d, J = 8.4 Hz, 1H), 7.24 (s, 1H), 7.54 (d, J = 7.6 Hz, 1H). MS (ES) m/z 500.1 (M + 18). |

| Ex. No. | Structure/IUPAC name | Spectral data |
|---|---|---|
| 1-7 | 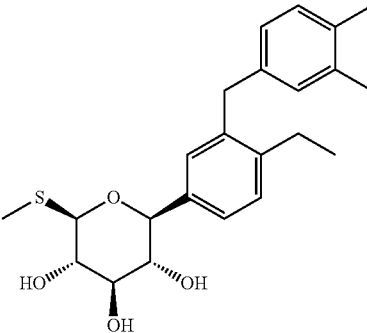<br>(2S,3R,4R,5S,6R)-2-(4-Ethyl-3-isochroman-7-ylmethyl-phenyl)-6-methylsulfanyl-tetrahydro-pyran-3,4,5-triol | $^1$H NMR (400 MHz, CD$_3$OD): δ 1.08 (t, J = 7.2 Hz, 3H), 2.13 (s, 3H), 2.59 (q, J = 7.6 Hz, 2H), 2.75-2.82 (m, 2H), 3.30-3.50 (m, 3H), 3.92 (t, J = 6.0 Hz, 2H), 3.97 (s, 2H), 4.12 (d, J = 8.8 Hz, 1H), 4.38 (d, J = 9.2 Hz, 1H), 4.65 (s, 2H), 6.77 (s, 1H), 6.94 (d, J = 7.6 Hz, 1H), 7.00 (d, J = 8.0 Hz, 1H), 7.12-7.26 (m, 3H). MS (ES) m/z 448.2 (M + 18). |

Example 2

Synthesis of (2S,3R,4R,5S)-2-[4-Cyclopropyl-3-(2,3-dihydro-benzo[1,4]dioxin-6-ylmethyl)-phenyl]-6-methanesulfonyl-tetrahydro-pyran-3,4,5-triol

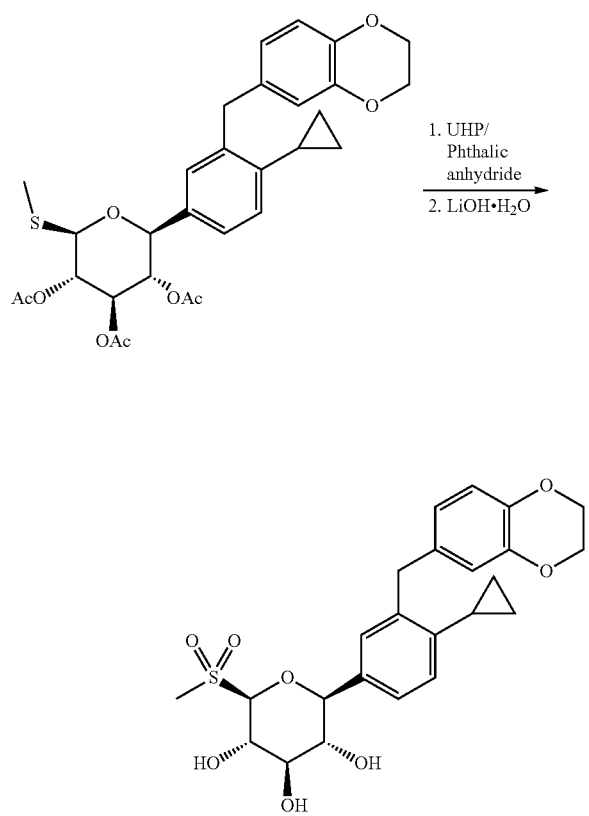

Example 2

Step-I: A mixture of urea hydrogen peroxide (297 mg, 3.1 mmol) and phthalic anhydride (233 mg, 1.5 mmol) were taken in acetonitrile (3 ml) and stirred until the solids were dissolved. To this was added a solution of acetic acid (2R,3S,4R,5S,6S)-4,5-diacetoxy-6-[4-cyclopropyl-3-(2,3-dihydro-benzo[1,4]dioxin-6-ylmethyl)-phenyl]-2-methylsulfanyl-tetrahydro-pyran-3-yl ester (300 mg, 0.5 mmol) in acetonitrile (2 ml) and stirred at ambient temperature for 7 h. Reaction mixture was diluted with ethyl acetate (10 ml), washed with saturated sodium bicarbonate (10 ml), water (10 ml), dried over sodium sulfate, concentrated to give 310 mg of acetic acid (2R,3S,4R,5S,6S)-4,5-diacetoxy-6-[4-cyclopropyl-3-(2,3-dihydro-benzo[1,4]dioxin-6-ylmethyl)-phenyl]-2-methanesulfonyl-tetrahydro-pyran-3-yl ester as a white solid. MS (ES) m/z 620.2 (M+18).

To a stirred solution of acetic acid (2R,3S,4R,5S,6S)-4,5-diacetoxy-6-[4-cyclopropyl-3-(2,3-dihydro-benzo[1,4]dioxin-6-ylmethyl)-phenyl]-2-methanesulfonyl-tetrahydro-pyran-3-yl (350 mg, 0.58 mmol) in methanol:THF:water (3:2:1 mixture, 12 ml) was added lithium hydroxide (36 mg, 0.9 mmol). After stirring for 2 h at room temperature, volatiles were evaporated under reduced pressure. The resulting residue was taken in ethyl acetate (10 ml) and washed with brine (5 ml), brine containing 1 ml of 5% aqueous KHSO$_4$ (5 ml), brine (5 ml), dried over sodium sulfate, concentrated and purified by preparative HPLC to furnish 240 mg of (2S,3R,4R,5S)-2-[4-cyclopropyl-3-(2,3-dihydro-benzo[1,4]dioxin-6-ylmethyl)-phenyl]-6-methylsulfanyl-tetrahydro-pyran-3,4,5-triol. $^1$H NMR (400 MHz, CD$_3$OD): δ 0.52-0.62 (m, 2H), 0.82-0.91 (m, 2H), 1.80-1.90 (m, 1H), 2.92 (s, 3H), 3.40 (t, J=9.6 Hz, 1H), 3.55 (t, J=8.8 Hz, 1H), 3.88 (t, J=9.2 Hz, 1H), 4.05 (s, 2H), 4.17 (s, 4H), 4.27 (d, J=9.2 Hz, 1H), 4.52 (d, J=9.6 Hz, 1H), 6.60 (dd, J=8.0, 2.4 Hz, 2H), 6.69 (d, J=8.4 Hz, 1H), 6.99 (d, J=8.0 Hz, 1H), 7.16 (d, J=2.4 Hz, 1H), 7.18 (dd, J=8.0, 1.6 Hz, 1H).

MS (ES) m/z 494.2 (M+18).

Following examples were prepared by using the procedures described for Example 2 and the appropriate starting materials.

| Ex. No. | Structure/IUPAC name | Spectral data |
| --- | --- | --- |
| 2-1 | (2S,3R,4R,5S,6R)-2-[3-(2,3-Dihydro-benzo[1,4]dioxin-6-ylmethyl)-4-ethyl-phenyl]-6-methanesulfonyl-tetrahydro-pyran-3,4,5-triol | $^1$H NMR (400 MHz, CD$_3$OD): δ 1.09 (t, J = 8.8 Hz, 3H), 2.60 (q, J = 7.4 Hz, 2H), 2.92 (s, 3H), 3.42 (t, J = 9.3 Hz, 1H), 3.55 (t, J = 8.8 Hz, 1H), 3.87-3.91 (m, 3H), 4.20 (s, 4H), 4.26 (d, J = 10 Hz, 1H), 4.53 (d, J = 9.6 Hz, 1H), 6.55-6.58 (m, 2H), 6.72 (d, J = 8.0 Hz, 1H), 7.14 (s, 1H), 7.17-7.24 (m, 2H). MS (ES) m/z 482.3 (M + 18). |
| 2-2 | (2S,3R,4R,5S,6R)-2-(3-Chroman-6-ylmethyl-4-ethyl-phenyl)-6-methanesulfonyl-tetrahydro-pyran-3,4,5-triol | $^1$H NMR (400 MHz, CD$_3$OD): δ 1.09 (t, J = 7.8 Hz, 3H), 1.92-195 (m, 2H), 2.63 (q, J = 7.3 Hz, 2H), 2.69 (t, J = 6.4 Hz, 2H), 2.92 (s, 3H), 3.41 (t, J = 9.8 Hz, 1H), 3.55 (t, J = 9.3 Hz, 1H), 3.86-3.90 (m, 3H), 4.10 (t, J = 9.8 Hz, 2H), 4.27 (d, J = 9.8 Hz, 1H), 4.52 (d, J = 9.8 Hz, 1H), 6.58 (d, J = 7.8 Hz, 1H), 6.78-6.80 (m, 2H), 7.14 (s, 1H), 7.17-7.23 (m, 2H). MS (ES) m/z 480.3 (M + 18). |
| 2-3 | (2S,3R,4R,5S,6R)-2-[4-Bromo-3-(2,3-dihydro-benzo[1,4]dioxin-6-ylmethyl)-phenyl]-6-methanesulfonyl-tetrahydro-pyran-3,4,5-triol | $^1$H NMR (400 MHz, CD$_3$OD): δ 2.92 (s, 3H), 3.31-3.35 (m, 1H), 3.56 (t, J = 9.6 Hz, 1H), 3.90 (t, J = 9.2 Hz, 1H), 3.98 (s, 2H), 4.19 (s, 4H), 4.28 (d, J = 9.6 Hz, 1H), 4.52 (d, J = 9.6 Hz, 1H), 6.63-6.65 (m, 2H), 6.72 (d, J = 8.3 Hz, 1H), 7.18 (d, J = 7.6 Hz, 1H), 7.24 (s, 1H), 7.56 (d, J = 8.3 Hz, 1H). MS (ES) m/z 534.2 (M + 18). |

| Ex. No. | Structure/IUPAC name | Spectral data |
|---|---|---|
| 2-4 | 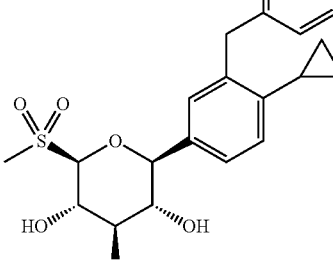<br>(2S,3R,4R,5S,6R)-2-(3-Chroman-6-ylmethyl-4-cyclopropyl-phenyl)-6-methanesulfonyl-tetrahydro-pyran-3,4,5-triol | $^1$H NMR (400 MHz, CDCl$_3$): δ 0.58-0.70 (m, 2H), 0.85-0.95 (m, 2H), 1.80-1.92 (m, 1H), 1.92-2.2 (m, 2H), 2.72 (t, J = 5.6 Hz, 2H), 2.89 (s, 3H), 3.59 (t, J = 8.8 Hz, 1H), 3.79 (t, J = 8.8 Hz, 1H), 4.0-4.12 (m, 3H), 4.15 (t, J = 5.6 Hz, 2H), 4.27 (d, J = 9.6 Hz, 1H), 4.38 (d, J = 10.0 Hz, 1H), 6.68 (d, J = 8.4 Hz, 1H), 6.78-6.88 (m, 2H), 6.98-7.08 (m, 2H), 7.16 (d, J = 7.6 Hz, 1H). MS (ES) m/z 492.3 (M + 18). |
| 2-5 | 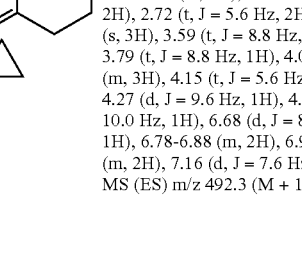<br>(2S,3R,4R,5S,6R)-2-(4-Bromo-3-chroman-6-ylmethyl-phenyl)-6-methanesulfonyl-tetrahydro-pyran-3,4,5-triol | $^1$H NMR (400 MHz, CD3OD): δ 1.90-2.02 (m, 2H), 2.71 (t, J = 6 Hz, 2H), 2.90 (s, 3H), 3.20-3.40 (m, 1H), 3.54 (t, J = 8.8 Hz, 1H), 3.87 (t, J = 9.2 Hz, 1H), 3.98 (s, 2H), 4.11 (t, J = 4.8 Hz, 2H), 4.28 (d, J = 9.6 Hz, 1H), 4.52 (d, J = 9.6 Hz, 1H), 6.61 (d, J = 8.4 Hz, 1H), 6.86 (d, J = 7.6 Hz, 2H), 7.17 (d, J = 7.6 Hz, 1H), 7.22 (s, 1H), 7.55 (d, J = 8.4 Hz, 1H). MS (ES) m/z 530.2 (M + 18). |

Example 3

Synthesis of (2S,3R,4R,5S,6S)-2-[4-Cyclopropyl-3-(2,3-dihydro-benzo[1,4]dioxin-6-ylmethyl)-phenyl]-6-methoxy-tetrahydro-pyran-3,4,5-triol

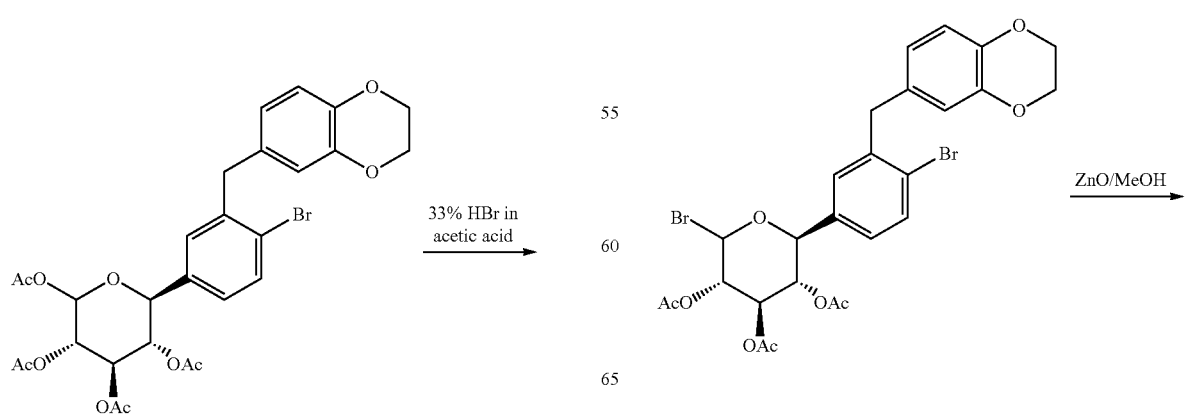

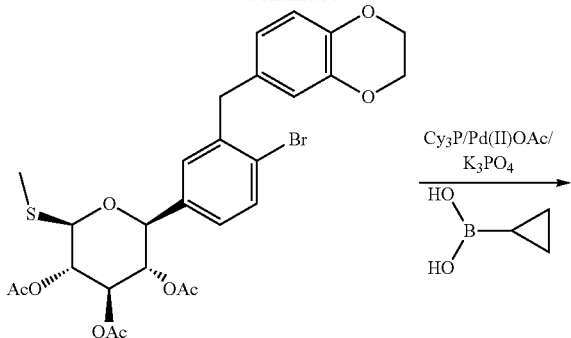

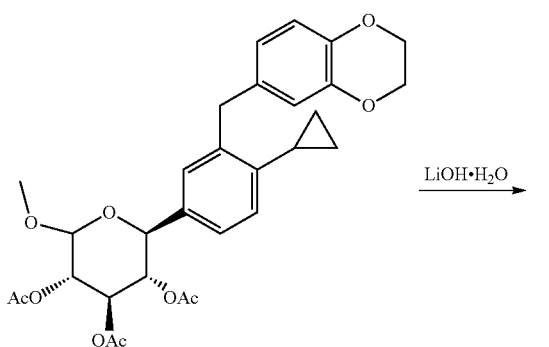

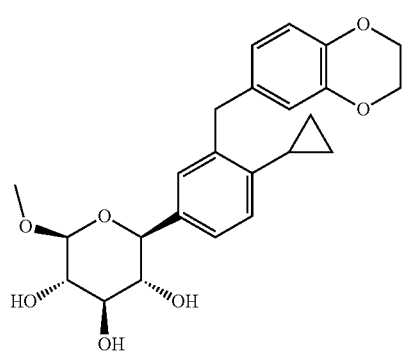

Example 3

Step-I: Acetic acid (3S,4R,5S,6S)-3,4,5-triacetoxy-6-[4-bromo-3-(2,3-dihydro-benzo[1,4]dioxin-6-ylmethyl)-phenyl]-tetrahydro-pyran-2-yl ester (3.5 g) was taken in 33% HBr in acetic acid (10 ml) and stirred for 1 h at room temperature. To this was added dichloromethane (20 ml) and stirred for additional 30 min. This was diluted with dichloromethane (50 ml), poured into crushed ice and neutralized with sodium bicarbonate. Organic layer was separated, extracted with DCM (50 ml×2), combined organic layers were washed with water (200 ml×2), brine (200 ml), dried over sodium sulfate, concentrated to give 3.0 g of acetic acid (3S,4R,5S,6S)-4,5-diacetoxy-2-bromo-6-[4-bromo-3-(2,3-dihydro-benzo[1,4]dioxin-6-ylmethyl)-phenyl]-tetrahydro-pyran-3-yl ester.

Step-II: To a stirred solution of acetic acid (3S,4R,5S,6S)-4,5-diacetoxy-2-bromo-6-[4-bromo-3-(2,3-dihydro-benzo[1,4]dioxin-6-ylmethyl)-phenyl]-tetrahydro-pyran-3-yl ester (2.5 g, 3.89 mmol) in methanol (38 ml) was added zinc oxide (429 mg, 4.6 mmol) at room temperature. Then the reaction mixture was refluxed for 1.5 h. Reaction mixture was cooled to room temperature, filtered through celite bed, filtrate was concentrated and purified by column chromatography to give 1.8 g of acetic acid (3S,4R,5S,6S)-4,5-diacetoxy-6-[4-bromo-3-(2,3-dihydro-benzo[1,4]dioxin-6-ylmethyl)-phenyl]-2-methoxy-tetrahydro-pyran-3-yl ester as a yellow solid.

Step-III: To a stirred solution of acetic acid (3S,4R,5S,6S)-4,5-diacetoxy-6-[4-bromo-3-(2,3-dihydro-benzo[1,4]dioxin-6-ylmethyl)-phenyl]-2-methoxy-tetrahydro-pyran-3-yl ester (700 mg, 1.18 mmol) in toluene (11 ml) was added tricyclohexylphosphine (132 mg, 0.47 mmol), a solution of potassium phosphate tribasic (1.0 g, 4.72 mmol) in water (1 ml), ethylboronic acid (262 mg, 3.54 mmol). The reaction mixture was degassed for 40 min then added palladium (II) acetate (39 mg, 0.18 mmol). Reaction mixture was stirred at 90° C. for overnight. Reaction mixture was cooled to room temperature and was filtered through celite bed, washed with ethyl acetate (10 ml). Organic layer was washed with water (15 ml) followed by brine (15 ml), dried over sodium sulfate, concentrated and purified by column chromatography to give 320 mg of acetic acid (3S,4R,5S,6S)-4,5-diacetoxy-6-[3-(2,3-dihydro-benzo[1,4]dioxin-6-ylmethyl)-4-ethyl-phenyl]-2-methoxy-tetrahydro-pyran-3-yl ester as white solid.

Step-IV: To a stirred solution of acetic acid (3S,4R,5S,6S)-4,5-diacetoxy-6-[3-(2,3-dihydro-benzo[1,4]dioxin-6-ylmethyl)-4-ethyl-phenyl]-2-methoxy-tetrahydro-pyran-3-yl ester (300 mg, 0.55 mmol) in methanol:THF:water (3:2:1 mixture, 6 ml) was added lithium hydroxide (46 mg, 1.10 mmol). After stirring for 2 h at room temperature, volatiles were evaporated under reduced pressure. The resulting residue was taken in ethyl acetate (10 ml) and washed with brine (5 ml), brine containing 1 ml of 5% aqueous $KHSO_4$ (5 ml), brine (5 ml), dried over sodium sulfate, concentrated and purified by preparative HPLC to furnish 90 mg (2S,3R,4R,5S,6S)-2-[3-(2,3-dihydro-benzo[1,4]dioxin-6-ylmethyl)-4-ethyl-phenyl]-6-methoxy-tetrahydro-pyran-3,4,5-triol as white solid. $^1$H NMR (400 MHz, $CD_3OD$): δ 0.56-0.58 (m, 2H), 0.84-0.87 (m, 2H), 1.80-1.85 (m, 1H), 3.27-3.44 (m, 3H), 3.48 (s, 3H), 4.05 (d, J=6.4 Hz, 2H), 4.10 (d, J=9.3 Hz, 1H), 4.17 (s, 4H), 4.30 (d, J=7.8 Hz, 1H), 6.62 (d, J=8.4 Hz, 1H), 6.69 (d, J=8.4 Hz, 2H), 6.98 (d, J=7.8 Hz, 1H), 7.16-7.19 (m, 2H). MS (ES) m/z 446.3 (M+18).

Following examples were prepared by using the procedures described for Example 3 and the appropriate starting materials.

| Ex. No. | Structure/IUPAC name | Spectral data |
|---|---|---|
| 3-1 | 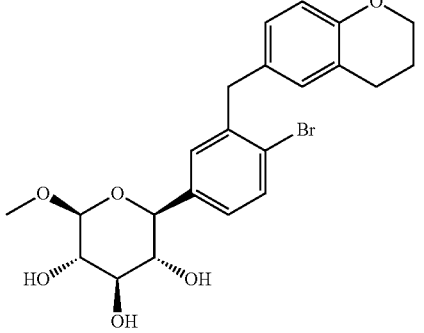<br>(2S,3R,4R,5S,6S)-2-(4-Bromo-3-chroman-6-ylmethyl-phenyl)-6-methoxy-tetrahydro-pyran-3,4,5-triol | $^1$H NMR (400 MHz, CD$_3$OD): δ 1.91-1.97 (m, 2H), 2.71 (t, J = 6.4 Hz, 2H), 3.25-3.30 (m, 2H), 3.38-3.45 (m, 1H), 3.47 (s, 3H), 3.98 (d, J = 6 Hz, 2H), 4.09-4.11 (m, 3H), 4.29 (d, J = 7.8 Hz, 1H), 6.60 (d, J = 7.8 Hz, 1H), 6.85-6.88 (m, 2H), 7.15 (dd, J = 8.5, 2.4 Hz, 1H), 7.23 (d, J = 1.9 Hz, 1H). 7.23 (d, J = 8.3 Hz, 1H). MS (ES) m/z 483.3 (M + 18). |
| 3-2 | 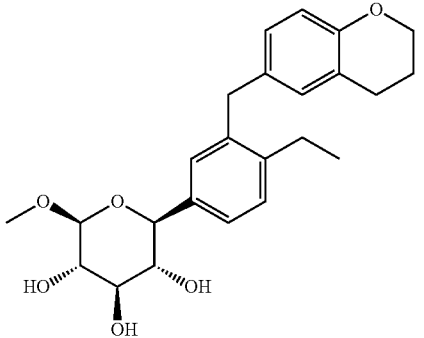<br>(2S,3R,4R,5S,6S)-2-(3-Chroman-6-ylmethyl-4-ethyl-phenyl)-6-methoxy-tetrahydro-pyran-3,4,5-triol | $^1$H NMR (400 MHz, CD$_3$OD): δ 1.08 (t, J = 6.3 Hz, 3H), 1.92-1.96 (m, 2H), 2.59 (q, J = 7.4 Hz, 2H), 2.69 (t, J = 6.4 Hz, 2H), 3.28-3.47 (m, 3H), 3.48 (s, 3H), 3.82-3.93 (m, 2H), 4.08-4.12 (m, 3H), 4.30 (d, J = 7.8 Hz, 1H), 6.59 (d, J = 7.8 Hz, 1H), 6.80 (d, J = 10.3 Hz, 2H), 7.15-7.22 (m, 3H). MS (ES) m/z 432.4 (M + 18). |
| 3-3 | 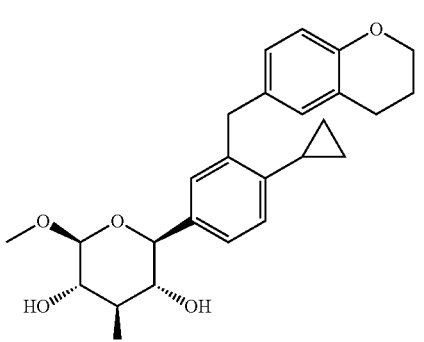<br>(2S,3R,4R,5S,6S)-2-(3-Chroman-6-ylmethyl-4-cyclopropyl-phenyl)-6-methoxy-tetrahydro-pyran-3,4,5-triol | $^1$H NMR (400 MHz, CD$_3$OD): δ 0.54-0.58 (m, 2H), 0.82-0.87 (m, 2H), 1.83-184 (m, 1H), 1.92-1.97 (m, 2H), 2.70 (t, J = 6.4 Hz, 2H), 3.27-3.44 (m, 3H), 3.47 (s, 3H), 4.05-4.11 (m, 5H), 4.29 (d, J = 7.8 Hz, 1H), 6.59 (d, J = 8.4 Hz, 1H), 6.69 (d, J = 8.4 Hz, 2H), 6.98 (d, J = 7.8 Hz, 1H), 7.15-7.18 (m, 2H). MS (ES) m/z 444.3 (M + 18). |

| Ex. No. | Structure/IUPAC name | Spectral data |
|---|---|---|
| 3-4 | 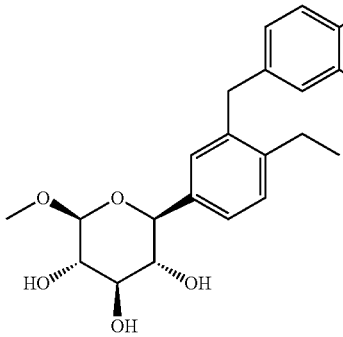<br>(2S,3R,4R,5S,6S)-2-[3-(2,3-Dihydro-benzo[1,4]dioxin-6-ylmethyl)-4-ethyl-phenyl]-6-methoxy-tetrahydro-pyran-3,4,5-triol | $^1$H NMR (400 MHz, CD$_3$OD): δ 1.08 (t, J = 6.3 Hz, 3H), 2.59 (q, J = 7.4 Hz, 2H), 3.35-3.48 (m, 6H), 4.90 (d, J = 2.5 Hz, 2H), 4.11 (d, J = 9.3 Hz, 1H), 4.17 (s, 4H), 4.30 (d, J = 7.8 Hz, 1H), 6.55-6.69 (m, 2H), 6.68 (d, J = 8.4 Hz, 1H), 7.15-7.23 (m, 3H). MS (ES) m/z 434.4 (M + 18). |

Example 4

Synthesis of N-[(3S,4R,5R,6S)-6-(3-chroman-6-ylmethyl-4-ethyl-phenyl)-3,4,5-trihydroxy-tetrahydro-pyran-2-yl]-N-propyl-acetamide

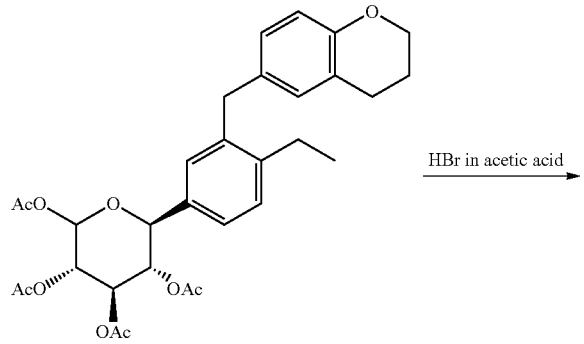

HBr in acetic acid →

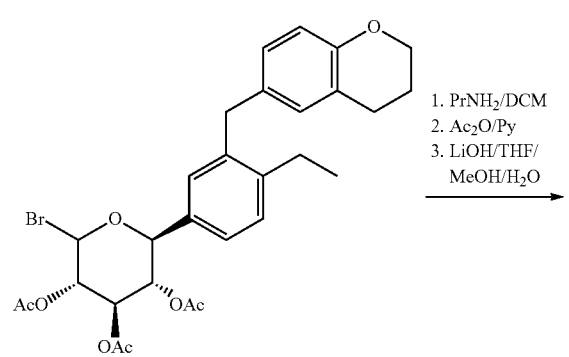

1. PrNH$_2$/DCM
2. Ac$_2$O/Py
3. LiOH/THF/MeOH/H$_2$O
→

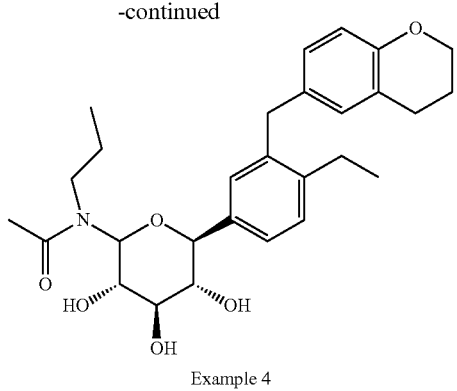

Example 4

Step-I: Acetic acid (3S,4R,5S,6S)-3,4,5-triacetoxy-6-(3-chroman-6-ylmethyl-4-ethyl-phenyl)-tetrahydro-pyran-2-yl ester (300 mg) was taken in 33% HBr in acetic acid (1.2 ml) and stirred for 1 h at room temperature. To this was added dichloromethane (2 ml) and stirred for additional 30 min. This was diluted with dichloromethane (5 ml), poured into crushed ice and neutralized with sodium bicarbonate. Organic layer was separated, extracted with DCM (8 ml×2), combined organic layers were washed with water (10 ml×2), brine (10 ml), dried over sodium sulfate, concentrated to give 250 mg of acetic acid (3S,4R,5S,6S)-4,5-diacetoxy-2-bromo-6-(3-chroman-6-ylmethyl-4-ethyl-phenyl)-tetrahydro-pyran-3-yl ester.

Step-II: To a stirred solution of acetic acid (3S,4R,5S,6S)-4,5-diacetoxy-2-bromo-6-(3-chroman-6-ylmethyl-4-ethyl-phenyl)-tetrahydro-pyran-3-yl ester (250 mg, 0.4 mmol) in DCM (2 ml) was added propyl amine (0.4 ml) and stirred for 1.5 h at 40° C. Then it was cooled to room temperature and added pyridine (0.3 ml, 3.39 mmol), acetic anhydride (0.3 ml, 3.39 mmol), stirred for overnight. Volatiles were evaporated under reduced pressure, resulting residue was taken in DCM and was with 1N HCl (2 ml), brine, dried over sodium sulfate and concentrated to give 170 mg of solid. The resulting solid (170 mg, 0.3 mmol) was taken in methanol:water:THF (1:1:3, 5 ml) mixture and added lithium hydroxide monohydrate (24 mg, 0.6 mmol) at room temperature and stirred for 2.5 h. Volatiles were evaporated and resulting solid was taken in ethyl acetate and washed with, brine (2 ml), a mixture of 5% KHSO$_4$ solution in brine (2 ml), dried over sodium sulfate, concentrated and purified by preparative HPLC to give 13 mg of N-[(3S,4R,5R,6S)-6-(3-chroman-6-ylmethyl-4-ethyl-phenyl)-3,4,5-trihydroxy-tetrahydro-pyran-2-yl]-N-propyl-acetamide. ¹H NMR (400 MHz, CD₃OD): δ 0.86 (t, J=7.2 Hz, 3H), 1.06-1.11 (m, 3H), 1.56-1.64 (m, 2H), 1.93 (qui, J=6.4 Hz, 2H), 2.17 (s, 3H), 2.57-2.63 (m, 2H), 2.68 (t, J=6.4 Hz, 2H), 3.00-3.17 (m, 1H), 3.33-3.36 (m, 1H), 3.50-3.63 (m, 3H), 3.89 (s, 2H), 4.10 (t, J=4.8 Hz, 2H), 4.15-4.23 (m, 1H), 4.95 (d, J=8.8 Hz, 1H), 6.58 (d, J=8.4 Hz, 1H), 6.75-6.80 (m, 2H), 7.12-7.16 (m, 3H). MS (ES) m/z 484.3 (M+1).

The following examples could be prepared using the procedures described in Examples 1-4 and the appropriate starting materials.

| Ex. No. | Structure | Name |
|---------|-----------|------|
| 5-1 | 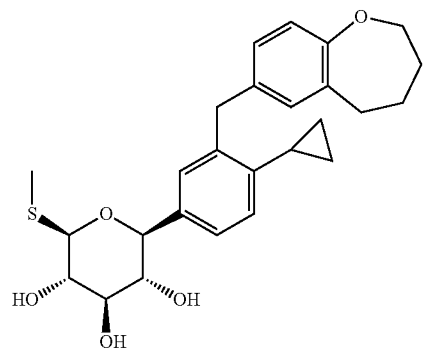 [SMILES: CS[C@H]1O[C@@H](c2ccc(C3CC3)c(Cc3ccc4c(c3)CCCCO4)c2)[C@H](O)[C@@H](O)[C@@H]1O] | 2S,3R,4R,5S,6R)-2-[4-Cyclopropyl-3-(2,3,4,5-tetrahydro-benzo[b]oxepin-7-ylmethyl)-phenyl]-6-methylsulfanyl-tetrahydro-pyran-3,4,5-triol |
| 5-2 | 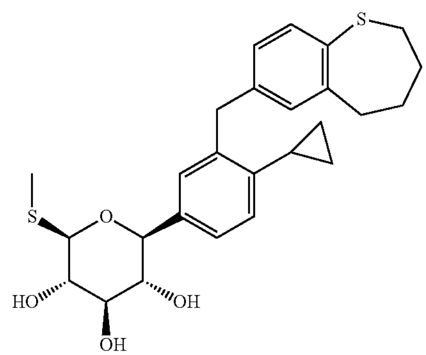 [SMILES: CS[C@H]1O[C@@H](c2ccc(C3CC3)c(Cc3ccc4c(c3)CCCCS4)c2)[C@H](O)[C@@H](O)[C@@H]1O] | (2S,3R,4R,5S,6R)-2-[4-Cyclopropyl-3-(2,3,4,5-tetrahydro-benzo[b]thiepin-7-ylmethyl)-phenyl]-6-methylsulfanyl-tetrahydro-pyran-3,4,5-triol |
| 5-3 | 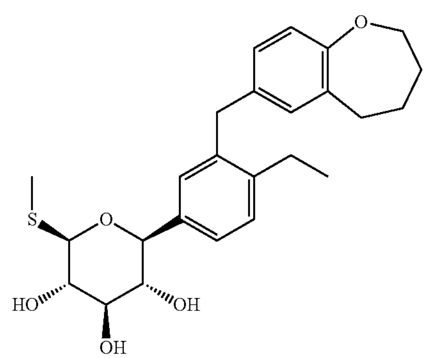 [SMILES: CCc1ccc([C@@H]2O[C@H](SC)[C@@H](O)[C@H](O)[C@H]2O)cc1Cc1ccc2c(c1)CCCCO2] | (2S,3R,4R,5S,6R)-2-[4-Ethyl-3-(2,3,4,5-tetrahydro-benzo[b]oxepin-7-ylmethyl)-phenyl]-6-methylsulfanyl-tetrahydro-pyran-3,4,5-triol |
| 5-4 | 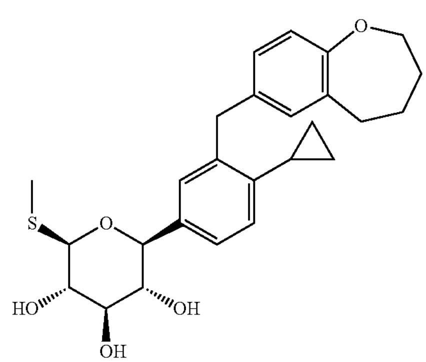 [SMILES: CS[C@H]1O[C@@H](c2ccc(C3CC3)c(Cc3ccc4c(c3)CCCCO4)c2)[C@H](O)[C@@H](O)[C@@H]1O] | (2S,3R,4R,5S,6R)-2-[4-Cyclopropyl-3-(2,3,4,5-tetrahydro-benzo[b]oxepin-7-ylmethyl)-phenyl]-6-Zethylsulfanyl-tetrahydro-pyran-3,4,5-triol |

-continued

| Ex. No. | Structure | Name |
|---|---|---|
| 5-5 | 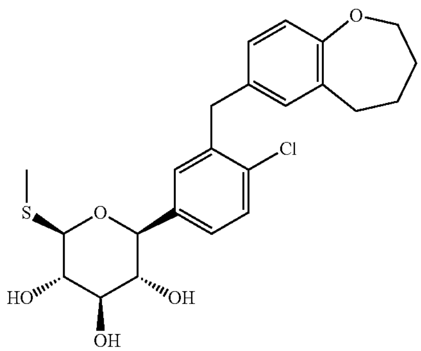 [SMILES: CS[C@H]1O[C@@H](c2ccc(Cl)c(Cc3ccc4c(c3)CCCCO4)c2)[C@H](O)[C@@H](O)[C@@H]1O] | (2S,3R,4R,5S,6R)-2-[4-Chloro-3-(2,3,4,5-tetrahydro-benzo[b]oxepin-7-ylmethyl)-phenyl]-6-methylsulfanyl-tetrahydro-pyran-3,4,5-triol |
| 5-6 | 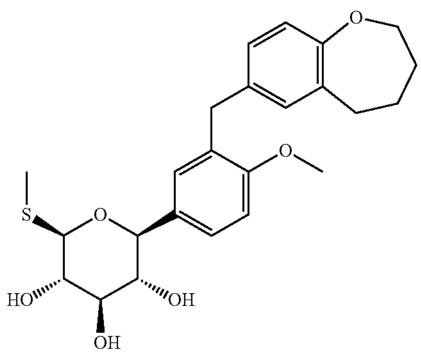 [SMILES: COc1ccc([C@@H]2O[C@H](SC)[C@@H](O)[C@H](O)[C@H]2O)cc1Cc1ccc2c(c1)CCCCO2] | (2S,3R,4R,5S,6R)-2-[4-Methoxy-3-(2,3,4,5-tetrahydro-benzo[b]oxepin-7-ylmethyl)-phenyl]-6-methylsulfanyl-tetrahydro-pyran-3,4,5-triol |
| 5-7 | 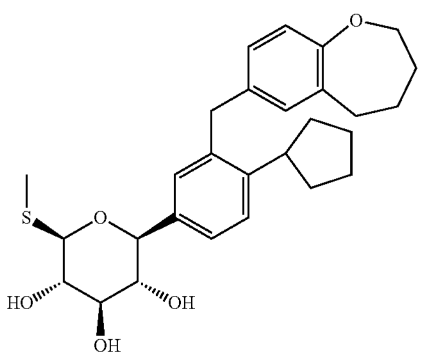 [SMILES: CS[C@H]1O[C@@H](c2ccc(C3CCCC3)c(Cc3ccc4c(c3)CCCCO4)c2)[C@H](O)[C@@H](O)[C@@H]1O] | (2S,3R,4R,5S,6R)-2-[4-Cyclopentyl-3-(2,3,4,5-tetrahydro-benzo[b]oxepin-7-ylmethyl)-phenyl]-6-methylsulfanyl-tetrahydro-pyran-3,4,5-triol |
| 5-8 | 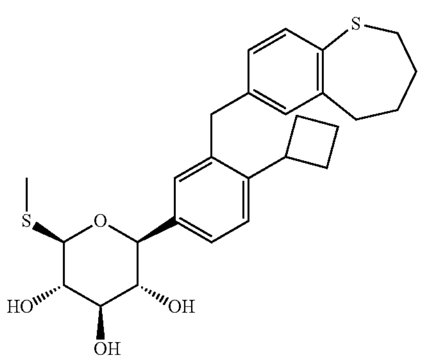 [SMILES: CS[C@H]1O[C@@H](c2ccc(C3CCC3)c(Cc3ccc4c(c3)CCCCS4)c2)[C@H](O)[C@@H](O)[C@@H]1O] | (2S,3R,4R,5S,6R)-2-[4-Cyclobutyl-3-(2,3,4,5-tetrahydro-benzo[b]thiepin-7-ylmethyl)-phenyl]-6-methylsulfanyl-tetrahydro-pyran-3,4,5-triol |

| Ex. No. | Structure | Name |
|---|---|---|
| 5-9 | 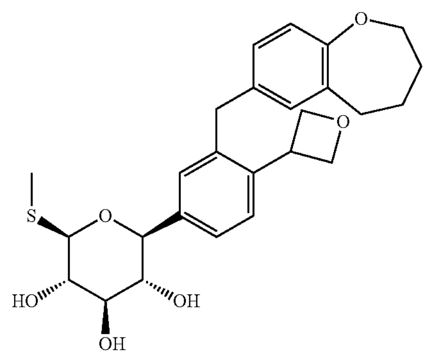 [SMILES: CS[C@H]1O[C@@H](c2ccc(C3COC3)c(Cc3ccc4c(c3)CCCCO4)c2)[C@H](O)[C@@H](O)[C@@H]1O] | (2R,3S,4R,5R,6S)-2-Methylsulfanyl-6-[4-oxetan-3-yl-3-(2,3,4,5-tetrahydro-benzo[b]oxepin-7-ylmethyl)-phenyl]-tetrahydro-pyran-3,4,5-triol |
| 5-10 | 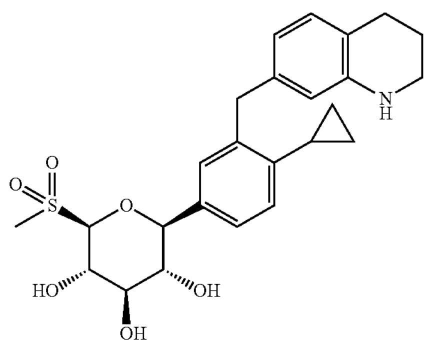 [SMILES: CS(=O)(=O)[C@H]1O[C@@H](c2ccc(C3CC3)c(Cc3ccc4c(c3)NCCC4)c2)[C@H](O)[C@@H](O)[C@@H]1O] | (2S,3R,4R,5S,6R)-2-[4-Cyclopropyl-3-(1,2,3,4-tetrahydro-quinolin-7-ylmethyl)-phenyl]-6-methanesulfonyl-tetrahydro-pyran-3,4,5-triol |
| 5-11 | 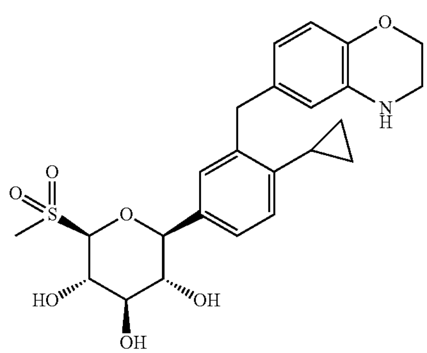 [SMILES: CS(=O)(=O)[C@H]1O[C@@H](c2ccc(C3CC3)c(Cc3ccc4c(c3)NCCO4)c2)[C@H](O)[C@@H](O)[C@@H]1O] | (2S,3R,4R,5S,6R)-2-[4-Cyclopropyl-3-(3,4-dihydro-2H-benzo[1,4]oxazin-6-ylmethyl)-phenyl]-6-methanesulfonyl-tetrahydro-pyran-3,4,5-triol |
| 5-12 | 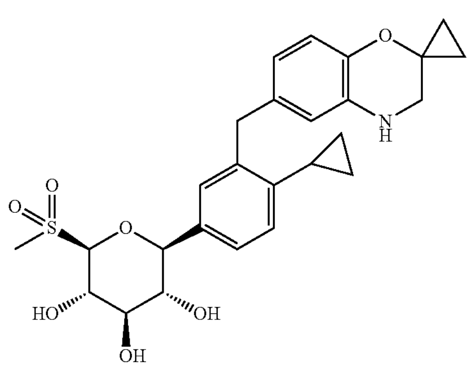 [SMILES: CS(=O)(=O)[C@H]1O[C@@H](c2ccc(C3CC3)c(Cc3ccc4c(c3)NCC3(CC3)O4)c2)[C@H](O)[C@@H](O)[C@@H]1O] | (2S,3R,4R,5S,6R)-2-(4-cyclopropyl-3-((3,4-dihydro-spiro[benzo[b][1,4]oxazine-2,1'-cyclopropane]-6-yl)methyl)phenyl)-6-(methylsulfonyl)tetrahydro-2H-pyran-3,4,5-triol |

| Ex. No. | Structure | Name |
|---|---|---|
| 5-13 | 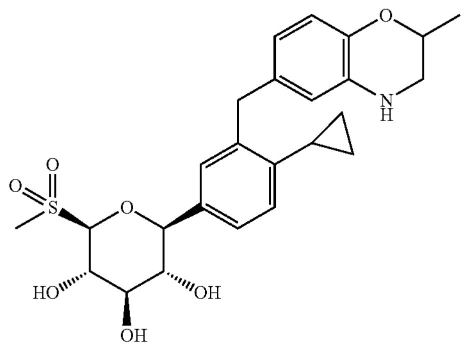 | (2S,3R,4R,5S,6R)-2-[4-Cyclopropyl-3-(2-methyl-3,4-dihydro-2H-benzo[1,4]oxazin-6-ylmethyl)-phenyl]-6-methanesulfonyl-tetrahydro-pyran-3,4,5-triol |
| 5-14 | 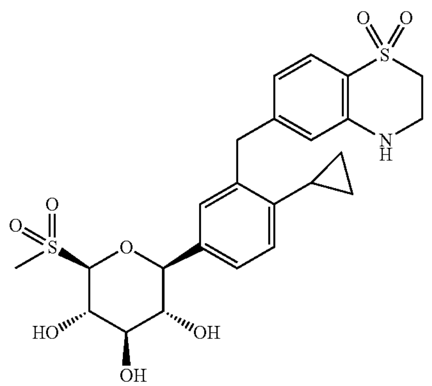 [SMILES: CS(=O)(=O)[C@H]1O[C@@H](c2ccc(C3CC3)c(Cc3ccc4c(c3)NCCS4(=O)=O)c2)[C@H](O)[C@@H](O)[C@@H]1O] | (2S,3R,4R,5S,6R)-2-[4-Cyclopropyl-3-(1,1-dioxo-1,2,3,4-tetrahydro-1lambda*6*-benzo[1,4]thiazin-6-ylmethyl)-phenyl]-6-methanesulfonyl-tetrahydro-pyran-3,4,5-triol |
| 5-15 | 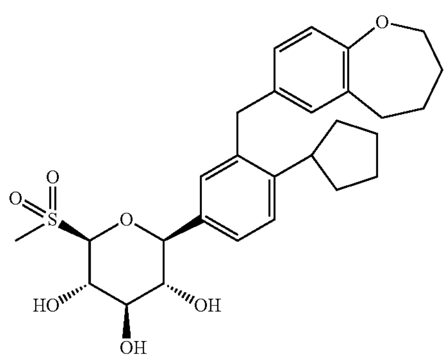 [SMILES: CS(=O)(=O)[C@H]1O[C@@H](c2ccc(C3CCCC3)c(Cc3ccc4c(c3)CCCCO4)c2)[C@H](O)[C@@H](O)[C@@H]1O] | (2S,3R,4R,5S,6R)-2-[4-Cyclopentyl-3-(2,3,4,5-tetrahydro-benzo[b]oxepin-7-ylmethyl)-phenyl]-6-methanesulfonyl-tetrahydro-pyran-3,4,5-triol |
| 5-16 | 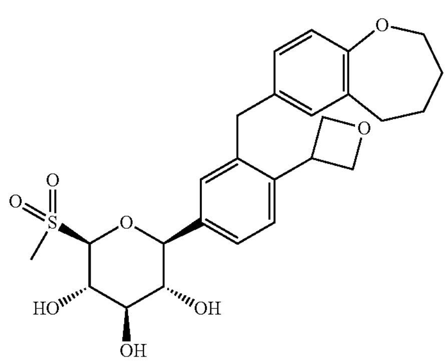 [SMILES: CS(=O)(=O)[C@H]1O[C@@H](c2ccc(C3COC3)c(Cc3ccc4c(c3)CCCCO4)c2)[C@H](O)[C@@H](O)[C@@H]1O] | (2R,3S,4R,5R,6S)-2-Methanesulfonyl-6-[4-oxetan-3-yl-3-(2,3,4,5-tetrahydro-benzo[b]oxepin-7-ylmethyl)-phenyl]-tetrahydro-pyran-3,4,5-triol |

| Ex. No. | Structure | Name |
|---|---|---|
| 5-17 | 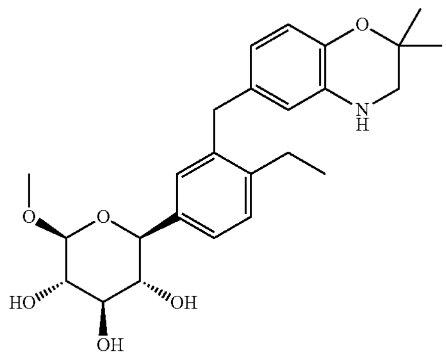 [SMILES: CCc1ccc([C@@H]2O[C@H](OC)[C@@H](O)[C@H](O)[C@H]2O)cc1Cc1ccc2c(c1)NCC(C)(C)O2] | (2S,3R,4R,5S,6S)-2-[3-(2,2-Dimethyl-3,4-dihydro-2H-benzo[1,4]oxazin-6-ylmethyl)-4-ethyl-phenyl]-6-methoxy-tetrahydro-pyran-3,4,5-triol |
| 5-18 | 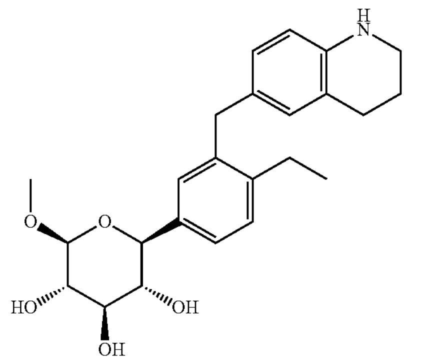 [SMILES: CCc1ccc([C@@H]2O[C@H](OC)[C@@H](O)[C@H](O)[C@H]2O)cc1Cc1ccc2c(c1)CCCN2] | (2S,3R,4R,5S,6S)-2-[4-Ethyl-3-(1,2,3,4-tetrahydro-quinolin-6-ylmethyl)-phenyl]-6-methoxy-tetrahydro-pyran-3,4,5-triol |
| 5-19 | 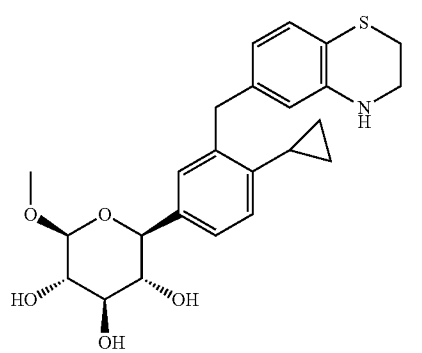 [SMILES: CO[C@H]1O[C@@H](c2ccc(C3CC3)c(Cc3ccc4c(c3)NCCS4)c2)[C@H](O)[C@@H](O)[C@@H]1O] | (2S,3R,4R,5S,6S))-2-[4-Cyclopropyl-3-(3,4-dihydro-2H-benzo[1,4]thiazin-6-ylmethyl)-phenyl]-6-methoxy-tetrahydro-pyran-3,4,5-triol |
| 5-20 | 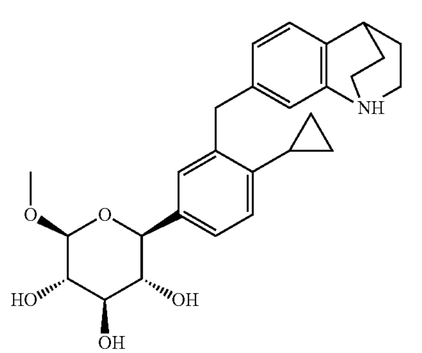 [SMILES: CO[C@H]1O[C@@H](c2ccc(C3CC3)c(Cc3ccc4c(c3)N3CCC4CC3)c2)[C@H](O)[C@@H](O)[C@@H]1O] | (2S,3R,4R,5S,6S)-2-[4-Cyclopropyl-3-(3,4-dihydro-2H-1,4-ethano-quinolin-7-ylmethyl)-phenyl]-6-methoxy-tetrahydro-pyran-3,4,5-triol |

| Ex. No. | Structure | Name |
|---------|-----------|------|
| 5-21 | 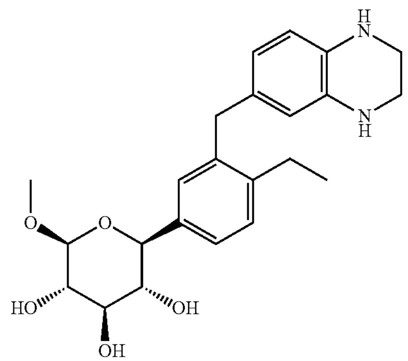 [SMILES: CCc1ccc([C@@H]2O[C@H](OC)[C@@H](O)[C@H](O)[C@H]2O)cc1Cc1ccc2c(c1)NCCN2] | (2S,3R,4R,5S,6S)-2-[4-Ethyl-3-(1,2,3,4-tetrahydro-quinoxalin-6-ylmethyl)-phenyl]-6-methoxy-tetrahydro-pyran-3,4,5-triol |
| 5-22 | 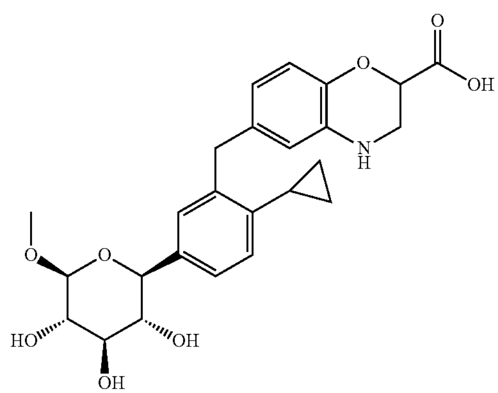 [SMILES: CO[C@H]1O[C@@H](c2ccc(C3CC3)c(Cc3ccc4c(c3)NCC(C(=O)O)O4)c2)[C@H](O)[C@@H](O)[C@@H]1O] | 6-[2-Cyclopropyl-5-((2S,3R,4R,5S,6S)-3,4,5-trihydroxy-6-methoxy-tetrahydro-pyran-2-yl)-benzyl]-3,4-dihydro-2H-benzo[1,4]oxazine-2-carboxylic acid |
| 5-23 | 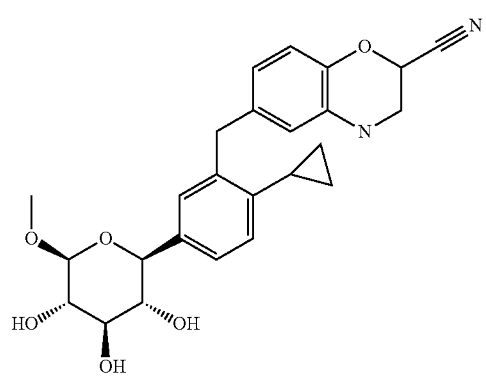 [SMILES: CO[C@H]1O[C@@H](c2ccc(C3CC3)c(Cc3ccc4c(c3)NCC(C#N)O4)c2)[C@H](O)[C@@H](O)[C@@H]1O] | 6-[2-Cyclopropyl-5-((2S,3R,4R,5S,6S)-3,4,5-trihydroxy-6-methoxy-tetrahydro-pyran-2-yl)-benzyl]-3,4-dihydro-2H-benzo[1,4]oxazine-2-carbonitrile |
| 5-24 | 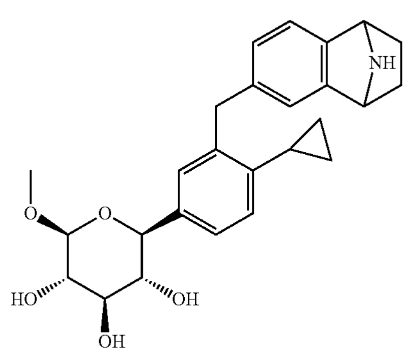 [SMILES: CO[C@H]1O[C@@H](c2ccc(C3CC3)c(Cc3ccc4c(c3)C3CCC4N3)c2)[C@H](O)[C@@H](O)[C@@H]1O] | (2S,3R,4R,5S,6S)-2-[4-Cyclopropyl-3-(5-methylamino-5,6,7,8-tetrahydro-naphthalen-2-ylmethyl)-phenyl]-6-methoxy-tetrahydro-pyran-3,4,5-triol |

| Ex. No. | Structure | Name |
|---|---|---|
| 5-25 | 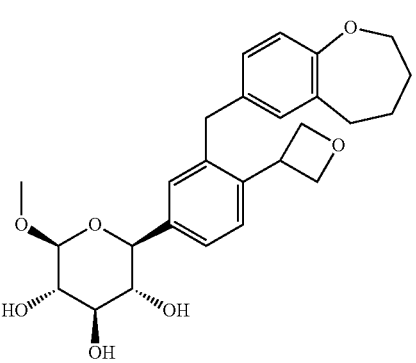 [SMILES: CO[C@H]1O[C@@H](c2ccc(C3COC3)c(Cc3ccc4c(c3)CCCCO4)c2)[C@H](O)[C@@H](O)[C@@H]1O] | (2S,3S,4R,5R,6S)-2-Methoxy-6-[4-oxetan-3-yl-3-(2,3,4,5-tetrahydro-benzo[b]oxepin-7-ylmethyl)-phenyl]-tetrahydro-pyran-3,4,5-triol |
| 5-26 | 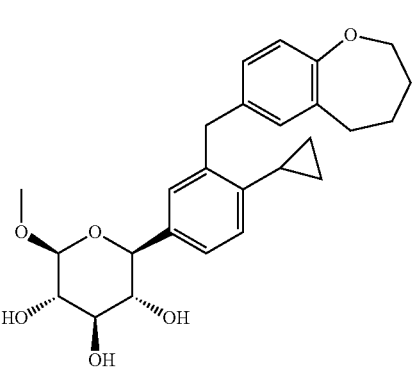 [SMILES: CO[C@H]1O[C@@H](c2ccc(C3CC3)c(Cc3ccc4c(c3)CCCCO4)c2)[C@H](O)[C@@H](O)[C@@H]1O] | (2S,3R,4R,5S,6S)-2-[4-Cyclopropyl-3-(2,3,4,5-tetrahydro-benzo[b]oxepin-7-ylmethyl)-phenyl]-6-methoxy-tetrahydro-pyran-3,4,5-triol |
| 5-27 | 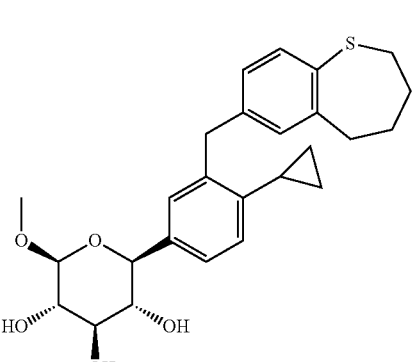 | (2S,3R,4R,5S,6S)-2-[4-Cyclopropyl-3-(2,3,4,5-tetrahydro-benzo[b]thiepin-7-ylmethyl)-phenyl]-6-methoxy-tetrahydro-pyran-3,4,5-triol |
| 5-28 | 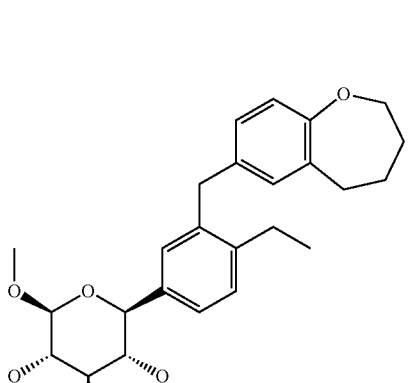 | (2S,3R,4R,5S,6S)-2-[4-Ethyl-3-(2,3,4,5-tetrahydro-benzo[b]oxepin-7-ylmethyl)-phenyl]-6-methoxy-tetrahydro-pyran-3,4,5-triol |

| Ex. No. | Structure | Name |
|---|---|---|
| 5-29 | 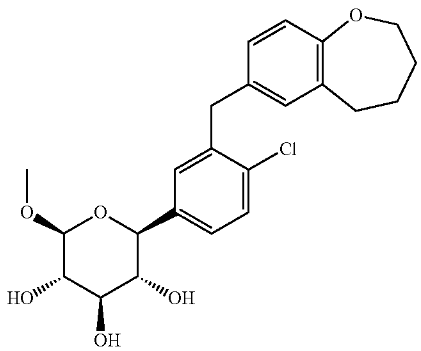 [SMILES: CO[C@H]1O[C@@H](c2ccc(Cl)c(Cc3ccc4c(c3)CCCCO4)c2)[C@H](O)[C@@H](O)[C@@H]1O] | (2S,3R,4R,5S,6S)-2-[4-Chloro-3-(2,3,4,5-tetrahydro-benzo[b]oxepin-7-ylmethyl)-phenyl]-6-methoxy-tetrahydro-pyran-3,4,5-triol |
| 5-30 | 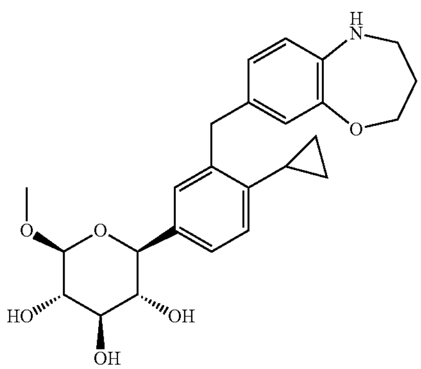 [SMILES: CO[C@H]1O[C@@H](c2ccc(C3CC3)c(Cc3ccc4c(c3)OCCCN4)c2)[C@H](O)[C@@H](O)[C@@H]1O] | (2S,3R,4R,5S,6S)-2-[4-Cyclopropyl-3-(6,7,8,9-tetrahydro-5-oxa-9-aza-benzocyclohepten-3-ylmethyl)-phenyl]-6-methoxy-tetrahydro-pyran-3,4,5-triol |
| 5-31 | 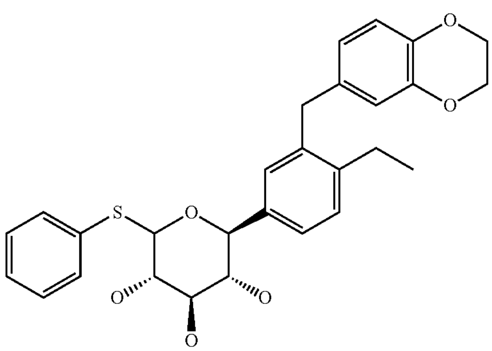 [SMILES: CCc1ccc([C@@H]2OC(Sc3ccccc3)[C@@H](O)[C@H](O)[C@H]2O)cc1Cc1ccc2c(c1)OCCO2] | (2S,3R,4R,5S)-2-[3-(2,3-Dihydro-benzo[1,4]dioxin-6-ylmethyl)-4-ethyl-phenyl]-6-phenylsulfanyl-tetrahydro-pyran-3,4,5-triol |
| 5-32 | 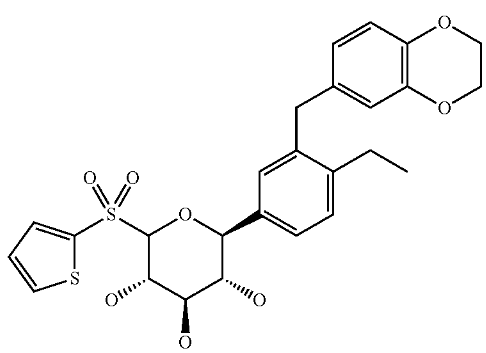 [SMILES: CCc1ccc([C@@H]2OC(S(=O)(=O)c3cccs3)[C@@H](O)[C@H](O)[C@H]2O)cc1Cc1ccc2c(c1)OCCO2] | (2S,3R,4R,5S)-2-[3-(2,3-Dihydro-benzo[1,4]dioxin-6-ylmethyl)-4-ethyl-phenyl]-6-(thiophene-2-sulfonyl)-tetrahydro-pyran-3,4,5-triol |

| Ex. No. | Structure | Name |
|---|---|---|
| 5-33 | 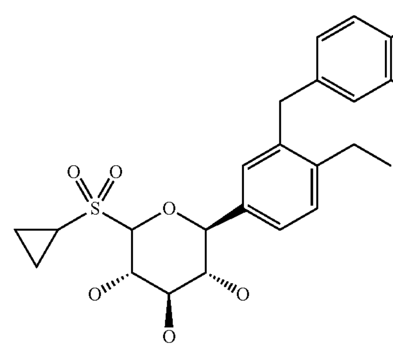 | (3S,4R,5R,6S)-2-Cyclopropanesulfonyl-6-[3-(2,3-dihydro-benzo[1,4]dioxin-6-ylmethyl)-4-ethyl-phenyl]-tetrahydro-pyran-3,4,5-triol |
| 5-34 | 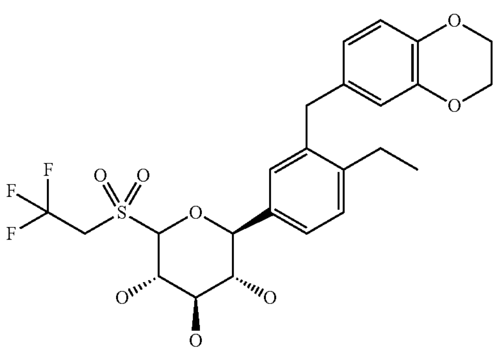 [SMILES: CCc1ccc([C@@H]2OC(S(=O)(=O)CC(F)(F)F)[C@@H](O)[C@H](O)[C@H]2O)cc1Cc1ccc2c(c1)OCCO2] | (2S,3R,4R,5S)-2-[3-(2,3-Dihydro-benzo[1,4]dioxin-6-ylmethyl)-4-ethyl-phenyl]-6-(2,2,2-trifluoro-ethanesulfonyl)-tetrahydro-pyran-3,4,5-triol |
| 5-35 | 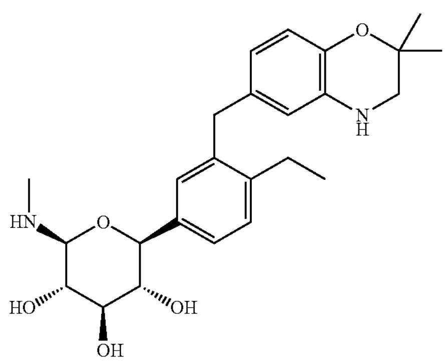 [SMILES: CCc1ccc([C@@H]2O[C@H](NC)[C@@H](O)[C@H](O)[C@H]2O)cc1Cc1ccc2c(c1)NCC(C)(C)O2] | (2S,3R,4R,5S,6S)-2-[3-(2,2-Dimethyl-3,4-dihydro-2H-benzo[1,4]oxazin-6-ylmethyl)-4-ethyl-phenyl]-6-methylamino-tetrahydro-pyran-3,4,5-triol |
| 5-36 | 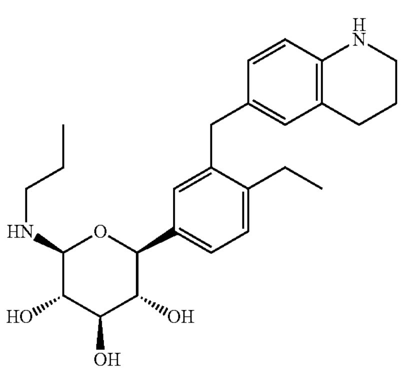 [SMILES: CCCN[C@H]1O[C@@H](c2ccc(CC)c(Cc3ccc4c(c3)CCCN4)c2)[C@H](O)[C@@H](O)[C@@H]1O] | (2S,3R,4R,5S,6S)-2-[4-Ethyl-3-(1,2,3,4-tetrahydro-quinolin-6-ylmethyl)-phenyl]-6-propylamino-tetrahydro-pyran-3,4,5-triol |

-continued

| Ex. No. | Structure | Name |
|---|---|---|
| 5-37 | 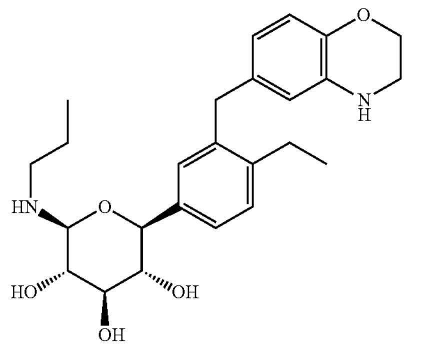 [SMILES: CCCN[C@H]1O[C@@H](c2ccc(CC)c(Cc3ccc4c(c3)NCCO4)c2)[C@H](O)[C@@H](O)[C@@H]1O] | (2S,3R,4R,5S,6S)-2-[3-(3,4-Dihydro-2H-benzo[1,4]oxazin-6-ylmethyl)-4-ethyl-phenyl]-6-propylamino-tetrahydro-pyran-3,4,5-triol |
| 5-38 | 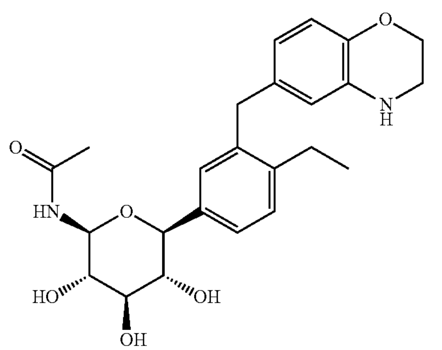 [SMILES: CCc1ccc([C@@H]2O[C@H](NC(C)=O)[C@@H](O)[C@H](O)[C@H]2O)cc1Cc1ccc2c(c1)NCCO2] | N-{(2S,3S,4R,5R,6S)-6-[3-(3,4-Dihydro-2H-benzo[1,4]oxazin-6-ylmethyl)-4-ethyl-phenyl]-3,4,5-trihydroxy-tetrahydro-pyran-2-yl}-acetamide |
| 5-39 | 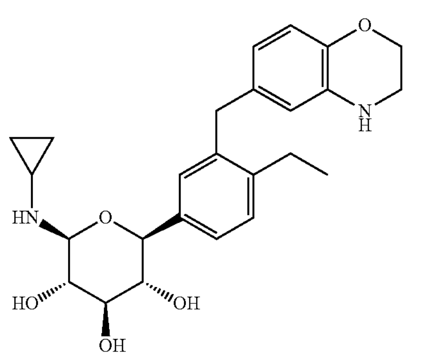 [SMILES: CCc1ccc([C@@H]2O[C@H](NC3CC3)[C@@H](O)[C@H](O)[C@H]2O)cc1Cc1ccc2c(c1)NCCO2] | (2S,3S,4R,5R,6S)-2-Cyclopropylamino-6-[3-(3,4-dihydro-2H-benzo[1,4]oxazin-6-ylmethyl)-4-ethyl-phenyl]-tetrahydro-pyran-3,4,5-triol |
| 5-40 | 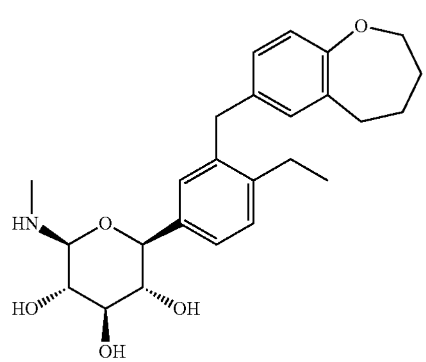 [SMILES: CCc1ccc([C@@H]2O[C@H](NC)[C@@H](O)[C@H](O)[C@H]2O)cc1Cc1ccc2c(c1)CCCCO2] | (2S,3R,4R,5S,6S)-2-[4-Ethyl-3-(2,3,4,5-tetrahydro-benzo[b]oxepin-7-ylmethyl)-phenyl]-6-methylamino-tetrahydro-pyran-3,4,5-triol |

| Ex. No. | Structure | Name |
|---|---|---|
| 5-41 | 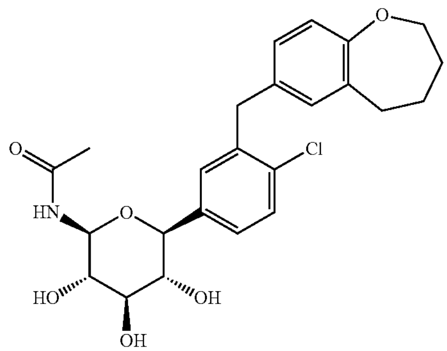 [SMILES: CC(=O)N[C@H]1O[C@@H](c2ccc(Cl)c(Cc3ccc4c(c3)CCCCO4)c2)[C@H](O)[C@@H](O)[C@@H]1O] | N-{(2S,3S,4R,5R,6S)-6-[4-Chloro-3-(2,3,4,5-tetrahydro-benzo[b]oxepin-7-ylmethyl)-phenyl]-3,4,5-trihydroxy-tetrahydro-pyran-2-yl}-acetamide |
| 5-42 | 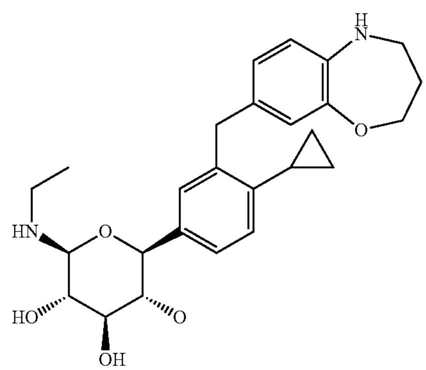 [SMILES: CCN[C@H]1O[C@@H](c2ccc(C3CC3)c(Cc3ccc4c(c3)OCCCN4)c2)[C@H](O)[C@@H](O)[C@@H]1O] | (2S,3R,4R,5S,6S)-2-[4-Cyclopropyl-3-(6,7,8,9-tetrahydro-5-oxa-9-aza-benzocyclohepten-3-ylmethyl)-phenyl]-6-ethylamino-tetrahydro-pyran-3,4,5-triol |
| 5-43 | 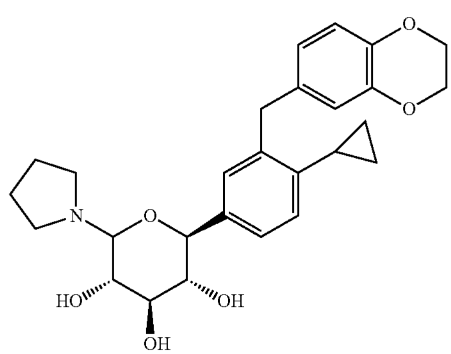 [SMILES: O[C@@H]1[C@@H](O)[C@H](c2ccc(C3CC3)c(Cc3ccc4c(c3)OCCO4)c2)OC(N2CCCC2)[C@H]1O] | (2S,3R,4R,5S)-2-[4-Cyclopropyl-3-(2,3-dihydro-benzo[1,4]dioxin-6-ylmethyl)-phenyl]-6-pyrrolidin-1-yl-tetrahydro-pyran-3,4,5-triol |
| 5-44 | 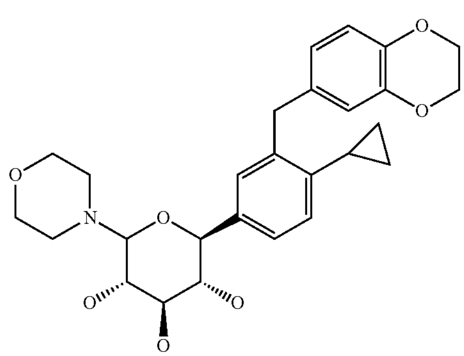 [SMILES: O[C@@H]1[C@@H](O)[C@H](c2ccc(C3CC3)c(Cc3ccc4c(c3)OCCO4)c2)OC(N2CCOCC2)[C@H]1O] | (2S,3R,4R,5S)-2-[4-Cyclopropyl-3-(2,3-dihydro-benzo[1,4]dioxin-6-ylmethyl)-phenyl]-6-morpholin-4-yl-tetrahydro-pyran-3,4,5-triol |

The following are further embodiments of the invention:

Embodiment 1: A compound represented by structural formula (I)

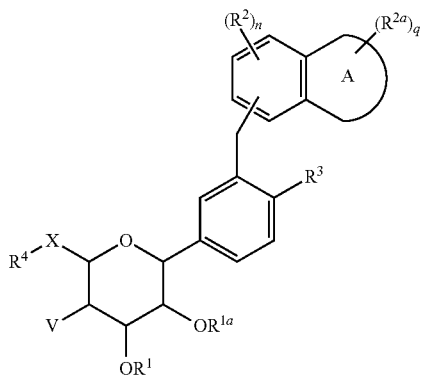
(I)

or a pharmaceutically acceptable salt thereof, wherein:
  ring A is a 5-, 6- or 7-membered heterocyclyl;
  X is O, $NR^5$, S, S(O) or $S(O)_2$;
  V is hydrogen, halo or $-OR^{1b}$;
  $R^1$, $R^{1a}$ and $R^{1b}$ are independently selected from the group consisting of hydrogen, $C_{1-6}$ alkyl, $C_{6-10}$aryl-$C_{1-4}$alkyl, $C(O)C_{6-10}$aryl and $-C(O)C_{1-6}$alkyl;
  $R^2$ and $R^{2a}$, for each occurrence, are independently selected from the group consisting of halo, hydroxy, cyano, carboxy, $C_{1-6}$alkyl, $C_{1-6}$alkoxy and $C_{3-10}$cycloalkyl;
  $R^3$ is halo, hydroxy, $C_{1-6}$alkyl, halo$C_{1-6}$alkyl, $C_{3-10}$cycloalkyl, $C_{1-6}$alkoxy, halo$C_{1-3}$alkoxy or a 3- to 7-membered heterocyclyl;
  $R^4$ is a $C_{1-6}$alkyl, halo$C_{1-6}$alkyl, $C_{3-10}$cycloalkyl, $C_{6-10}$aryl, or a 5- to 10-membered heteroaryl;
  $R^5$ is hydrogen, $C_{1-6}$alkyl, $C_{3-10}$cycloalkyl, or $C_{1-6}$alkanoyl; or
  $R^4$ and $R^5$ together with the nitrogen to which they are attached form a 3- to 7-membered heterocyclyl;
  n is 0, 1, 2, or 3; and
  q is 0, 1, or 2.

Embodiment 2: The compound of Embodiment 1, or a pharmaceutically acceptable salt thereof, wherein the group represented by the following formula:

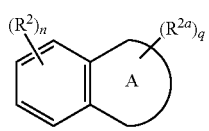

is selected from the group consisting of:

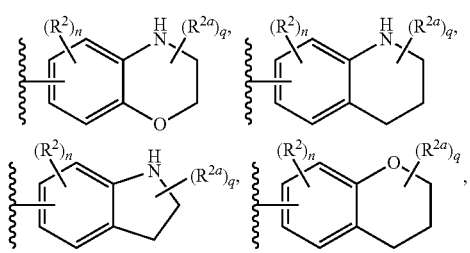

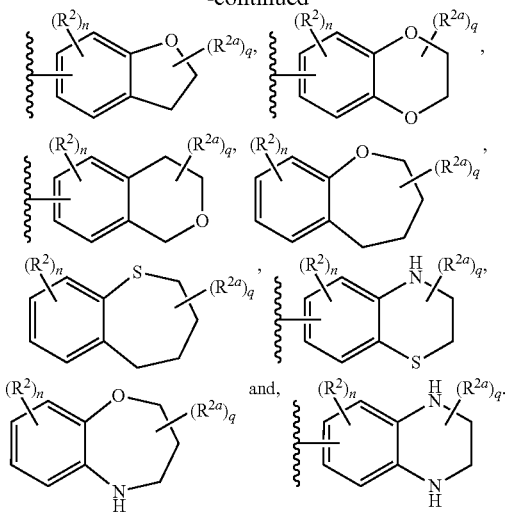

Embodiment 3: The compound of Embodiment 1 or 2, or a pharmaceutically acceptable salt thereof, wherein the group represented by the following formula:

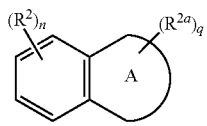

is selected from the group consisting of:

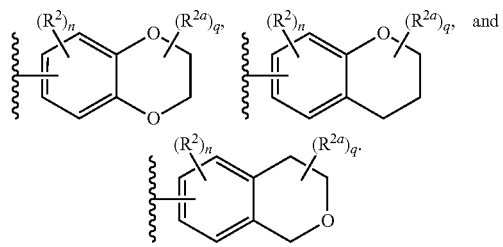

Embodiment 4: The compound of anyone of the preceding embodiments, or a pharmaceutically acceptable salt thereof, wherein the group represented by the following formula:

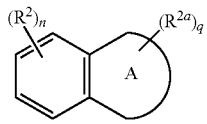

is selected from the group consisting of:

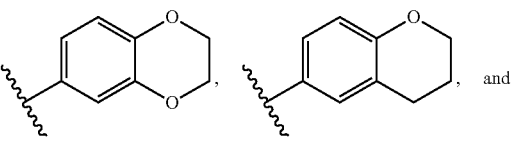

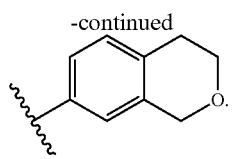

Embodiment 5: The compound of anyone of the preceding embodiments, or a pharmaceutically acceptable salt thereof, wherein the group represented by the following formula:

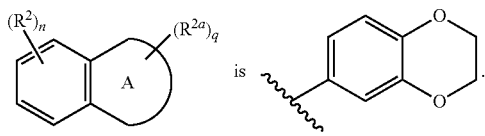

Embodiment 6: The compound of anyone of Embodiments 1-3, or a pharmaceutically acceptable salt thereof, wherein n is 0.

Embodiment 7: The compound of anyone of Embodiments 1-3 and 6, or a pharmaceutically acceptable salt thereof, wherein q is 0.

Embodiment 8: The compound of anyone of the preceeding embodiments, or a pharmaceutically acceptable salt thereof, wherein V is —$OR^{1b}$.

Embodiment 9: The compound of anyone of the preceeding embodiments, or a pharmaceutically acceptable salt thereof, wherein $R^1$, $R^{1a}$, and $R^{1b}$ are hydrogen.

Embodiment 10: The compound of anyone of the preceeding embodiments, or a pharmaceutically acceptable salt thereof, wherein $R^3$ is halo, $C_{1-6}$alkyl, or $C_{3-10}$cycloalkyl.

Embodiment 11: The compound of anyone of the preceeding embodiments, or a pharmaceutically acceptable salt thereof, wherein $R^3$ is bromo, ethyl or cyclopropyl.

Embodiment 12: The compound of anyone of the preceeding embodiments, or a pharmaceutically acceptable salt thereof, wherein $R^3$ is ethyl.

Embodiment 13: The compound of anyone of the proceeding embodiments, or a pharmaceutically acceptable salt thereof, wherein X is O.

Embodiment 14: The compound of anyone of Embodiments 1-12, or a pharmaceutically acceptable salt thereof, wherein X is S.

Embodiment 15: The compound of anyone of Embodiments 1-12, or a pharmaceutically acceptable salt thereof, wherein X is $S(O)_2$.

Embodiment 16: The compound of anyone of Embodiments 1-12, or a pharmaceutically acceptable salt thereof, wherein X is $NR^5$.

Embodiment 17: The compound of anyone of the proceeding embodiments, or a pharmaceutically acceptable salt thereof, wherein $R^4$ is $C_{1-4}$alkyl, halo$C_{1-4}$alkyl, $C_{3-6}$cycloalkyl, phenyl, or a 5- to 6-membered heteroaryl.

Embodiment 18: The compound of anyone of the proceeding embodiments, or a pharmaceutically acceptable salt thereof, wherein $R^4$ is methyl.

Embodiment 19: The compound of Embodiment 16, or a pharmaceutically acceptable salt thereof, wherein $R^4$ is a $C_{1-6}$alkyl and $R^5$ is a $C_{1-6}$alkanoyl.

Embodiment 20: The compound of Embodiment 19, or a pharmaceutically acceptable salt thereof, wherein $R^4$ is n-propyl and $R^5$ is acetyl.

Embodiment 21: The compound of Embodiment 16, or a pharmaceutically acceptable salt thereof, wherein $R^4$ and $R^5$ together with the nitrogen to which they are attached form a 5- to 6-membered heterocyclyl.

Embodiment 22: The compound of Embodiment 21, or a pharmaceutically acceptable salt thereof, wherein $R^4$ and $R^5$ together with the nitrogen to which they are attached form a pyrrolidino or a morpholino.

Embodiment 23: The compound of Embodiment 1, or a pharmaceutically acceptable salt thereof, wherein the compound is selected from the group consisting of:
(2S,3R,4R,5S)-2-[4-cyclopropyl-3-(2,3-dihydro-benzo[1,4]dioxin-6-ylmethyl)-phenyl]-6-methylsulfanyl-tetrahydro-pyran-3,4,5-triol;
(2S,3R,4R,5S,6R)-2-[3-(2,3-Dihydro-benzo[1,4]dioxin-6-ylmethyl)-4-ethyl-phenyl]-6-methylsulfanyl-tetrahydro-pyran-3,4,5-triol;
(2S,3R,4R,5S,6R)-2-(3-Chroman-6-ylmethyl-4-ethyl-phenyl)-6-methylsulfanyl-tetrahydropyran-3,4,5-triol;
(2S,3R,4R,5S,6R)-2-[4-Bromo-3-(2,3-dihydro-benzo[1,4]dioxin-6-ylmethyl)-phenyl]-6-methylsulfanyl-tetrahydro-pyran-3,4,5-triol;
(2S,3R,4R,5S,6R)-2-(3-Chroman-6-ylmethyl-4-cyclopropyl-phenyl)-6-methylsulfanyl-tetrahydropyran-3,4,5-triol;
(2S,3R,4R,5S,6R)-2-(4-Bromo-3-chroman-6-ylmethyl-phenyl)-6-methylsulfanyl-tetrahydro-pyran-3,4,5-triol;
(2S,3R,4R,5S,6R)-2-(4-Bromo-3-isochroman-7-ylmethyl-phenyl)-6-methylsulfanyl-tetrahydropyran-3,4,5-triol;
(2S,3R,4R,5S,6R)-2-(4-Ethyl-3-isochroman-7-ylmethyl-phenyl)-6-methylsulfanyl-tetrahydropyran-3,4,5-triol;
(2S,3R,4R,5S)-2-[4-Cyclopropyl-3-(2,3-dihydro-benzo[1,4]dioxin-6-ylmethyl)-phenyl]-6-methanesulfonyl-tetrahydro-pyran-3,4,5-triol;
(2S,3R,4R,5S,6R)-2-[3-(2,3-Dihydro-benzo[1,4]dioxin-6-ylmethyl)-4-ethyl-phenyl]-6-methanesulfonyl-tetrahydro-pyran-3,4,5-triol;
(2S,3R,4R,5S,6R)-2-(3-Chroman-6-ylmethyl-4-ethyl-phenyl)-6-methanesulfonyl-tetrahydropyran-3,4,5-triol;
(2S,3R,4R,5S,6R)-2-[4-Bromo-3-(2,3-dihydro-benzo[1,4]dioxin-6-ylmethyl)-phenyl]-6-methanesulfonyl-tetrahydro-pyran-3,4,5-triol;
(2S,3R,4R,5S,6R)-2-(3-Chroman-6-ylmethyl-4-cyclopropyl-phenyl)-6-methanesulfonyl-tetrahydro-pyran-3,4,5-triol;
(2S,3R,4R,5S,6R)-2-(4-Bromo-3-chroman-6-ylmethyl-phenyl)-6-methanesulfonyl-tetrahydro-pyran-3,4,5-triol;
(2S,3R,4R,5S,6S)-2-[4-Cyclopropyl-3-(2,3-dihydro-benzo[1,4]dioxin-6-ylmethyl)-phenyl]-6-methoxy-tetrahydro-pyran-3,4,5-triol;
(2S,3R,4R,5S,6S)-2-(4-Bromo-3-chroman-6-ylmethyl-phenyl)-6-methoxy-tetrahydro-pyran-3,4,5-triol;
(2S,3R,4R,5S,6S)-2-(3-Chroman-6-ylmethyl-4-ethyl-phenyl)-6-methoxy-tetrahydro-pyran-3,4,5-triol;
(2S,3R,4R,5S,6S)-2-(3-Chroman-6-ylmethyl-4-cyclopropyl-phenyl)-6-methoxy-tetrahydro-pyran-3,4,5-triol;
(2S,3R,4R,5S,6S)-2-[3-(2,3-Dihydro-benzo[1,4]dioxin-6-ylmethyl)-4-ethyl-phenyl]-6-methoxy-tetrahydro-pyran-3,4,5-triol;
N-[(3S,4R,5R,6S)-6-(3-chroman-6-ylmethyl-4-ethyl-phenyl)-3,4,5-trihydroxy-tetrahydro-pyran-2-yl]-N-propyl-acetamide;
2S,3R,4R,5S,6R)-2-[4-Cyclopropyl-3-(2,3,4,5-tetrahydro-benzo[b]oxepin-7-ylmethyl)-phenyl]-6-methylsulfanyl-tetrahydro-pyran-3,4,5-triol;
(2S,3R,4R,5S,6R)-2-[4-Cyclopropyl-3-(2,3,4,5-tetrahydro-benzo[b]thiepin-7-ylmethyl)-phenyl]-6-methylsulfanyl-tetrahydro-pyran-3,4,5-triol
(2S,3R,4R,5S,6R)-2-[4-Ethyl-3-(2,3,4,5-tetrahydro-benzo[b]oxepin-7-ylmethyl)-phenyl]-6-methylsulfanyl-tetrahydro-pyran-3,4,5-triol;
(2S,3R,4R,5S,6R)-2-[4-Cyclopropyl-3-(2,3,4,5-tetrahydro-benzo[b]oxepin-7-ylmethyl)-phenyl]-6-Zethylsulfanyl-tetrahydro-pyran-3,4,5-triol;

(2S,3R,4R,5S,6R)-2-[4-Chloro-3-(2,3,4,5-tetrahydro-benzo[b]oxepin-7-ylmethyl)-phenyl]-6-methylsulfanyl-tetrahydro-pyran-3,4,5-triol;

(2S,3R,4R,5S,6R)-2-[4-Methoxy-3-(2,3,4,5-tetrahydro-benzo[b]oxepin-7-ylmethyl)-phenyl]-6-methylsulfanyl-tetrahydro-pyran-3,4,5-triol;

(2S,3R,4R,5S,6R)-2-[4-Cyclopentyl-3-(2,3,4,5-tetrahydro-benzo[b]oxepin-7-ylmethyl)-phenyl]-6-methylsulfanyl-tetrahydro-pyran-3,4,5-triol;

(2S,3R,4R,5S,6R)-2-[4-Cyclobutyl-3-(2,3,4,5-tetrahydro-benzo[b]thiepin-7-ylmethyl)-phenyl]-6-methylsulfanyl-tetrahydro-pyran-3,4,5-triol;

(2R,3S,4R,5R,6S)-2-Methylsulfanyl-6-[4-oxetan-3-yl-3-(2,3,4,5-tetrahydro-benzo[b]oxepin-7-ylmethyl)-phenyl]-tetrahydro-pyran-3,4,5-triol;

(2S,3R,4R,5S,6R)-2-[4-Cyclopropyl-3-(1,2,3,4-tetrahydro-quinolin-7-ylmethyl)-phenyl]-6-methanesulfonyl-tetrahydro-pyran-3,4,5-triol;

(2S,3R,4R,5S,6R)-2-[4-Cyclopropyl-3-(3,4-dihydro-2H-benzo[1,4]oxazin-6-ylmethyl)-phenyl]-6-methanesulfonyl-tetrahydro-pyran-3,4,5-triol;

(2S,3R,4R,5S,6R)-2-(4-cyclopropyl-3-((3,4-dihydro-spiro[benzo[b][1,4]oxazine-2,1'-cyclopropane]-6-yl)methyl)phenyl)-6-(methylsulfonyl)tetrahydro-2H-pyran-3,4,5-triol;

(2S,3R,4R,5S,6R)-2-[4-Cyclopropyl-3-(2-methyl-3,4-dihydro-2H-benzo[1,4]oxazin-6-ylmethyl)-phenyl]-6-methanesulfonyl-tetrahydro-pyran-3,4,5-triol;

(2S,3R,4R,5S,6R)-2-[4-Cyclopropyl-3-(1,1-dioxo-1,2,3,4-tetrahydro-1lambda*6*-benzo[1,4]thiazin-6-ylmethyl)-phenyl]-6-methanesulfonyl-tetrahydro-pyran-3,4,5-triol;

(2S,3R,4R,5S,6R)-2-[4-Cyclopentyl-3-(2,3,4,5-tetrahydro-benzo[b]oxepin-7-ylmethyl)-phenyl]-6-methanesulfonyl-tetrahydro-pyran-3,4,5-triol;

(2R,3S,4R,5R,6S)-2-Methanesulfonyl-6-[4-oxetan-3-yl-3-(2,3,4,5-tetrahydro-benzo[b]oxepin-7-ylmethyl)-phenyl]-tetrahydro-pyran-3,4,5-triol;

(2S,3R,4R,5S,6S)-2-[3-(2,2-Dimethyl-3,4-dihydro-2H-benzo[1,4]oxazin-6-ylmethyl)-4-ethyl-phenyl]-6-methoxy-tetra hydro-pyran-3,4,5-triol;

(2S,3R,4R,5S,6S)-2-[4-Ethyl-3-(1,2,3,4-tetrahydro-quinolin-6-ylmethyl)-phenyl]-6-methoxy-tetrahydro-pyran-3,4,5-triol;

(2S,3R,4R,5S,6S)-2-[4-Cyclopropyl-3-(3,4-dihydro-2H-benzo[1,4]thiazin-6-ylmethyl)-phenyl]-6-methoxy-tetrahydro-pyran-3,4,5-triol;

(2S,3R,4R,5S,6S)-2-[4-Cyclopropyl-3-(3,4-dihydro-2H-1,4-ethano-quinolin-7-ylmethyl)-phenyl]-6-methoxy-tetrahydro-pyran-3,4,5-triol;

(2S,3R,4R,5S,6S)-2-[4-Ethyl-3-(1,2,3,4-tetrahydro-quinoxalin-6-ylmethyl)-phenyl]-6-methoxy-tetrahydro-pyran-3,4,5-triol;

6-[2-Cyclopropyl-5-((2S,3R,4R,5S,6S)-3,4,5-tri hydroxy-6-methoxy-tetrahydro-pyran-2-yl)-benzyl]-3,4-dihydro-2H-benzo[1,4]oxazine-2-carboxylic acid;

6-[2-Cyclopropyl-5-((2S,3R,4R,5S,6S)-3,4,5-tri hydroxy-6-methoxy-tetrahydro-pyran-2-yl)-benzyl]-3,4-dihydro-2H-benzo[1,4]oxazine-2-carbonitrile;

(2S,3R,4R,5S,6S)-2-[4-Cyclopropyl-3-(5-methylamino-5,6,7,8-tetrahydro-naphthalen-2-ylmethyl)-phenyl]-6-methoxy-tetrahydro-pyran-3,4,5-triol;

(2S,3S,4R,5R,6S)-2-Methoxy-6-[4-oxetan-3-yl-3-(2,3,4,5-tetrahydro-benzo[b]oxepin-7-ylmethyl)-phenyl]-tetrahydro-pyran-3,4,5-triol;

(2S,3R,4R,5S,6S)-2-[4-Cyclopropyl-3-(2,3,4,5-tetrahydro-benzo[b]oxepin-7-ylmethyl)-phenyl]-6-methoxy-tetrahydro-pyran-3,4,5-triol;

(2S,3R,4R,5S,6S)-2-[4-Cyclopropyl-3-(2,3,4,5-tetra hydro-benzo[b]thiepin-7-ylmethyl)-phenyl]-6-methoxy-tetrahydro-pyran-3,4,5-triol;

(2S,3R,4R,5S,6S)-2-[4-Ethyl-3-(2,3,4,5-tetrahydro-benzo[b]oxepin-7-ylmethyl)-phenyl]-6-methoxy-tetra hydro-pyran-3,4,5-triol;

(2S,3R,4R,5S,6S)-2-[4-Chloro-3-(2,3,4,5-tetrahydro-benzo[b]oxepin-7-ylmethyl)-phenyl]-6-methoxy-tetra hydro-pyran-3,4,5-triol;

(2S,3R,4R,5S,6S)-2-[4-Cyclopropyl-3-(6,7,8,9-tetrahydro-5-oxa-9-aza-benzocyclohepten-3-ylmethyl)-phenyl]-6-methoxy-tetra hydro-pyran-3,4,5-triol;

(2S,3R,4R,5S)-2-[3-(2,3-Dihydro-benzo[1,4]dioxin-6-ylmethyl)-4-ethyl-phenyl]-6-phenylsulfanyl-tetrahydro-pyran-3,4,5-triol;

(2S,3R,4R,5S)-2-[3-(2,3-Dihydro-benzo[1,4]dioxin-6-ylmethyl)-4-ethyl-phenyl]-6-(thiophene-2-sulfonyl)-tetra hydro-pyran-3,4,5-triol;

(3S,4R,5R,6S)-2-Cyclopropanesulfonyl-6-[3-(2,3-dihydro-benzo[1,4]dioxin-6-ylmethyl)-4-ethyl-phenyl]-tetrahydro-pyran-3,4,5-triol; and (2S,3R,4R,5S)-2-[3-(2,3-Dihydro-benzo[1,4]dioxin-6-ylmethyl)-4-ethyl-phenyl]-6-(2,2,2-trifluoro-ethanesulfonyl)-tetrahydro-pyran-3,4,5-triol.

Embodiment 24: The compound of Embodiment 1, or a pharmaceutically acceptable salt thereof, wherein the compound is selected from the group consisting of:

(2S,3R,4R,5S)-2-[4-cyclopropyl-3-(2,3-dihydro-benzo[1,4]dioxin-6-ylmethyl)-phenyl]-6-methylsulfanyl-tetrahydro-pyran-3,4,5-triol;

(2S,3R,4R,5S,6R)-2-[3-(2,3-Dihydro-benzo[1,4]dioxin-6-ylmethyl)-4-ethyl-phenyl]-6-methylsulfanyl-tetrahydro-pyran-3,4,5-triol;

(2S,3R,4R,5S,6R)-2-(3-Chroman-6-ylmethyl-4-ethyl-phenyl)-6-methylsulfanyl-tetrahydropyran-3,4,5-triol;

(2S,3R,4R,5S,6R)-2-[4-Bromo-3-(2,3-dihydro-benzo[1,4]dioxin-6-ylmethyl)-phenyl]-6-methylsulfanyl-tetrahydro-pyran-3,4,5-triol;

(2S,3R,4R,5S,6R)-2-(3-Chroman-6-ylmethyl-4-cyclopropyl-phenyl)-6-methylsulfanyl-tetrahydropyran-3,4,5-triol;

(2S,3R,4R,5S,6R)-2-(4-Bromo-3-chroman-6-ylmethyl-phenyl)-6-methylsulfanyl-tetrahydropyran-3,4,5-triol;

(2S,3R,4R,5S,6R)-2-(4-Bromo-3-isochroman-7-ylmethyl-phenyl)-6-methylsulfanyl-tetrahydropyran-3,4,5-triol;

(2S,3R,4R,5S,6R)-2-(4-Ethyl-3-isochroman-7-ylmethyl-phenyl)-6-methylsulfanyl-tetrahydropyran-3,4,5-triol;

(2S,3R,4R,5S)-2-[4-Cyclopropyl-3-(2,3-dihydro-benzo[1,4]dioxin-6-ylmethyl)-phenyl]-6-methanesulfonyl-tetrahydro-pyran-3,4,5-triol;

(2S,3R,4R,5S,6R)-2-[3-(2,3-Dihydro-benzo[1,4]dioxin-6-ylmethyl)-4-ethyl-phenyl]-6-methanesulfonyl-tetrahydro-pyran-3,4,5-triol;

(2S,3R,4R,5S,6R)-2-(3-Chroman-6-ylmethyl-4-ethyl-phenyl)-6-methanesulfonyl-tetrahydropyran-3,4,5-triol;

(2S,3R,4R,5S,6R)-2-[4-Bromo-3-(2,3-dihydro-benzo[1,4]dioxin-6-ylmethyl)-phenyl]-6-methanesulfonyl-tetrahydro-pyran-3,4,5-triol;

(2S,3R,4R,5S,6R)-2-(3-Chroman-6-ylmethyl-4-cyclopropyl-phenyl)-6-methanesulfonyl-tetrahydropyran-3,4,5-triol;

(2S,3R,4R,5S,6R)-2-(4-Bromo-3-chroman-6-ylmethyl-phenyl)-6-methanesulfonyl-tetrahydropyran-3,4,5-triol;

(2S,3R,4R,5S,6R)-2-[4-Cyclopropyl-3-(2,3-dihydro-benzo[1,4]dioxin-6-ylmethyl)-phenyl]-6-methoxy-tetrahydro-pyran-3,4,5-triol;

(2S,3R,4R,5S,6S)-2-(4-Bromo-3-chroman-6-ylmethyl-phenyl)-6-methoxy-tetrahydro-pyran-3,4,5-triol;

(2S,3R,4R,5S,6S)-2-(3-Chroman-6-ylmethyl-4-ethyl-phenyl)-6-methoxy-tetrahydro-pyran-3,4,5-triol;

(2S,3R,4R,5S,6S)-2-(3-Chroman-6-ylmethyl-4-cyclopropyl-phenyl)-6-methoxy-tetrahydro-pyran-3,4,5-triol;

(2S,3R,4R,5S,6S)-2-[3-(2,3-Dihydro-benzo[1,4]dioxin-6-ylmethyl)-4-ethyl-phenyl]-6-methoxy-tetrahydro-pyran-3,4,5-triol; and N-[(3S,4R,5R,6S)-6-(3-chroman-6-ylmethyl-4-ethyl-phenyl)-3,4,5-trihydroxy-tetrahydro-pyran-2-yl]-N-propyl-acetamide.

Embodiment 25: A pharmaceutical composition comprising a therapeutically effective amount of a compound according to any one of Embodiments 1 to 24, or a pharmaceutically acceptable salt thereof, and one or more pharmaceutically acceptable carrier.

Embodiment 26: A combination comprising a therapeutically effective amount of a compound according to any one of Embodiments 1 to 24, or a pharmaceutically acceptable salt thereof, and one or more therapeutically active co-agents.

Embodiment 27: A method of inhibiting sodium D-glucose co-transporter activity in a subject, wherein the method comprises administering to the subject a therapeutically effective amount of the compound according to any one of Embodiments 1 to 24, or a pharmaceutically acceptable salt thereof.

Embodiment 28: A method of treating diabetes comprising administering a compound according to any one of Embodiments 1 to 24, or a pharmaceutically acceptable salt thereof, to a subject in need thereof.

Embodiment 29: A method of treating a disease or condition mediated by the sodium D-glucose co-transporter in a subject, comprising administering to the mammal in need thereof a therapeutically effective amount of a compound according to any one of Embodiments 1 to 24, or a pharmaceutically acceptable salt thereof.

Embodiment 30: The method according to Embodiment 29, wherein the disease or condition is metabolic syndrome, Syndrome X, diabetes, insulin resistance, decreased glucose tolerance, non-insulin-dependent diabetes mellitus, Type II diabetes, Type I diabetes, diabetic complications, a body weight disorder, obesity, or a leptin related disease.

Embodiment 31: The method according to Embodiment 30, wherein the disease or condition is dyslipidemia, obesity, insulin resistance, hypertension, microalbuminemia, hyperuricaemia, or hypercoagulability.

Embodiment 32: A compound of any one of Embodiments 1 to 24, or a pharmaceutically acceptable salt thereof, for use as a medicament.

Embodiment 33: A compound of any one of Embodiments 1 to 24, or a pharmaceutically acceptable salt thereof, for use in treating diabetes.

Embodiment 34: A compound of any one of Embodiments 1 to 24, or a pharmaceutically acceptable salt thereof, for use in treating a disease or condition in a subject mediated by sodium D-glucose co-transporter.

Embodiment 35: The compound according to Embodiment 34, or a pharmaceutically acceptable salt thereof, wherein the disease or condition is metabolic syndrome, Syndrome X, diabetes, insulin resistance, decreased glucose tolerance, non-insulin-dependent diabetes mellitus, Type II diabetes, Type I diabetes, diabetic complications, a body weight disorder, obesity, or a leptin related disease.

Embodiment 36: The compound according to Embodiment 35, or a pharmaceutically acceptable salt thereof, wherein the disease or condition is dyslipidemia, obesity, insulin resistance, hypertension, microalbuminemia, hyperuricaemia, or hypercoagulability.

Embodiment 37: Use of a compound according to any one of Embodiments 1 to 24, or a pharmaceutically acceptable salt thereof, in the manufacture of a medicament for the treatment of diabetes.

Embodiment 38: Use of a compound according to any one of Embodiments 1 to 24, or a pharmaceutically acceptable salt thereof, in the manufacture of a medicament for the treatment of a disorder or disease mediated by sodium D-glucose co-transporter.

Embodiment 39: Use of a compound according to Embodiment 38, or a pharmaceutically acceptable salt thereof, wherein the disease or condition is metabolic syndrome, Syndrome X, diabetes, insulin resistance, decreased glucose tolerance, non-insulin-dependent diabetes mellitus, Type II diabetes, Type I diabetes, diabetic complications, a body weight disorder, obesity, or a leptin related disease.

Embodiment 40: Use of a compound according to Embodiment 39, or a pharmaceutically acceptable salt thereof, wherein the disease or condition is dyslipidemia, obesity, insulin resistance, hypertension, microalbuminemia, hyperuricaemia, or hypercoagulability.

Embodiment 41: A pharmaceutical compositions comprising a therapeutically effective amount of a compound according to any one of Embodiments 1 to 24, or a pharmaceutically acceptable salt thereof, in combination with a therapeutically effective amount of another therapeutic agent.

Embodiment 42: A pharmaceutical combination comprising:
i) a compound according to any one of Embodiments 1 to 24, or a pharmaceutically acceptable salt thereof,
ii) at least one compound selected from
   a) antidiabetic agents,
   b) hypolipidemic agents,
   c) anti-obesity agents,
   d) anti-hypertensive agents,
   e) agonists of peroxisome proliferator-activator receptors.

The invention claimed is:

1. A compound represented by structural formula (I):

or a pharmaceutiacally acceptable salt thereof, wherein:
ring A is a 5-, 6- or 7-membered heterocyclyl;
X is O, $NR^5$, S, S(O) or $S(O)_2$;
V is hydrogen, halo or $-OR^{1b}$;
$R^1$, $R^1a$ and $R^{1b}$ are independently selected from the group consisting of hydrogen, $C_{1-6}$ alkyl, $C_{6-10}$aryl—$_{1-4}$alkyl, —C(O)$C_{6-10}$aryl and —C(O)$C_{1-6}$alkyl1kyl;
$R^2$ and $R^2a$, for each occurrence, are independently selected from the group consisting of halo, hydroxy, cyano, carboxy, $C_{1-6}$alkyl, $C_{1-6}$alkoxy and $C_{3-10}$cycloalkyl;
$R^3$ is halo, hydroxy, $C_{1-6}$alkyl, halo$C_{1-6}$alkyl, $C_{3-10}$cycloalkyl, $C_{1-6}$alkoxy, halo$C_{1-3}$alkoxy or a 3- to 7-membered heterocyclyl;
$R^4$ is a $C_{1-6}$alkyl, halo$C_{1-6}$alkyl, $C_{3-10}$cycloalkyl, $C_{6-10}$aryl, or a 5- to 10-membered heteroaryl;
$R^5$ is hydrogen, $C_{1-6}$alkyl, $C_{3-10}$cycloalkyl, or $C_{1-6}$alkanoyl; or
$R^4$ and $R^5$ together with the nitrogen to which they are attached form a 3- to 7-membered heterocyclyl;
n is 0, 1, 2, or 3; and
q is 0, 1, or 2.

2. The compound of claim 1, or a pharmaceutically acceptable salt thereof, wherein the group represented by the following formula:

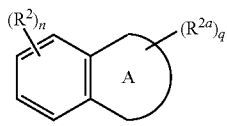

is selected from the group consisting of:

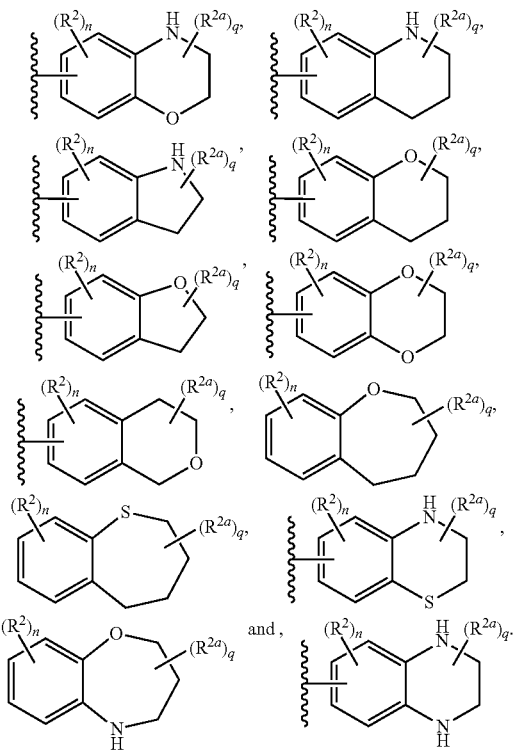

3. The compound of claim 1, or a pharmaceutically acceptable salt thereof, wherein the group represented by the following formula:

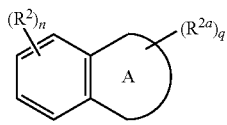

is selected from the group consisting of:

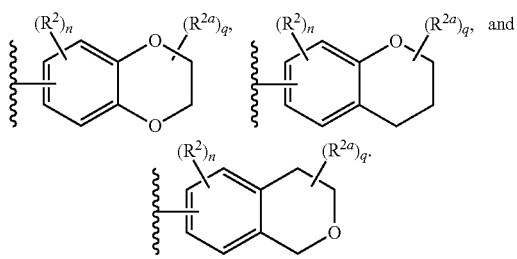

4. The compound of anyone of claim 1, or a pharmaceutically acceptable salt thereof, wherein the group represented by the following formula:

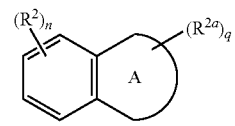

is selected from the group consisting of:

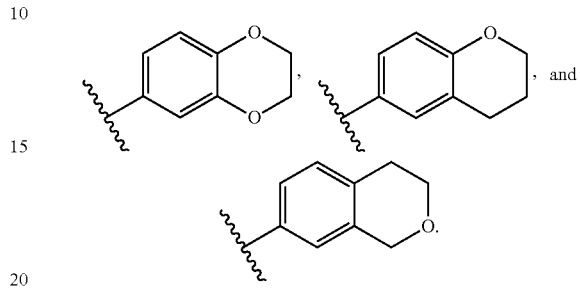

5. The compound of anyone of claim 1, or a pharmaceutically acceptable salt thereof, wherein the group represented by the following formula:

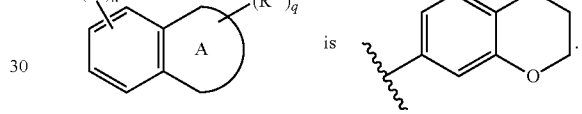

6. The compound of claim 1, or a pharmaceutically acceptable salt thereof, wherein n is 0.

7. The compound of anyone of claim 1, or a pharmaceutically acceptable salt thereof, wherein q is 0.

8. The compound of claim 1, or a pharmaceutically acceptable salt thereof, wherein V is —$OR^{1b}$.

9. The compound of claim 1, or a pharmaceutically acceptable salt thereof, wherein $R^1$, $R^1a$, and $R^{1b}$ are hydrogen.

10. The compound of claim 1, or a pharmaceutically acceptable salt thereof, wherein $R^3$ is halo, $C_{1-6}$alkyl, or $C_{3-10}$cycloalkyl.

11. The compound of claim 1, or a pharmaceutically acceptable salt thereof, wherein $R^3$ is bromo, ethyl or cyclopropyl.

12. The compound of claim 1, or a pharmaceutically acceptable salt thereof, wherein $R^3$ is ethyl.

13. The compound of claim 1, or a pharmaceutically acceptable salt thereof, wherein $R^4$ and $R^5$ together with the nitrogen to which they are attached form a pyrrolidino or a morpholino.

14. The compound of claim 1, or a pharmaceutically acceptable salt thereof, wherein the compound is selected from the group consisting of:

(2S,3R,4R,5S)-2-[4-cyclopropyl-3-(2,3-dihydro-benzo[1,4]dioxin-6-ylmethyl)-phenyl]-6-methylsulfanyl-tetrahydropyran-3,4,5-triol;

(2S,3R,4R,5S,6R)-2-[3-(2,3-Dihydro-benzo[1,4]dioxin-6-ylmethyl)-4-ethyl-phenyl]-6-methylsulfanyl-tetrahydropyran-3,4,5-triol;

(2S,3R,4R,5S,6R)-2-(3-Chroman-6-ylmethyl-4ethyl-phenyl)-6methylsulfanyl-tetrahydropyran-3,4,5-triol;

(2S,3R,4R,5S,6R)-2-[4-Bromo-3-(2,3dihydro-benzo[1,4]dioxin-6-ylmethyl)-phenyl]-6-methylsulfanyl-tetrahydropyran-3,4,5-triol;

(2S,3R,4R,5S,6R)-2-(3-Chroman-6-ylmethyl-4-cyclopropyl-phenyl)-6methylsulfanyl -tetrahydropyran-3,4,5-triol;

(2S,3R,4R,5S,6R)-2-(4-Bromo-3-chroman-6-ylmethyl-phenyl)-6-methylsulfanyltetrahydropyran-3,4,5-triol;

(2S,3R,4R,5S,6R)-2-(4-Bromo-3-isochroman-7-ylmethyl-phenyl)-6methylsulfanyl-tetrahydropyran-3,4,5-triol;

(2S,3R,4R,5S,6R)-2-(4-Ethyl-3-isochroman-7-ylmethyl-phenyl)-6-methylsulfanyltetrahydropyran-3,4,5-triol;

(2S,3R,4R,5S)-2-[4-Cyclopropyl-3-(2,3-dihydro-benzo[1,4]dioxin-6-ylmethyl)-phenyl]-6-methanesulfonyl-tetrahydro-pyran-3,4,5-triol;

(2S,3R,4R,5S,6R)-2-[4-(2,3-Dihydro-benzo[1,4]dioxin-6-ylmethyl)-4-ethyl-phenyl]-6-methanesulfonyl-tetrahydropyran-3,4,5-triol;

(2S,3R,4R,5S,6R)-2-(3-Chroman-6-ylmethyl-4-ethyl-phenyl)-6methanesulfonyl-tetrahydropyran-3,4,5-triol;

(2S,3R,4R,5S,6R)-2-[4-Bromo-3-(2,3-dihydro-benzo[1,4]dioxin-6-ylmethyl)-phenyl]-6-methanesulfonyl-tetrahydro-pyran-3,4,5-triol;

(2S,3R,4R,5S,6R)-2-(3-Chroman-6-ylmethyl-4-cyclopropyl-phenyl)-6methanesulfonyl-tetrahydro-pyran-3,4,5-triol;

(2S,3R,4R,5S,6R)-2-(4-Bromo-3-chroman-6-ylmethyl-phenyl)-6methanesulfonyl-tetrahydro-pyran-3,4,5-triol;

(2S,3R,4R,5S,6S)-2[4-Cyclopropyl-3-(2,3-dihydro-benzo[1,4]dioxin-6-ylmethyl)-phenyl]-6-methoxy-tetrahydro-pyran-3,4,5-triol;

(2S,3R,4R,5S,6S)-2-(4-Bromo-3-chroman-6-ylmethyl-phenyl)-6-methoxy-tetrahydro-pyran-3,4,5-triol;

(2S,3R,4R,5S,6S)-2-(3-Chroman-6-ylmethyl-4-ethyl-phenyl)-6-methoxy-tetrahydro-pyran-3,4,5-triol;

(2S,3R,4R,5S,6S)-2-(3-Chroman-6-ylmethyl-4-cyclopropyl-phenyl)-6methoxy-tetrahydro-pyran-3,4,5-triol;

(2S,3R,4R,5S,6S)-2-[4-(2,3-Dihydro-benzo[1,4]dioxin-6-ylmethyl)-4-ethyl-phenyl]-6-methoxy-tetrahydro-pyran-3,4,5-triol;

N-[-3S,4R,5R,6S)-6-(3-chroman-6-ylmethyl-4-ethyl-phenyl)-3,4,5-trihydroxy-tetrahydro -pyran-2-yl]-N-propyl-acetamide;

2S,3R,4R,5S,6R)-2[4-Cyclopropyl-3-(2,3,4,5-tetrahydro-benzo[b]oxepin-7-ylmethyl)phenyl]-6-methylsulfanyl-tetrahydro-pyran-3,4,5-triol;

(2S,3R,4R,5S,6R)-2-[4-Cyclopropyl-3-(2,3,4,5-tetrahydro-benzo[b]thiepin-7-ylmethyl)phenyl]-6-methylsulfanyl-tetrahydro-pyran-3,4,5-triol (2S,3R,4R,5S,6R)-2-[4-Ethyl-3-(2,3,4,5-tetrahydro-benzo[b]oxepin-7-ylmethyl)-phenyl]-6methylsulfanyl-tetrahydro-pyran-3,4,5-triol;

(2S,3R,4R,5S,6R)-2-[4-Cyclopropyl-3-(2,3,4,5-tetrahydro-benzo[b]oxepin -7-ylmethyl)-phenyl]-6-2ethylsulfanyl-tetrahydro-pyran-3,4,5-triol;

(2S,3R,4R,5S,6R)-2-[4-Chloro-3-(2,3,4,5-tetrahydro-benzo[b]oxepin-7-ylmethyl)-phenyl]6-methylsulfanyl-tetrahydro-pyran-3,4,5-triol;

(2S,3R,4R,5S,6R)-2-[4-Methoxy-3-(2,3,4,5-tetrahydro-benzo[b]oxepin-7-ylmethyl) -phenyl]-6-methylsulfanyl-tetrahydro-pyran-3,4,5-triol;

(2S,3R,4R,5S,6R)-2[4-Cyclopentyl-3-(2,3,4,5-tetrahydro-benzo[b]oxepin-7ylmethyl -phenyl]-6-methylsulfanyl-tetrahydro-pyran-3,4,5-triol;

(2S,3R,4R,5S,6R)-2-[4-Cyclobutyl-3-(2,3,4,5-tetrahydro-benzo[b]thiepin-7-ylmethyl)phenyl]-6-methylsulfanyl-tetrahydro-pyran-3,4,5-triol;

(2R,3S,4R,5R,6S)-2-Methylsulfanyl-6[4-oxetan-3-yl-3-(2,3,4,5-tetrahydrobenzo[b]oxepin-7-ylmethyl)-phenyl]tetrahydro-pyran-3,4,5-triol;

(2S,3R,4R,5S,6R)-2-[4-Cyclopropyl-3-(1,2,3,4-tetrahydro-quinolin-7-ylmethyl)-phenyl]-6-methanesulfonyl-tetrahydro-pyran-3,4,5-triol;

(2S,3R,4R,5S,6R)-2-[4-Cyclopropyl-3-(3,4-dihydro-2H-benzo[1,4]oxazin-6-ylmethyl) -phenyl]-6-methanesulfonyl-tetrahydro-pyran-3,4,5-triol;

(2S,3R,4R,5S,6R)-2-(4-cyclopropyl-3-((3,4-dihydrospiro[benzo[b][1,4]oxazine-2,1'-cyclopropane]-6-yl)methyl)phenyl)-6-(methylsulfonyl)tetrahydro-2H-pyran-3,4,5-triol;

(2S,3R,4R,5S,6R)-2[4-Cyclopropyl-3-(2-methyl-3,4-dihydro-2H-benzo[1,4]oxazin-6ylmethyl)-phenyl]-6-methanesulfonyl-tetrahydro-pyran-3,4,5-triol;

(2S,3R,4R,5S,6R)-2-[4-Cyclopropyl-3-(1,1-dioxo-1,2,3,4-tetrahydro-1lambda*6*-benzo[1,4]thiazin-6-ylmethyl)-phenyl]-6-methanesulfonyl-tetrahydro -pyran-3,4,5-triol;

(2S,3R,4R,5S,6R)-2[4-Cyclopentyl-3-(2,3,4,5-tetrahydro-benzo[b]oxepin-7-ylmethyl) -phenyl]-6-methanesulfonyl-tetrahydro-pyran-3,4,5-triol;

(2R,3S,4R,5R,6S)-2-Methanesulfonyl-6[4-oxetan-3-yl-3-(2,3,4,5tetrahydro -benzo[b]oxepin-7-ylmethyl)-phenylHetrahydro-pyran-3,4,5-triol;

(2S,3R,4R,5S,6S)-2-[4-(2,2-Dimethyl-3,4-dihydro-2H-benzo[1,4]oxazin-6-ylmethyl)-4ethyl-phenyl]-6-methoxy-tetrahydro-pyran-3,4,5-triol;

(2S,3R,4R,5S,6S)-2-[4-Ethyl-3-(1,2,3,4-tetrahydro-quinolin-6-ylmethyl)-phenyl]-6-methoxy-tetrahydro-pyran-3,4,5-triol;

(2S,3R,4R,5S,6S)-2[4-Cyclopropyl-3-(3,4-dihydro-2H-benzo[1,4]thiazin-6-ylmethyl) -phenyl]-6-methoxy-tetrahydro-pyran-3,4,5-triol;

(2S,3R,4R,5S,6S)-2-[4-Cyclopropyl-3-(3,4-dihydro-2H-1,4-ethano-quinolin-7-ylmethyl) -phenyl]-6-methoxy-tetrahydro-pyran-3,4,5-triol;

(2S,3R,4R,5S,6S)-2-[4--Ethyl-3-(1,2,3,4-tetrahydro-quinoxalin-6-ylmethyl)-phenyl]-6-methoxy-tetrahydro-pyran-3,4,5-triol;

6[2-Cyclopropyl-5-((2S,3R,4R,5S,6S)-3,4,5-trihydroxy-6-methoxy-tetrahydro-pyran-2y1)-benzyl]-3,4-dihydro-2H-benzo[1,4]oxazine-2-carboxylic acid;

6[2-Cyclopropyl-5-((2S,3R,4R,5S,6S)-3,4,5-trihydroxy-6-methoxy-tetrahydro-pyran-2y1)-benzyl]-3,4-dihydro-2H-benzo[1,4]oxazine-2-carbonitrile;

(2S,3R,4R,5S,6S)-2-[4-Cyclopropyl-3-(5-methylamino-5,6,7,8-tetrahydro-naphthalen-2-ylmethyl)-phenyl]-6-methoxy-tetrahydro-pyran-3,4,5-triol;

(2S,3S,4R,5R,6S)-2-Methoxy-6[4-oxetan-3-yl-3-(2,3,4,5-tetrahydro-benzo[b]oxepin-7-ylmethyl)-phenylHetrahydro-pyran-3,4,5-triol;

(2S,3R,4R,5S,6S)-2-[4-Cyclopropyl-3-(2,3,4,5-tetrahydro-benzo[b]oxepin-7-ylmethyl) -phenyl]-6-methoxy-tetrahydro-pyran-3,4,5-triol;

(2S,3R,4R,5S,6S)-2-[4-Cyclopropyl-3-(2,3,4,5-tetrahydro-benzo[b]thiepin-7-ylmethyl) -phenyl]-6-methoxy-tetrahydro-pyran-3,4,5-triol;

(2S,3R,4R,5S,6S)-2-[4-Ethyl-3-(2,3,4,5-tetrahydro-benzo[b]oxepin-7-ylmethyl)-phenyl]-6-methoxy-tetrahydro-pyran-3,4,5-triol;

(2S,3R,4R,5S,6S)-2-[4-Chloro-3-(2,3,4,5-tetrahydro-benzo[b]oxepin-7-ylmethyl)-phenyl]-6-methoxy-tetrahydro-pyran-3,4,5-triol;

(2S,3R,4R,5S,6S)-2-[4-Cyclopropyl-3-(6,7,8,9-tetrahydro-5-oxa-9aza -benzocyclohepten-3-ylmethyl)-phenyl]-6-methoxy-tetrahydro-pyran-3,4,5-triol;

(2S,3R,4R,5S)-2-[4-(2,3-Dihydro-benzo[1,4]dioxin-6-ylmethyl)-4-ethyl-phenyl]-6-phenylsulfanyl-tetrahydropyran-3,4,5-triol;

(2S,3R,4R,5S)-2-[4-(2,3-Dihydro-benzo[1,4]dioxin-6-ylmethyl)-4-ethyl-phenyl]-6-(thiophene-2-sulfonyl)-tetrahydropyran-3,4,5-triol;

(3S,4R,5R,6S)-2-Cyclopropanesulfonyl-643-(2,3-dihydro-benzo[1,4]dioxin-6-ylmethyl)-4-ethyl-phenylHetrahydro-pyran-3,4,5-triol; and (2S,3R,4R,5S)-2-[4-(2,3-Dihydro-benzo[1,4]dioxin-6-ylmethyl)-4-ethyl-phenyl]-6-(2,2,2-trifluoro-ethanesulfonyl)-tetrahydropyran-3,4,5-triol.

15. The compound of claim 1, or a pharmaceutically acceptable salt thereof, wherein the compound is selected from the group consisting of:
- (2S,3R,4R,5S)-2-[4-cyclopropyl-3-(2,3-dihydro-benzo[1,4]dioxin-6-ylmethyl)-phenyl]-6-methylsulfanyl-tetrahydropyran-3,4,5-triol;
- (2S,3R,4R,5S,6R)-2-[4-(2,3-Dihydro-benzo[1,4]dioxin-6-ylmethyl)-4-ethyl-phenyl]-6-methylsulfanyl-tetrahydropyran-3,4,5-triol;
- (2S,3R,4R,5S,6R)-2-(3-Chroman-6-ylmethyl-4ethyl-phenyl)-6methylsulfanyl-tetrahydropyran-3,4,5-triol;
- (2S,3R,4R,5S,6R)-2-[4-Bromo-3-(2,3-dihydro-benzo[1,4]dioxin-6-ylmethyl)-phenyl]-6-methylsulfanyl-tetrahydropyran-3,4,5-triol;
- (2S,3R,4R,5S,6R)-2-(3-Chroman-6-ylmethyl-4-cyclopropyl-phenyl)-6methylsulfanyl-tetrahydropyran-3,4,5-triol;
- (2S,3R,4R,5S,6R)-2-(4-Bromo-3-chroman-6-ylmethyl-phenyI)-6methylsulfanyl-tetrahydropyran-3,4,5-triol;
- (2S,3R,4R,5S,6R)-2-(4-Bromo-3-isochroman-7-ylmethyl-phenyI)-6methylsulfanyl-tetrahydropyran-3,4,5-triol;
- (2S,3R,4R,5S,6R)-2-(4-Ethyl-3-isochroman-7-ylmethyl-phenyl)-6methylsulfanyl-tetrahydropyran-3,4,5-triol;
- (2S,3R,4R,5S)-2-[4-Cyclopropyl-3-(2,3dihydro-benzo[1,4]dioxin-6-ylmethyl)-phenyl]-6-methanesulfonyl-tetrahydro-pyran-3,4,5-triol;
- (2S,3R,4R,5S,6R)-2-[4-(2,3-Dihydro-benzo[1,4]dioxin-6-ylmethyl)-4-ethyl-phenyl]-6-methanesulfonyl-tetrahydropyran-3,4,5-triol;
- (2S,3R,4R,5S,6R)-2-(3-Chroman-6-ylmethyl-4-ethyl-phenyl)-6methanesulfonyl-tetrahydropyran-3,4,5-triol;
- (2S,3R,4R,5S,6R)-2-[4-Bromo-3-(2,3dihydro-benzo[1,4]dioxin-6-ylmethyl)-phenyl]-6-methanesulfonyl-tetrahydro-pyran-3,4,5-triol;
- (2S,3R,4R,5S,6R)-2-(3-Chroman-6-ylmethyl-4-cyclopropyl-phenyl)-6methanesulfonyl-tetrahydro-pyran-3,4,5-triol;
- (2S,3R,4R,5S,6R)-2-(4-Bromo-3-chroman-6-ylmethyl-phenyI)-6methanesulfonyl-tetrahydro-pyran-3,4,5-triol;
- (2S,3R,4R,5S,6S)-2[4-Cyclopropyl-3-(2,3-dihydro-benzo[1,4]dioxin-6-ylmethyl)-phenyl]-6-methoxy-tetrahydro-pyran-3,4,5-triol;
- (2S,3R,4R,5S,6S)-2-(4-Bromo-3-chroman-6-ylmethyl-phenyI)-6-methoxy-tetrahydropyran-3,4,5-triol;
- (2S,3R,4R,5S,6S)-2-(3-Chroman-6-ylmethyl-4-ethyl-phenyl)-6-methoxy-tetrahydropyran-3,4,5-triol;
- (2S,3R,4R,5S,6S)-2-(3-Chroman-6-ylmethyl-4-cyclopropyl-phenyl)-6-methoxytetrahydro-pyran-3,4,5-triol;
- (2S,3R,4R,5S,6S)-2-[4-(2,3-Dihydro-benzo[1,4]dioxin-6-ylmethyl)-4-ethyl-phenyl]-6-methoxy-tetrahydro-pyran-3,4,5-triol; and
- N-[(3S,4R,5R,6S)-6-(3-chroman-6-ylmethyl-4-ethyl-phenyl)-3,4,5-trihydroxy-tetrahydro-pyran-2-yl]-N-propyl-acetamide.

16. A pharmaceutical composition comprising a therapeutically effective amount of a compound according to claim 1, or a pharmaceutically acceptable salt thereof, and one or more pharmaceutically acceptable carrier.

17. A method of treating a disease or condition in a subject wherein the disease or condition is selected from Syndrome X, diabetes, insulin resistance, decreased glucose tolerance, non-insulin-dependent diabetes mellitus, Type II diabetes, Type I diabetes, dyslipidemia, obesity, hypertension, microalbuminemia and disorders arising from hyperglycemia, comprising administering to the mammal in need thereof a therapeutically effective amount of a compound according to claim 1, or a pharmaceutically acceptable salt thereof.

18. A pharmaceutical combination comprising:
i) a compound according to claim 1, or a pharmaceutically acceptable salt thereof,
ii) at least one compound selected from
   a) antidiabetic agents,
   b) hypolipidemic agents,
   c) anti-obesity agents,
   d) anti-hypertensive agents,
   e) agonists of peroxisome proliferator-activator receptors.

* * * * *